(12) United States Patent
Clymer et al.

(10) Patent No.: US 10,568,566 B2
(45) Date of Patent: Feb. 25, 2020

(54) USE OF BIOMARKERS AND THERAPEUTIC AGENTS WITH SURGICAL DEVICES

(71) Applicant: Ethicon LLC, Guaynabo, PR (US)

(72) Inventors: Jeffrey W. Clymer, Mason, OH (US); Prasanna Malaviya, Mason, OH (US); Donna L. Korvick, Maineville, OH (US); Kevin L. Houser, Springboro, OH (US); Frederick E. Shelton, IV, Hillsboro, OH (US); Chester O. Baxter, III, Loveland, OH (US); Taylor W. Aronhalt, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 107 days.

(21) Appl. No.: 15/264,880

(22) Filed: Sep. 14, 2016

(65) Prior Publication Data

US 2017/0000413 A1    Jan. 5, 2017

Related U.S. Application Data

(60) Continuation of application No. 14/062,276, filed on Oct. 24, 2013, now Pat. No. 9,456,779, which is a
(Continued)

(51) Int. Cl.
*A61B 5/00* (2006.01)
*A61B 18/14* (2006.01)
(Continued)

(52) U.S. Cl.
CPC ........ *A61B 5/4839* (2013.01); *A61B 5/14546* (2013.01); *A61B 5/486* (2013.01);
(Continued)

(58) Field of Classification Search
CPC . A61B 10/0283; A61B 10/06; A61B 18/1445; A61B 2046/236;
(Continued)

(56) References Cited

U.S. PATENT DOCUMENTS

| | | | | |
|---|---|---|---|---|
| 4,417,576 A | * | 11/1983 | Baran | A61M 16/04 128/207.15 |
| 5,180,364 A | * | 1/1993 | Ginsburg | A61M 25/0075 600/435 |

(Continued)

FOREIGN PATENT DOCUMENTS

| | | |
|---|---|---|
| WO | WO 2004/006787 | 1/2004 |
| WO | WO 2004/037095 | 5/2004 |

OTHER PUBLICATIONS

Bolstad, B.M. et al., "A comparison of normalization methods for high density oligonucleotide array data based on variance and bias," Bioinformatics, vol. 19(2) pp. 185-193 (Abstract).
(Continued)

*Primary Examiner* — Quynh-Nhu H. Vu
(74) *Attorney, Agent, or Firm* — Frost Brown Todd LLC

(57) ABSTRACT

Biomarkers are collected and used to determine biological propensities of a patient, to determine the efficacy of medical devices, to select and administer therapeutic agents, to select medical devices, to make adjustments to medical devices, and/or to adjust surgical techniques. An apparatus includes a port to draw a biological fluid (e.g., a mist) from a surgical site. The apparatus includes a sensor having a cantilevered beam. The beam includes substances selected to attract certain biomarkers as the fluid is communicated across the beam. The same apparatus or another apparatus is used to administer a therapeutic agent based at least in part on collected biomarker data. The therapeutic agent delivery apparatus may include a device that is also used to create a wound at a surgical site. For instance, a harmonic surgical instrument may be used to both collect biomarkers and administer a therapeutic agent (e.g., gene therapy using sonoporation).

20 Claims, 37 Drawing Sheets

Related U.S. Application Data division of application No. 12/971,249, filed on Dec. 17, 2010, now Pat. No. 8,591,459.

(60) Provisional application No. 61/288,375, filed on Dec. 21, 2009.

(51) Int. Cl.
| | |
|---|---|
| *A61B 5/145* | (2006.01) |
| *A61B 10/02* | (2006.01) |
| *A61B 10/06* | (2006.01) |
| *A61M 37/00* | (2006.01) |
| *A61B 46/23* | (2016.01) |

(52) U.S. Cl.
CPC ............ *A61B 5/7282* (2013.01); *A61B 5/742* (2013.01); *A61B 10/0283* (2013.01); *A61B 10/06* (2013.01); *A61B 18/1445* (2013.01); *A61B 2046/236* (2016.02); *A61B 2218/008* (2013.01); *A61M 2037/0007* (2013.01)

(58) Field of Classification Search
CPC .......... A61B 2218/008; A61B 5/14546; A61B 5/4839; A61B 5/486; A61B 5/7282; A61B 5/742; A61B 17/320092; A61B 17/3476; A61B 2018/1455; A61B 2018/1457; A61B 5/150442; A61B 5/150458; A61B 2017/00353; A61B 17/320016; A61B 17/320068; A61M 2037/0007
See application file for complete search history.

(56) References Cited

U.S. PATENT DOCUMENTS

| | | | |
|---|---|---|---|
| 6,067,991 A | 5/2000 | Forsell | |
| 6,187,743 B1 | 2/2001 | Obi-Tabot | |
| 6,689,146 B1 | 2/2004 | Himes | |
| 7,108,696 B2 | 9/2006 | Daniel et al. | |
| 7,300,446 B2 | 11/2007 | Beaupre | |
| 7,351,240 B2 | 4/2008 | Hassler, Jr. et al. | |
| 7,390,294 B2 | 6/2008 | Hassler, Jr. et al. | |
| 7,416,528 B2 | 8/2008 | Crawford et al. | |
| 7,479,148 B2 * | 1/2009 | Beaupre ......... | A61B 17/320092 606/169 |
| 7,569,789 B2 | 8/2009 | Hayenga et al. | |
| 7,673,783 B2 * | 3/2010 | Morgan ........... | A61B 17/07207 227/180.1 |
| 7,699,770 B2 | 4/2010 | Hassler, Jr. et al. | |
| 7,993,854 B2 | 8/2011 | Mutharasan et al. | |
| 8,007,474 B2 | 8/2011 | Uth et al. | |
| 8,016,745 B2 | 9/2011 | Hassler et al. | |
| 8,034,553 B2 | 10/2011 | McGrath | |
| 8,210,411 B2 | 7/2012 | Yates et al. | |
| 8,252,012 B2 | 8/2012 | Stulen | |
| 8,374,796 B2 | 2/2013 | Fernandez | |
| 8,550,981 B2 | 10/2013 | Woodruff et al. | |
| 8,591,459 B2 | 11/2013 | Clymer et al. | |
| 8,801,701 B2 | 8/2014 | Chopra et al. | |
| 2001/0047183 A1 | 11/2001 | Privitera et al. | |
| 2004/0038292 A1 | 2/2004 | Burslem et al. | |
| 2006/0079874 A1 | 4/2006 | Faller et al. | |
| 2006/0224160 A1 | 10/2006 | Trieu et al. | |
| 2007/0191712 A1 * | 8/2007 | Messerly ........ | A61B 17/320068 600/439 |
| 2007/0191713 A1 | 8/2007 | Eichmann et al. | |
| 2007/0282333 A1 * | 12/2007 | Fortson .......... | A61B 17/320092 606/50 |
| 2007/0299468 A1 * | 12/2007 | Viola ................ | A61B 5/0084 606/205 |
| 2008/0004528 A1 * | 1/2008 | Fitzsimons ............. | A61B 8/12 600/439 |
| 2008/0200940 A1 | 8/2008 | Eichmann et al. | |
| 2008/0234709 A1 | 9/2008 | Houser | |
| 2009/0054825 A1 * | 2/2009 | Melsheimer ........ | A61M 25/003 604/6.16 |
| 2009/0143806 A1 * | 6/2009 | Witt ............... | A61B 17/320092 606/169 |
| 2010/0075340 A1 | 3/2010 | Javanmard et al. | |
| 2011/0158979 A1 | 6/2011 | Hamet et al. | |
| 2011/0282144 A1 | 11/2011 | Gettman | |
| 2012/0040852 A1 | 2/2012 | Levin et al. | |

OTHER PUBLICATIONS

Liang, H.D. et al., "Optimisation of Ultrasound-Mediated Gene Transfer (Sonoporation) in Skeletal Muscle Cells," Ultrasound in Med. & Biol., vol. 30(11) (2004) pp. 1523-1529.

Lin, C.R et al., "Sonoporation-Mediated Gene Transfer into Adult Rat Dorsal Root Ganglion Cells," Journal of Biomedical Science, vol. 17 (2010) 44, pp. 1-6.

Negishi, Y. et al, "Delivery of an Angiogenic Gene into Ischemic Muscle by Novel Bubble Liposomes Followed By Ultrasound Exposure," Pharm. Res. (Oct. 8, 2010).

Taniyama, Y. et al., "Development of Safe and Efficient Novel Nonviral Gene Transfer Using Ultrasound: Enhancement of Transfection Efficiency of Naked Plasmid DNA in Skeletal Muscle," Gene Therapy, vol. 9(6) (Mar. 2002) pp. 372-380.

Tsai, S. et al., "Association of Imprinted Genes with Reproductive Efficiency in Swine," Animal Genetics, vol. 37 (2006) p. 423-424 (Abstract).

International Search Report dated May 25, 2011 for Application No. PCT/US2010/061422.

International Preliminary Report on Patentability dated Jun. 26, 2012 for Application No. PCT/US2010/061422.

Invitation to Pay Additional Fees and, Where Applicable, Protest Fee, dated Mar. 2, 2011 for Application No. PCT/US2010/061422.

Office Action Non-Final dated Apr. 16, 2012 for U.S. Appl. No. 12/971,249.

Office Action Final dated Aug. 28, 2012 for U.S. Appl. No. 12/971,249.

Office Action Non-Final dated Feb. 21, 2013 for U.S. Appl. No. 12/971,249.

Notice of Allowance dated Jul. 12, 2013 for U.S. Appl. No. 12/971,249.

Office Action Non-Final Rejection dated May 27, 2015 for U.S. Appl. No. 14/062,276.

Office Action Non-Final Rejection dated Sep. 2, 2015 for U.S. Appl. No. 14/062,276.

Notice of Allowance dated Feb. 3, 2016 for U.S. Appl. No. 14/062,276.

Notice of Allowance dated Feb. 19, 2016 for U.S. Appl. No. 14/062,276.

Notice of Allowance dated May 24, 2016 for U.S. Appl. No. 14/062,276.

U.S. Appl. No. 61/288,375, filed Dec. 21, 2009.

* cited by examiner

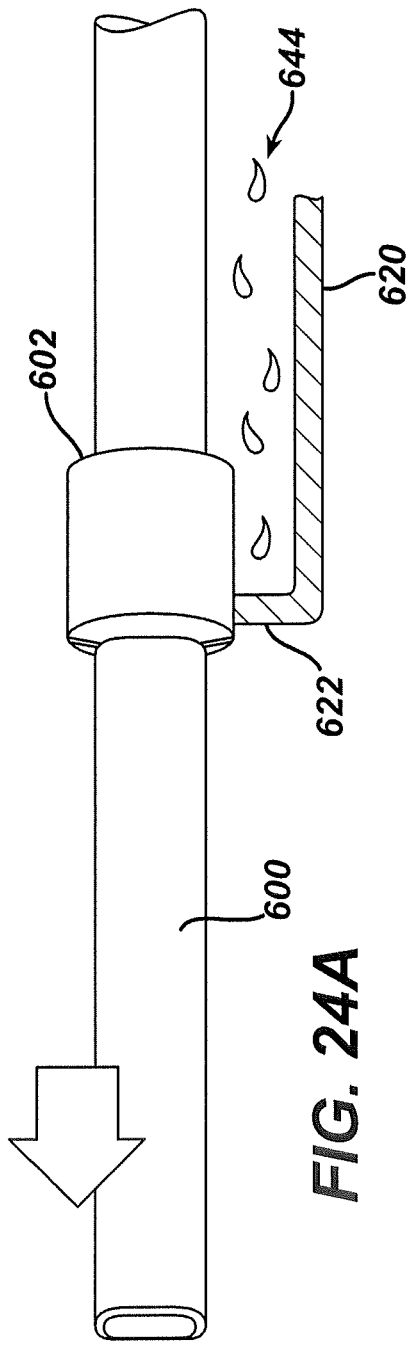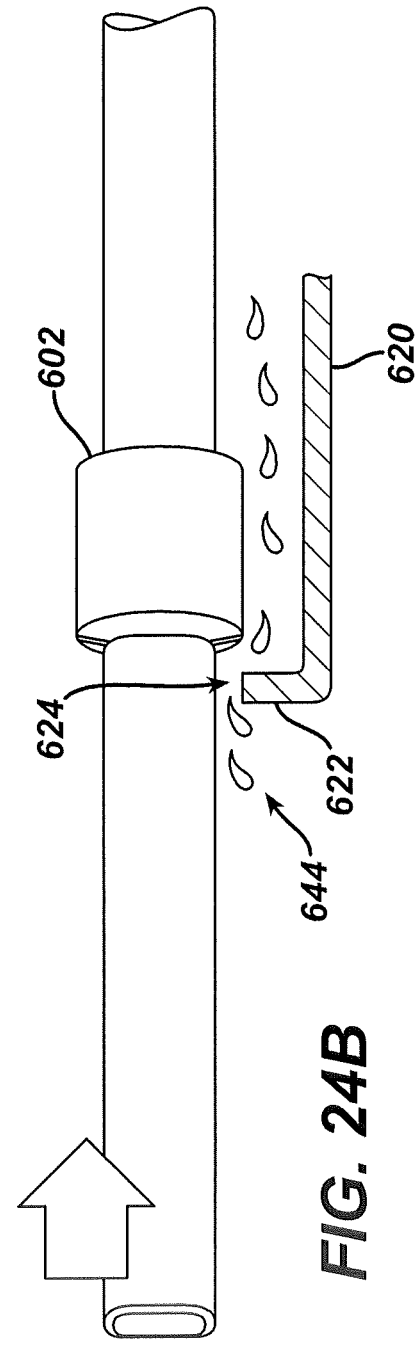

US 10,568,566 B2

USE OF BIOMARKERS AND THERAPEUTIC AGENTS WITH SURGICAL DEVICES

PRIORITY

This application is a continuation of U.S. patent application Ser. No. 14/062,276, entitled "Use of Biomarkers and Therapeutic Agents with Surgical Devices", filed Oct. 24, 2013, published as U.S. Pub. No. 2014/0051950, issued as U.S. Pat. No. 9,456,779 on Oct. 4, 2016, the disclosure of which is incorporated by reference herein, which is a divisional of U.S. patent application Ser. No. 12/971,249, entitled "Use of Biomarkers and Therapeutic Agents with Surgical Devices," filed Dec. 17, 2010, now U.S. Pat. No. 8,591,459, issued on Nov. 26, 2013, the disclosure of which is incorporated by reference herein, which claims priority to U.S. Provisional Patent Application Ser. No. 61/288,375, entitled "Method of Developing Surgical Devices Using Biomarkers," filed Dec. 21, 2009, the disclosure of which is incorporated by reference herein.

BACKGROUND

Tissue trauma resulting in a wound may be an unavoidable consequence of accidental or intentional injury (e.g., from surgery, etc.). The process of wound healing is thought by some to take place in four stages. The first stage is hemostasis which may begin immediately after the cutting occurs. In hemostasis, clotting may occur by natural means of platelet degranulation. Hemostasis may also be induced by artificial means to affect protein denaturation. The second stage is inflammation. In this stage, the immune system may provide a response to the threat of possible infection via signaling to defensive immune cells such as neutrophils and macrophages. The third stage is the proliferation stage. In this stage, fibroblasts may enter the wound area and produce large amounts of collagen that result in scar formation. A prolonged hemostatic or inflammatory stage may result in additional scar formation that delays both this third stage and the final stage of wound healing. The final stage of wound healing is remodeling. This may occur once a scar has formed and the breaking strength of the wound begins to increase. In this stage, the temporary collagen may be replaced by permanent tissue and the scar slowly fades. The duration of this final stage may depend upon how much scar tissue was formed in the previous stage.

While a variety of methods for monitoring the progress of wound healing have been made and used, it is believed that no one prior to the inventor(s) has made or used the technology as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 24A depicts a top cross-sectional view of another exemplary harmonic blade having a sheath and a therapeutic agent delivery feature, with the blade in a distal position while activated;

FIG. 24B depicts a top cross-sectional view of the harmonic blade of FIG. 24A, with the blade in a proximal position while activated;

Figure 1:
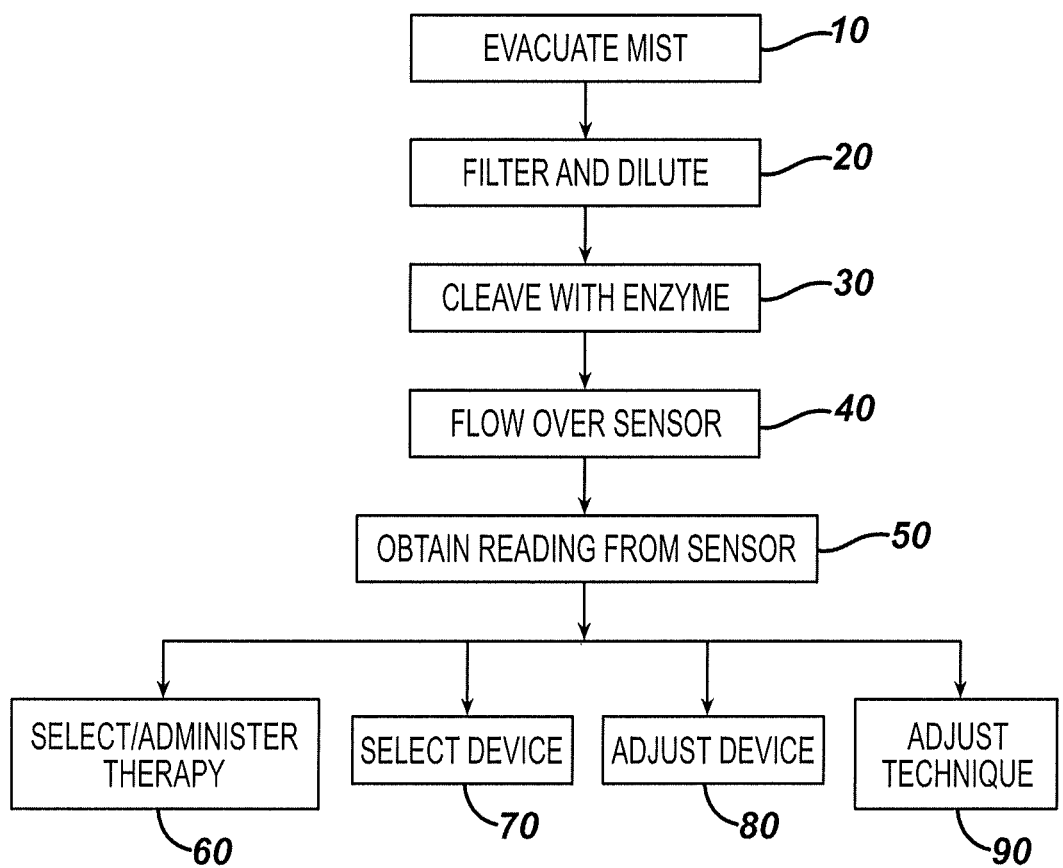
FIG. 1 depicts a flow diagram of an exemplary method of processing biomarkers.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Definitions

Antibody as used herein includes polyclonal and monoclonal antibodies, single chain, chimeric and humanised antibodies, as well as antibody fragments, whether produced by recombinant or proteolytic means. The term is also meant to include the products of any antibody-derived expression libraries, e.g. single-chain Fv or Fab fragment expression libraries.

The term "gene" has its meaning as understood in the art. However, it will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs and miRNAs. For clarity, the term gene generally refers to a portion of a nucleic acid that encodes a protein or functional RNA; however, the term may optionally encompass regulatory sequences. In some cases, the gene includes regulatory sequences involved in transcription, or message production or composition. In other examples, the gene comprises transcribed sequences that encode for a protein, polypeptide or peptide. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

Markers/biomarkers may include genes, proteins, metabolites (e.g., vitamins, etc.), and the like. By way of example only, a marker/biomarker may also include any molecule derived from a gene, e.g., a transcript of the gene, a sense (coding) or antisense (non-coding) probe sequence derived from the gene, or a full length or partial length translation product of the gene or an antibody thereto, which can be used to monitor a condition, disorder, disease, or the status in the progression of a process, e.g. a healing process or the progression in a disease. Biomarkers may be labeled to assist detection, the choice of label being directed by the nature of the biomarker. Suitable labels may include radionucleotides, enzymes, fluorescent, chemiluminescent, or chromogenic agents as well as substrates, cofactors, inhibitors, magnetic particles. Other suitable markers/biomarkers will be apparent to those of ordinary skill in the art in view of the teachings herein.

RNA refers to a molecule comprising at least one ribonucleotide residue. The term "ribonucleotide" means a nucleotide with a hydroxyl group at the 2' position of a beta-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of an RNAi agent or internally, for example at one or more nucleotides of the RNA. Nucleotides in the RNA molecules of the instant technology can also comprise non-standard nucleotides, such as non-naturally occurring nucleotides or chemically synthesized nucleotides or deoxynucleotides. These altered RNAs can be referred to as analogs or analogs of naturally occurring RNA.

It should also be understood that the term "therapeutic agent" herein is intended to broadly encompass various kinds of agents and medical substances, including but not limited to gene therapies, stem cell therapies, hemostatic agents, healing agents, adhesives, sealants, anti-bacterial agents, infection-resistant agents, analgesics, conventional pharmaceutical drugs, other chemicals, liquids, powders, etc. It should also be understood that the use of the term "therapeutic agent" herein is not intended to demonstrate that concepts described herein are limited to only agents that are used for therapeutic purposes. The term "therapeutic agent" as used herein is intended to encompass various kinds of medical agents/substances, including but not limited to those used for preventative, prophylactic, and/or remedial purposes, and including those used for various purposes that might not be considered "therapeutic" in a traditional sense of the word "therapeutic." Various kinds of agents/substances that may be used in accordance with the teachings herein, as well as various purposes for which such agents/substances may be used, will be apparent to those of ordinary skill in the art in view of the teachings herein. All such agents/substances/purposes are intended to be encompassed by the use of the term "therapeutic agent" herein.

II. Overview

A. Principles of Biomarkers

Examples described herein relate to a principle that the expression of certain biomarkers may be different in wound tissues as compared to the expression of those same biomarkers in healthy tissues. More particularly, examples described herein relate to methods and probes for investigating and evaluating the presence of RNA species that are differentially expressed in wound and normal tissue (e.g., in realtime) as a function of the type of surgical device used to make the incision and/or as a function of other factors. Examples described herein also relate to the use of specific genes and their translation products to monitor wound healing and/or to detect disorders or diseases characterized by impaired or excessive wound healing. Examples described herein also relate to methods for the evaluation and identification of compounds useful for the treatment of wounds, inflammation and wound healing disorders, compounds identified by such screening methods, the use of such compounds in the manufacture of medicaments or in methods of medical treatment. In addition, examples described herein provide methods to assess the utility and efficiency of surgical cutting devices by monitoring levels of biomarkers which are indicative of hemostasis, inflammation, chemotaxis, immune response, fibrosis and/or scar remodeling. Still other examples of how biomarkers may be used in conjunction with various surgical devices are described herein.

Many medical procedures require surgery to be performed in which tissues are cut, blood vessels are coagulated, other tissue is excised, and the cut is subsequently closed and allowed to heal. A surgical incision by its very nature may cause a wide range of tissue damage. Where the medical procedure requires some type of incision, the surgeon may have a choice of the method of incision and method of coagulation control and thus may choose a surgical device that provides optimum hemostatic control with minimal tissue damage. One type of device for surgical cutting is the steel scalpel. The scalpel may cause relatively minimal tissue damage. However since a steel scalpel may provide almost no hemostatic control, other means may need be taken to close blood vessels and stop bleeding. One method developed to both cut and coagulate is electrosurgery. In this method, an electric current is passed through the tissue, thereby heating the tissue to a high temperature. This heat both cuts and coagulates the tissue via protein denaturation. Although electrosurgery may be viewed as an advance over the steel scalpel in terms of hemostasis, there may ultimately be more tissue damage due to the high heat of electrosurgical device which may lead to increased inflammation, additional pain and a longer period of wound healing.

Some other devices may offer effective cutting and hemostasis with relatively reduced tissue damage. Some such devices include "Harmonic" ultrasonic surgical devices provided by Ethicon Endo-Surgery, Inc. of Cincinnati, Ohio, such as those provided under the names Harmonic FOCUS, Harmonic WAVE, Harmonic ACE, and Harmonic SYNERGY to name a few. These devices operate via high-frequency (e.g., 55.5 kHz) oscillation of a blade that both cuts and coagulates tissue. Coagulation is achieved through heating which is in turn induced by the mechanical vibratory action of the blade. Use of such energized surgical techniques may result in denatured or degraded proteins. A potential side benefit of ultrasonic devices is that they can, in certain configurations, be used to liquefy and aerosolize tissues making direct sampling for biomarkers easily obtainable and with little degradation of the final protein or mRNA. Ultrasonic devices may also create micropores in the walls of tissue cells in a patient ("sonoporation"), which may facilitate transfer of genes and/or other agents into the patient's cells as will be described in greater detail below.

The central response to tissue damage is provided via genetic control. The DNA of various response genes are translated into mRNA which can then induce the production of a corresponding protein. Both the mRNA and protein may be found to be useful biomarkers. Pre-existing proteins may also be damaged by surgical intervention, and hence these proteins or their remnants may be utilized as biomarkers for tissue damage.

Poor hemostatic control may lead to increased bleeding and tissue damage. Likewise, excessive hemostatic control (e.g., via extreme heating) may injure tissue unnecessarily. In either case, tissue damage may result in increased inflammation, pain, scar formation and a longer period of scar remodeling. Therefore, there may be a need for improved surgical devices that cause less trauma to neighboring tissue and for methods to evaluate such devices.

To assist in evaluating the extent of trauma caused by a surgical device, biomarkers may be chosen from the different phases of the wound healing process. The first phase of wound healing, hemostasis, may occur immediately after incision. During hemostasis the bleeding may be controlled by natural coagulation, suture, or heat denaturation of proteins. A high level of heat may lead to a large residue of hemoglobin fragments, and it is believed that these fragments may be suitable biomarkers for quantitatively assessing the trauma inflicted by surgical devices. Other biomarkers that may be useful at this stage of wound healing may include components of platelets and early mediators of the inflammatory response.

Biomarkers such as hemoglobin fragments, platelet components and inflammatory mediators may be viewed as indicators that the tissue has been injured and higher levels may in turn reflect a more damaging surgical device. On the other hand, certain biomarkers may be viewed as indicative of the healing process, and a less damaging surgical device may enhance the presence of these particular markers. Examples include albumin, transferrin and vimentin. These proteins are believed to aid in the healing process. It is believed that an assay for these proteins may be used to distinguish the amount of tissue damage inflicted by different surgical devices, with a "better" surgical device reducing the level of these proteins by a smaller amount.

Inflammation constitutes the second phase of wound healing. In this phase, the immune system sends out a response to prevent infection. Chemokines, such as CXCL8 (IL-8), call in immune cells, such as neutrophils and macrophages. A higher level of chemokines may generally reflect greater tissue damage from a particular surgical device and lower levels of chemokines may reflect a less damaging surgical device.

The inflammation stage is followed by a proliferation phase. At this point cytokines, such as TGF-$\beta$, induce the proliferation of fibroblasts that produce collagen. Since TGF-$\beta$ is produced at several stages of the wound healing process and at varying levels, it may in general not be as good a biomarker as the others mentioned. Since the proliferation phase follows the inflammation phase, use of biomarkers at this point may necessarily be delayed compared to biomarkers that occur earlier in the wound healing process.

The final phase of wound healing is remodeling in which collagen levels are decreased, the wound breaking strength is increased and the scar slowly disappears. Since this is the last and slowest phase of wound healing, biomarkers taken from it may be less useful in quickly assessing the trauma inflicted by a surgical device. Furthermore, biomarkers from the initial phases may be more likely to be predictive of the intensity and length of the later phases. Greater hemostasis trauma or inflammation may lead to more fibroblast proliferation, collagen deposition, and longer time for scar remodeling.

It should also be understood that when an incision or other biological alteration is made by a surgical instrument or other type of medical device, the resulting changes in biomarker expressions may have a cascading effect. For instance, the biological alteration may initially produce a first change in one or more biomarkers; while the first change in one or more biomarkers may lead to a second change in another one or more biomarkers; and so on. By way of example only, a biological stimulus might include infection by a pathogenic organism, such as a virus or bacteria. The organism could be sensed by specific receptors, such as Toll-like Receptors (TLR) or Retinoid-Inducible Gene-1 (RIG-1). These sensors can then initiate a cascade of chemical and physiological responses in the immune system by secreting cytokines and chemokines, such as interferon and IL-8. The chemokines will attract immune cells, such as macrophages and granulocytes, that will further secrete cytokines and chemokines, and may also initiate an inflammatory reaction that may be involve prostaglandins and leukotrienes. As a defensive measure the cascade may unleash a respiratory burst of highly oxidizing species, such as peroxides and superoxide radicals, which can destroy potential pathogens, but may also cause substantial tissue injury.

In some settings, affirmative steps may be taken (before, during, and/or after a surgical procedure) to block or restrict changes or expressions of biomarkers that might otherwise occur as a result of a surgical procedure. Thus, these affirmative steps may alter or even dictate the sequence or characteristics of the "biomarker cascades" referred to above. For example, if the biomarker cascade involves an extreme respiratory burst of free radicals, then therapeutic treatment with antioxidants may be beneficial. If substantial inflammatory biomarkers are observed, then corticosteroids may be applied to limit the immune response. In chronic wound healing, m-RNA blocking strategies for TGF-beta or other biomarkers may prevent excessive granulation tissue and keloid formation. Other examples of how preparatory steps, therapeutic steps, or other kinds of steps may be taken in response to biomarker expressions are described elsewhere herein; while still other examples will be apparent to those of ordinary skill in the art in view of the teachings herein.

There are numerous methods of improving wound healing once injury to the tissue has occurred. Some such approaches involve nutritional and/or therapeutic treatments. For instance, U.S. Pat. No. 6,187,743, entitled "Composition and Method for Enhancing Wound Healing," issued Feb. 13, 2001, the disclosure of which is incorporated by reference herein, discloses compositions and methods used to treat a pre-existing wound; but does not disclose how to minimize the trauma from an iatrogenic wound, nor does it disclose relevant biomarkers that may be used to assess the trauma inflicted by surgical devices or the design and selection of surgical instruments used for cutting the tissue.

Methods have also been described wherein biomarkers are used to assess wound healing. Examples include U.S. Pub. No. 2004/0038292, entitled "Wound Healing Biomarkers," published Feb. 26, 2004, now abandoned, the disclosure of which is incorporated by reference herein; and U.S. Pub. No. 2005/0287535, entitled "Biomarkers for Wound Healing," published Dec. 29, 2005, now U.S. Pat. No. 8,034,553, issued Oct. 11, 2011, the disclosure of which is incorporated by reference herein. However, these applications did not describe the use of biomarkers in the context of real-time surgical assessments and/or as a guide in determining the best device to be used for a particular procedure where a cut to the tissue is necessitated.

B. Monitoring of Biomarkers

Examples described herein are based on the analysis of biomarkers (e.g., genes and proteins), the expression of which is upregulated or downregulated during a wound healing response, occurring with or without the inflammatory response and usually occurring in healing wounds. It is believed that the presence (or absence) of certain biomarkers may be used to monitor the progression of wound healing; and in some cases these biomarkers may be monitored in real time, during the surgical procedure. Examples described herein also provide markers that are useful in monitoring, for example, the state of healing of a wound. These markers may be used more generally for monitoring diseases or disorders characterized by impaired or by excessive wound healing. In addition, examples described herein provide markers for wound inflammation. These markers may be useful in the clinical assessment of the progress of healing and may be used to aid in the selection of the appropriate therapeutic intervention.

As described elsewhere herein, various proteins may serve as useful biomarkers. Since protein is manufactured based on instructions from mRNA, the appearance of protein lags behind that of the mRNA. Furthermore, there are other regulatory processes involved, so that a high level of mRNA does not necessarily correlate with a high level of its corresponding protein. Therefore it may be useful to measure mRNA levels, protein levels, or both. It should also be understood that different biomarkers may be expressed during different time frames in response to a wound or other biological condition. For instance, some biomarkers may be expressed immediately, others within hours, others within a week, others within several weeks, etc. Thus, in some instances, it may be useful to tailor biomarker monitoring based on timing, such as to only look for certain biomarkers during certain time frames. Similarly, selections of biomarkers for monitoring may be based on factors such as the location in the patient's anatomy where the wound has been or will be inflicted, the type of device that is inflicting the wound, the vehicle used to convey the biomarkers to the monitoring instrument, and/or various other factors.

The expression levels of biomarkers may be quantified by any assay available to one skilled in the art and/or using any other suitable techniques as will be apparent to those of ordinary skill in the art in view of the teachings herein. For instance, a measurement may be taken detecting the presence or absence of the biomarkers(s), quantifying the amount of marker(s), and qualifying the type of biomarker. The biomarker measurement may be made for instance, by using a biochip array. In some examples, the biochip array is an antibody chip array, tissue chip array, protein chip array, or a peptide chip array. In some other examples, the biochip array is a nucleic acid array. In still other examples, at least one biomarker capture reagent is immobilized on the biochip array. In still other examples, the protein biomarkers are measured by immunoassay. In addition, biomarker expression levels may be quantified by a hybridization assay of RNA obtained from the wound tissue sample to a probe complementary to a particular receptor, for instance, IL8 receptor. In other examples, the expression levels may also be quantified by amplification of wound tissue sample RNA. The expression levels may also be quantified by immunoassay of the wound tissue sample using an antibody directed against a particular receptor, for example, the IL8 receptor.

Another tool that may be useful in identifying biomarkers generated in-situ during surgery is mass spectrometry, which may quickly identify any molecule in a sample by measuring its mass and charge. More specifically, DESI (desorption electrospray ionization) may be used, whereby a sample collector may work in open air and leave tissue intact. In some versions, DESI may be used with commercial mass spectrometers and may monitor tissues in real-time during the surgery. This technique may provide one with the ability to identify a broad spectrum of molecules in a tissue or even inside a cell and may give an intimately detailed picture the activities and disease state of the tissue and/or cells in question during surgery.

Molecular cell bioengineering may also be used in monitoring and identifying biomarkers that are generated in-situ during surgery. This method uses computational models for receptor regulation of cell function by exploiting techniques of molecular biology to alter parameters characterizing receptor or ligand properties in well-characterized cell systems. Molecular cell bioengineering develops a quantitative understanding of cell function in terms of fundamental molecular properties and includes important aspects of receptor-mediated regulation of mammalian blood and tissue cell behavioral functions such as proliferation, adhesion, migration, differentiation, and death. Quantitative experimental assays monitoring for the presence or absence of key biomarkers may be used to measure cell functions, receptor/ligand interaction parameters, and signaling network dynamics during surgery.

The presence (or absence) of certain biomarkers may be used to adjust the monitoring, administration, and/or planning of particular therapeutics or actives during a surgical procedure. "Active" in this sense may include a variety of things, including but not limited to gene therapies, stem cell treatments, conventional pharmaceutical drugs, etc. The analysis of these biomarkers may also be evaluated in real-time in order to adjust the administration of any active that may be needed and/or to alter the surgical parameters. In addition, through the monitoring of the biomarkers, examples described herein may provide a method of identifying an active (or actives) useful for treating the wound tissue during the surgical procedure as well as after the procedure to aid in reduced healing time for the patient. Biomarkers may also be used to gauge the relative damage of different surgical instruments that are used to make the incisions during the surgery. In addition, the sensitivity of this method may be sufficient to not only monitor the damage produced by a particular surgical device, but to also distinguish between different surgical devices and the desirability of one device versus another for a particular procedure. The differences observed can then be used to further improve the efficiency of the surgical device, and in turn, lessen the patient's trauma.

In some versions, one or more elements of a biomarker monitoring apparatus are incorporated into a wound dressing. For instance, the wound dressing may include a one or more biomarker measuring devices that contact the wound while the wound dressing still serves a purpose as a wound dressing. Such an apparatus may allow clinicians to interrogate the one or more biomarker measuring devices, either upon removal of the wound dressing or without requiring the wound dressing to be removed.

A merely illustrative example of a process that may be carried out to monitor biomarkers and use biomarker data is illustrated in FIG. 1. As shown in block (10), a mist at a wound site is evacuated to draw biomarkers from the patient for processing. In some versions, including some of those described in greater detail below, such a mist is produced by a harmonic surgical instrument that is used to create the wound as part of a surgical procedure. Those of ordinary skill in the art will appreciate that such a mist or smoke may be produced anyway as a matter of course during surgical use of a conventional harmonic device, such that the process illustrated in FIG. 1 simply draws off at least part of that expected (and otherwise wasted) mist in order to process biomarkers contained in the mist. As will also be described in greater detail below, such a mist may be evacuated using suction created by a vacuum source that is in fluid communication with a port at or near the end effector of the harmonic surgical instrument.

Continuing to block (20) of FIG. 1, the evacuated mist is filtered and diluted with saline or some other fluid medium. As part of the filtering represented by block (20), the mist may be sieved ultrasonically, electrostatically, both, and/or otherwise filtered. Optionally, biomarkers in the mist may be cleaved with one or more enzymes as shown in block (30) of FIG. 1. Suitable situations in which such cleaving may be desirable, as well as suitable enzymes that may be used in this part of the process, will be apparent to those of ordinary skill in the art in view of the teachings herein. After cleaving by enzymes, the mist with biomarkers is flowed over a sensor as shown in block (40) of FIG. 1. Various examples of suitable sensors that may be used at this stage are described elsewhere herein, while still other examples of suitable sensors will be apparent to those of ordinary skill in the art in view of the teachings herein. It should also be understood that various types of sensors may be used in any given process, such as by using different sensors to pick up different biomarkers. For instance, any one or more biomarkers referred to herein, including but not limited to genomes or proteomes, may be picked up by one or more sensors as part of the process shown in FIG. 1, among other biomarkers. As shown in block (50), the next stage of the process in the present example is to obtain one or more readings from the sensor(s) and process such reading(s) in one or more selected ways.

The process illustrated in FIG. 1 shows several options for actions that may be taken in response to readings obtained from a biomarker sensor. For instance, as shown in block (60), a particular therapy (e.g., therapeutic agent, therapeutic process, etc.) may be selected and administered based on readings obtained from a biomarker sensor. Various suitable ways in which such therapy may be selected and administered based on biomarker data are described elsewhere herein, while still other examples of suitable ways in which such therapy may be selected and administered based on biomarker data will be apparent to those of ordinary skill in the art in view of the teachings herein. As shown in block (70), a particular device (e.g., surgical instrument, medical implant, wound dressing, etc.) may be selected based on readings obtained from a biomarker sensor. Again, various suitable ways in which a device may be selected based on biomarker data are described elsewhere herein, while still other examples of suitable ways in which a device may be selected based on biomarker data will be apparent to those of ordinary skill in the art in view of the teachings herein. As shown in block (80), one or more operating parameters of a device (e.g., surgical instrument, medical implant, wound dressing, etc.) may be adjusted based on readings obtained from a biomarker sensor. Again, various suitable ways in which operating parameters of a device may be adjusted based on biomarker data are described elsewhere herein, while still other examples of suitable ways in which operating parameters of a device may be adjusted based on biomarker data will be apparent to those of ordinary skill in the art in view of the teachings herein. As shown in block (90), the technique by which a device (e.g., surgical instrument, medical implant, wound dressing, etc.) is used may also be adjusted based on readings from a biomarker sensor. Yet again, various suitable ways in which the technique by which a device is used may be adjusted based on biomarker data are described elsewhere herein, while still other examples of suitable ways in which the technique by which a device is used may be adjusted based on biomarker data will be apparent to those of ordinary skill in the art in view of the teachings herein.

It should be understood that the reactions to biomarker data shown in blocks (60, 70, 80, 90) of FIG. 1 are merely illustrative examples. Various other types of reactions to biomarker data may be taken in addition to or in lieu of any of those shown in blocks (60, 70, 80, 90). Similarly, it should be understood that the process shown in FIG. 1 is merely one example. The process shown in FIG. 1 may be varied in numerous ways, including but not limited to supplementing the process with steps not shown in FIG. 1, substituting one or more steps shown in FIG. 1 with one or more other steps, omitting one or more of the steps shown in FIG. 1, etc. Additional examples of how biomarkers may be detected, quantified, qualified, etc. will be described in greater detail below (e.g., section V.A., below), while various other examples will be apparent to those of ordinary skill in the art in view of the teachings herein. Similarly, various ways in which biomarker data may be used will be described in greater detail below (e.g., section V.B. through section V. C., below), while various other examples will be apparent to those of ordinary skill in the art in view of the teachings herein.

C. Examples of Biomarkers

Specific examples of biomarkers that may be detected/monitored/used/etc. in accordance with the teachings herein are given in Tables 1-4. Table 1 provides a list of genes that are upregulated after the trauma of surgery. These genes or their associated proteins may be used to determine the degree of trauma resulting from a particular medical device. An increase in the level of gene expression or the amount of its associated protein indicates greater tissue damage from the medical device. It should be understood that a relatively high amount of tissue damage may be due to properties of the medical device itself, the way in which the medical device was used, and/or a particular susceptibility of the patient in/on which the medical device was used, among other potential factors. In some settings, a lower level of gene expression or the amount of its associated protein can therefore be used to identify a less traumatic, hence "superior" surgical cutting instrument and/or technique. In addition or in the alternative, a higher level of gene expression or the amount of its associated protein may be used to identify a higher susceptibility of a particular patient to tissue damage; and such information may thus be used to modify the selection of a medical device for use on the patient, to modify the way in which a medical device is used in/on the patient, and/or to select the type/amount of one or more agents to be administered to the patient at the wound site.

TABLE 1

Upregulated Genes

| No. | Acronym | Gene description |
|---|---|---|
| 1 | CXCL6 | Granulocyte chemotactic protein 2 (GCP-2) |
| 2 | IL8 | Interleukin-8 |
| 3 | ARG1 | Arginase 1 |
| 4 | SERPINB2 | Plasminogen activator inhibitor-2 (PAI-2) |
| 5 | CXCL2 | Macrophage inflammatory protein-2-alpha (MIP2-alpha) |
| 6 | FAM81B | Family with sequence similarity 81, member B |
| 7 | PPBP | Platelet basic protein (CXCL7) |
| 8 | PF4 | Platelet factor 4 (CXCL4) |
| 9 | GPR68 | Sphingosylphosphorylcholine receptor |
| 10 | TNC | Tenascin |
| 11 | MARCO | Macrophage receptor with collagenous structure |
| 12 | PRSS35 | Protease, serine, 35 |
| 13 | CYP1B1 | Cytochrome P450 1B1 |
| 14 | CA12 | Carbonic anhydrase XII |
| 15 | IL6 | Interleukin-6 |
| 16 | ALDH9A1 | Aldehyde dehydrogenase 9 family, member A1 |
| 17 | SDS | L-serine dehydratase |
| 18 | IL1RN | Interleukin-1 receptor antagonist protein |
| 19 | PTX3 | Pentaxin-related protein |
| 20 | SELE | E-selectin |
| 21 | ADFP | Adipophilin |
| 22 | TIMP1 | Metalloproteinase inhibitor 1 |
| 23 | Q6ZUM6 | Dynein, cytoplasmic, heavy polypeptide 2 |
| 24 | IDH2 | Isocitrate dehydrogenase |
| 25 | SERPINE1 | Plasminogen activator inhibitor-1 |
| 26 | ANGPTL4 | Angiopoietin-related protein 4 |
| 27 | CYR61 | Cysteine-rich, angiogenic inducer, 61 |
| 28 | CXCL14 | Small inducible cytokine B14 |
| 29 | MMP1 | Matrix metalloproteinase-1 |
| 30 | NPM3 | Nucleoplasmin 3 |
| 31 | CYP3A4 | Cytochrome P450 3A4 |
| 32 | HLA-DRB4 | MHC class I antigen DRB1*4 |
| 33 | FOS | Cellular oncogene fos |
| 34 | AMELX | Amelogenin, X isoform |
| 35 | FRYL | FRY-like |
| 36 | RRM2 | Ribonucleoside-diphosphate reductase M2 chain |
| 37 | CDKAL1 | CDK5 regulatory subunit associated protein 1 |
| 38 | S100A9 | Calgranulin B |
| 39 | PCP4L1 | Purkinje cell protein 4 like 1 |
| 40 | SFRP2 | Secreted frizzled-related protein 2 |
| 41 | THBS1 | Thrombospondin 1 |
| 42 | AQN1 | Spermadhesin |
| 43 | TCA_HUMAN | T-cell receptor alpha chain C region |
| 44 | HMOX1 | Heme oxygenase 1 |
| 45 | TMEM49 | Transmembrane protein 49 |
| 46 | FZD1 | Frizzled 1 |
| 47 | KRT1 | Keratin, type II cytoskeletal 1 |
| 48 | CCNB1 | G2/mitotic-specific cyclin B1 |
| 49 | LIF | Leukemia inhibitory factor precursor |
| 50 | CCL2 | Monocyte chemotactic protein 1 (MCP-1) |
| 51 | ACTG2 | Actin, gamma-enteric smooth muscle |
| 52 | MIG6_HUMAN | Mitogen-inducible gene 6 protein |
| 53 | SLC16A3 | Monocarboxylate transporter 4 |
| 54 | MMP7 | Matrilysin |
| 55 | MAP3K8 | Mitogen-activated protein kinase kinase kinase 8 |
| 56 | OLFM3 | Olfactomedin 3 |
| 57 | KCNH1 | Potassium voltage-gated channel subfamily H member 1 |
| 58 | RIMS1 | Regulating synaptic membrane exocytosis protein 1 |
| 59 | CCDC99 | Coiled-coil domain containing 99 |
| 60 | SMARCAL1 | SWI/SNF-related matrix-associated actin-dependent regulator of chromatin a-like 1 |
| 61 | ARL7 | ADP-ribosylation factor-like protein 7 |
| 62 | CKAP4 | Cytoskeleton-associated protein 4 |
| 63 | KIAA0101 | HCV NS5A-transactivated protein 9 |
| 64 | NP_077001 | XTP3-transactivated protein A |
| 65 | PLS1 | Intestine-specific plastin |

TABLE 1-continued

Upregulated Genes

| No. | Acronym | Gene description |
|---|---|---|
| 66 | SLC2A14 | Glucose transporter 14 |
| 67 | TNFAIP1 | Tumor necrosis factor, alpha-induced protein 1, endothelial |
| 68 | CLECSF5 | C-type lectin, superfamily member 5 |
| 69 | BUB1 | Mitotic checkpoint serine/threonine-protein kinase |
| 70 | CSRP2 | Cysteine and glycine-rich protein 2 |
| 71 | SKA1 | Spindle and KT associated 1 |
| 72 | DLG7 | Discs, large homolog 7 |
| 73 | BIRC5 | Apoptosis inhibitor survivin |
| 74 | LIPG | Endothelial lipase |
| 75 | CENPE | Centromeric protein E |
| 76 | MCAM | Cell surface glycoprotein MUC18 |
| 77 | POLQ | DNA polymerase theta |
| 78 | UCK2 | Uridine-cytidine kinase 2 |
| 79 | CTSL | Cathepsin L |
| 80 | HPSE | Heparanase |
| 81 | SHCBP1 | SHC SH2-domain binding protein 1 |
| 82 | HAS2 | Hyaluronan synthase 2 |
| 83 | STK6 | Serine/threonine-protein kinase 6 |
| 84 | ETV6 | Transcription factor ETV6 |
| 85 | KRT17 | Keratin, type I cytoskeletal 17 |
| 86 | KRT5 | Keratin, type II cytoskeletal 5 |
| 87 | KRTAP3-3 | Keratin associated protein 3-3 |
| 88 | SCGB2A1 | Mammaglobin B (Mammaglobin 2) |
| 89 | CBR1 | Carbonyl reductase [NADPH] 1 |
| 90 | KRTAP3-1 | Keratin associated protein 3-1 |
| 91 | KRT14 | Keratin, type I cytoskeletal 14 |
| 92 | LTF | Lactotransferrin (Lactoferrin) |
| 93 | CHIA | Acidic mammalian chitinase |
| 94 | KRTHA2 | Keratin, type I cuticular HA2 |
| 95 | TDO2 | Tryptophan 2,3-dioxygenase |
| 96 | KRT10 | Keratin, type I cytoskeletal 10 |
| 97 | KRTAP1-5 | keratin associated protein 1.5 |
| 98 | KRTAP2-4 | keratin associated protein 2-4 |
| 99 | DSP | Desmoplakin |
| 100 | SFN | 14-3-3 protein sigma (Stratifin) |
| 101 | AP1S3 | Adapter-related protein complex 1 sigma 1C |
| 102 | PERP | PERP, TP53 apoptosis effector |

Although either the gene mRNA or the associated proteins may be used, in some cases it may be preferable to use the mRNA because the level of the proteins on this list may be at very low levels, and hence may be difficult to assay accurately. Of course, certain assay techniques may be suitable for accurately assaying very low levels of proteins. It should also be understood that the listing of Table 1 is not intended to be exhaustive, as other genes may be upregulated after the trauma of surgery.

Table 2 provides a list of genes that are downregulated after the trauma of surgery. These genes or their associated proteins may be used to determine the degree of trauma resulting from the use of a particular medical device in making an incision. A decrease in the level of gene expression or the amount of its associated protein indicates greater tissue damage from the medical device. A less depressed level of gene expression or the amount of its associated protein can therefore be used to identify a less traumatic, and hence less damaging surgical cutting instrument and/or technique. In addition or in the alternative, a less depressed level of gene expression or the amount of its associated protein may be used to identify a reduced susceptibility of a particular patient to tissue damage; and such information may thus be used to modify the selection of a medical device for use on the patient, to modify the way in which a medical device is used in/on the patient, and/or to select the type/amount of one or more agents to be administered to the patient at the wound site.

TABLE 2

Downregulated Genes

| No. | Acronym | Gene description |
|---|---|---|
| 1 | PON3 | Serum paraoxonase/lactonase 3 |
| 2 | MYOC | Myocilin |
| 3 | AGT | Angiotensinogen |
| 4 | CA3 | Carbonic anhydrase III |
| 5 | EGF | Pro-epidermal growth factor precursor |
| 6 | CYP2A13 | Cytochrome P450 2A13 |
| 7 | FTHFD | 10-formyltetrahydrofolate dehydrogenase |
| 8 | PPP1R1A | Protein phosphatase inhibitor 1 |
| 9 | ELOVL6 | ELOVL family member 6, elongation of long chain fatty acids |
| 10 | KERA | Keratocan |
| 11 | BRUNOL4 | Bruno-like 4, RNA binding protein |
| 12 | FASN | Fatty acid synthase |
| 13 | KCNS1 | Potassium voltage-gated channel subfamily S member 1 |
| 14 | CILP | Cartilage intermediate layer protein |
| 15 | AUTS2 | Autism susceptibility gene 2 protein |
| 16 | CDO1 | Cysteine dioxygenase type I |
| 17 | GAP43 | Neuromodulin |
| 18 | ALDOC | Fructose-bisphosphate aldolase C |
| 19 | LEP | Leptin |
| 20 | DDO | D-aspartate oxidase |
| 21 | CYP4F3 | Cytochrome P450 4F3 |
| 22 | SCD | Acyl-CoA desaturase |
| 23 | SLC36A2 | Solute carrier family 36, member 2 |
| 24 | GPR120 | G protein-coupled receptor 120 |
| 25 | ME1 | NADP-dependent malic enzyme |
| 26 | TMEFF2 | Transmembrane protein with EGF-like and two follistatin-like domains |
| 27 | KNTC1 | Kinetochore-associated protein 1 |
| 28 | CES3 | Liver carboxylesterase 1 |
| 29 | TTC36 | Tetratricopeptide repeat domain 36 |
| 30 | DAXX | Death domain-associated protein 6 |
| 31 | RBP4 | Plasma retinol-binding protein |
| 32 | LPL | Lipoprotein lipase |
| 33 | PGLYRP2 | N-acetylmuramoyl-L-alanine amidase |
| 34 | ADHFE1 | Alcohol dehydrogenase, iron containing, 1 |
| 35 | LNP | Lunapark |
| 36 | RNF180 | Ring finger protein 180 |
| 37 | GSN | Gelsolin |
| 38 | G0S2 | Lymphocyte G0/G1 switch protein 2 |
| 39 | APCDD1 | Adenomatosis polyposis coli down-regulated 1 |
| 40 | PNPLA7 | Patatin-like phospholipase domain containing 7 |
| 41 | CYP4B1 | Cytochrome P450 4B1 |
| 42 | DGAT2 | Diacylglycerol O-acyltransferase homolog 2 |
| 43 | HSPA12A | Heat shock 70 kDa protein 12A |
| 44 | PDE5A | cGMP-specific 3',5'-cyclic phosphodiesterase |
| 45 | DGKB | Diacylglycerol kinase, beta |
| 46 | SNTB1 | Beta-1-syntrophin |
| 47 | PPAP2A | Lipid phosphate phosphohydrolase 1 |
| 48 | PAQR6 | Progestin and adipoQ receptor family member VI isoform 1 |
| 49 | ADR2 | Adiponectin receptor protein 2 |
| 50 | ATP6V0A4 | Vacuolar proton translocating ATPase 116 kDa subunit a isoform 4 |
| 51 | ACAS2 | Acetyl-coenzyme A synthetase, cytoplasmic |
| 52 | ACACA | Acetyl-CoA carboxylase 1 |
| 53 | COL21A1 | Alpha 1 type XXI collagen |
| 54 | MAL2 | MAL2 protein |
| 55 | SAL1 | Salivary lipocalin |
| 56 | PPL | Periplakin |
| 57 | ADORA1 | Adenosine A1 receptor |
| 58 | DRR1 | DRR1 protein |
| 59 | GRPEL2 | GrpE protein homolog 2, mitochondrial |
| 60 | FXYD1 | Phospholemman |
| 61 | LTBP4 | Latent transforming growth factor beta binding protein 4 |
| 62 | ANK3 | Ankyrin 3 |
| 63 | ACDC | Adiponectin |
| 64 | OXCT1 | Succinyl-CoA:3-ketoacid-coenzyme A transferase 1, mitochondrial |
| 65 | TNA | Tetranectin |
| 66 | CNTN1 | Contactin |
| 67 | PSAT1 | Phosphoserine aminotransferase |
| 68 | MUM1L1 | Melanoma associated antigen (mutated) 1-like 1 |
| 69 | PC | Pyruvate carboxylase, mitochondrial |
| 70 | MFAP5 | Microfibrillar-associated protein 5 precursor |
| 71 | NTRK2 | BDNF/NT-3 growth factors receptor |
| 72 | OPCML | Opioid binding protein/cell adhesion molecule |
| 73 | CITED1 | Cbp/p300-interacting transactivator 1 |
| 74 | BCHE | Cholinesterase |
| 75 | PPP1R1B | Dopamine- and cAMP-regulated neuronal phosphoprotein |
| 76 | ARL4A | ADP-ribosylation factor-like protein 4A |
| 77 | LPIN1 | Lipin 1 |
| 78 | NAALADL2 | N-acetylated alpha-linked acidic dipeptidase 2 |
| 79 | ADAMTS19 | A disintegrin and metalloproteinase with thrombospondin motifs 19 |
| 80 | Q8WTR7 | Zinc finger protein 473 |
| 81 | PLAC1 | Placenta-specific 1 |
| 82 | ZFPM2 | Zinc finger protein ZFPM2 |
| 83 | LHCGR | Lutropin-choriogonadotropic hormone receptor |
| 84 | EFHC2 | EF-hand domain (C-terminal) containing 2 |
| 85 | ADAMTSL3 | A disintegrin-like and metalloprotease domain with thrombospondin type I motifs-like 3 |
| 86 | CXCL9 | Gamma interferon induced monokine |
| 87 | GPD1 | Glycerol-3-phosphate dehydrogenase [NAD+], cytoplasmic |
| 88 | SGK2 | Serine/threonine-protein kinase |
| 89 | ZC3H11A | Zinc finger CCCH domain-containing protein 11A |
| 90 | CRB1 | Crumbs protein homolog 1 |
| 91 | F5 | Coagulation factor V |
| 92 | RBED1 | RNA binding motif and ELMO domain 1 |
| 93 | CAMK2N1 | calcium/calmodulin-dependent protein kinase II |
| 94 | CABC1 | Chaperone-activity of bc1 complex-like, mitochondrial |
| 95 | MORF4L1 | Transcription factor-like protein MRG15 |
| 96 | SPARCL1 | SPARC-like protein 1 |
| 97 | HPGD | 15-hydroxyprostaglandin dehydrogenase |
| 98 | HLF | Hepatic leukemia factor |
| 99 | PROM1 | Prominin 1 |
| 100 | LPIN1 | Lipin 1 |
| 101 | ISLR | Immunoglobulin superfamily containing leucine-rich repeat |
| 102 | FMO1 | Dimethylaniline monooxygenase |
| 103 | SGCD | Delta-sarcoglycan |
| 104 | UNC93A | UNC-93 homolog A |
| 105 | PSPHL | L-3-phosphoserine phosphatase |
| 106 | EZH2 | Enhancer of zeste homolog 2 |
| 107 | CASC1 | Cancer susceptibility candidate 1 |
| 108 | COL14A1 | Collagen, Type XIV, Alpha-1 |
| 109 | RUFY1 | RUN and FYVE domain containing protein 1 |
| 110 | RBP1 | Retinol-binding protein I, cellular |
| 111 | THSD2 | Thrombospondin, type I, domain containing 2 |
| 112 | GPT | Alanine aminotransferase |
| 113 | SLC27A6 | Solute carrier family 27 (fatty acid transporter), member 6 |
| 114 | SETBP1 | SET-binding protein |
| 115 | ME1 | NADP-dependent malic enzyme |
| 116 | FASN | Fatty acid synthase |

Although either the gene mRNA or the associated proteins may be used, in some cases it may be preferable to use the mRNA because the level of the proteins on this list may be at very low levels, and hence may be difficult to assay accurately. Again, though, certain assay techniques may be suitable for accurately assaying very low levels of proteins. It should also be understood that the listing of Table 2 is not intended to be exhaustive, as other genes may be downregulated after the trauma of surgery.

Table 3 provides a listing of proteins that are increased after the trauma of surgery. These proteins may be used to determine the degree of trauma resulting from the use of a particular medical device in making an incision. An increase in the level of the protein indicates greater tissue damage from the medical device. In addition or in the alternative, an increase in the level of the protein may be used to identify a higher susceptibility of a particular patient to tissue damage; and such information may thus be used to modify the selection of a medical device for use on the patient, to modify the way in which a medical device is used in/on the patient, and/or to select the type/amount of one or more agents to be administered to the patient at the wound site. A lower level of protein may be used to identify a less traumatic, hence less damaging surgical cutting instrument.

The level of these proteins may in general be more useful than the level of the corresponding mRNA because these protein levels may have been induced by direct effect of surgery rather than by upregulation of the associated gene. It should also be understood that the listing of Table 3 is not intended to be exhaustive, as other proteins may be increased after the trauma of surgery.

TABLE 3

Upregulated Proteins

| No. | Acronym | Protein |
|---|---|---|
| 1 | CSTB | cystatin B protein |
| 2 | CTNNA1 | Isoform 2 of Catenin alpha-1 |
| 3 | MAN2B1 | lysosomal alpha-mannosidase |
| 4 | HTRA1 | protease serine 11 (IGF binding) |
| 5 | S100A12 | Protein S100-A12 |
| 6 | TKT | transketolase |
| 7 | ANPEP | Aminopeptidase N |
| 8 | PTPRC | protein tyrosine phosphatase, receptor type, C |
| 9 | VPS29 | Vacuolar protein sorting-associated protein 29 |
| 10 | GPNMB | glycoprotein NMB |
| 11 | PABPC1 | similar to Polyadenylate-binding protein 1 (Poly(A)-binding protein 1) (PABP 1) |
| 12 | ATP6V1B2 | V-type proton ATPase subunit B, brain isoform |
| 13 | SFRS1 | splicing factor arginine/serine-rich 1 |
| 14 | TCIRG1 | T-cell, immune regulator 1, ATPase, H+ transporting, lysosomal V0 subunit A3 |
| 15 | CTSD | cathepsin D |
| 16 | COL3A1 | Isoform 1 of Collagen alpha-1(III) chain |
| 17 | FKBP11 | peptidyl-prolyl cis-trans isomerase FKBP11 |
| 18 | ITGB2 | CD18 |
| 19 | IDH1 | Isocitrate dehydrogenase [NADP] cytoplasmic |
| 20 | DHX9; DHX9 | ATP-dependent RNA helicase A |
| 21 | ITGAL | integrin alpha-L precursor |
| 22 | FLNA | Isoform 1 of Filamin-A |
| 23 | ICA; PICA | porcine inhibitor of carbonic anhydrase precursor |
| 24 | SLC25A6 | solute carrier family 25 member 6 |
| 25 | FLNC | Filamin-C |
| 26 | TLN1 | talin 1 |
| 27 | ACTR2 | actin-related protein 2-like protein |
| 28 | RPL26L1 | ribosomal protein L26-like 1 |
| 29 | ATP6V1E1 | similar to Vacuolar proton pump subunit E 1 (V-ATPase subunit E 1) (V-ATPase 31 kDa subunit) (P31) |
| 30 | GUCY1B3 | soluble guanylate cyclase 1 beta 3 |
| 31 | MYH14 | myosin, heavy chain 14 isoform 3 |
| 32 | GENSCAN00000034603 | chromosome:Sscrofa9:6:38101539:38110768:-1 transcript:GENSCAN00000034603 |
| 33 | TNC | tenascin C |
| 34 | EIF4A1 | eukaryotic initiation factor 4A-I |
| 35 | CLTC | clathrin heavy chain |
| 36 | ARPC1B | actin related protein 2/3 complex subunit 1B |
| 37 | ANXA1 | similar to annexin 1, partial |
| 38 | BGN | biglycan |
| 39 | VIM | vimentin |
| 40 | MYH10 | myosin, heavy chain 10, non-muscle isoform 1 |
| 41 | CKAP4 | Isoform 1 of Cytoskeleton-associated protein 4 |
| 42 | LGALS3 | lectin galactoside-binding soluble 3 |
| 43 | NPG4 | Antibacterial peptide PMAP-37 |
| 44 | LRP1 | low density lipoprotein receptor-related protein 1 |
| 45 | C3 | complement component C3 |
| 46 | GNAI2 | guanine nucleotide-binding protein G(i) subunit alpha-2 |
| 47 | P4HA1 | prolyl 4-hydroxylase subunit alpha-1 |
| 48 | GENSCAN00000016869 | chromosome:Sscrofa9:14:110127633:110157746:1 transcript:GENSCAN00000016869 |
| 49 | LAMP-1 | lysosome-associated membrane glycoprotein 1 |
| 50 | HBA | Hemoglobin subunit alpha |
| 51 | DES | muscle-specific intermediate filament desmin |
| 52 | ACTN1 | alpha-actinin-1 |
| 53 | HBB | Hemoglobin subunit beta |
| 54 | SCARB2 | lysosome membrane protein 2 |
| 55 | CD48 | CD48 antigen |
| 56 | GRB2 | growth factor receptor bound protein 2 |
| 57 | MYH9 | myosin-9 |
| 58 | GLIPR2 | Golgi-associated plant pathogenesis-related protein 1 |
| 59 | CAPZB | F-actin capping protein beta subunit |
| 60 | CAPN2 | calpain 2 |
| 61 | RPL4 | 60S ribosomal protein L4 |

TABLE 3-continued

Upregulated Proteins

| No. | Acronym | Protein |
|---|---|---|
| 62 | RAC2 | Ras-related C3 botulinum toxin substrate 2 |
| 63 | CRP | C-reactive protein |
| 64 | PTBP1 | polypyrimidine tract-binding protein |
| 65 | CORO1C | similar to Coronin-1C (Coronin-3) (hCRNN4) |
| 66 | HNRNPA1 | heterogeneous nuclear ribonucleoprotein A1 |
| 67 | SFRS7 | Splicing factor, arginine/serine-rich 7 |
| 68 | CLU | complement cytolysis inhibitor |
| 69 | ANXA2 | Annexin A2 |
| 70 | Rrbp1 | similar to ribosome receptor |
| 71 | Pzp | similar to Alpha-2-macroglobulin precursor (Pregnancy zone protein) (Alpha-2-M) |
| 72 | GENSCAN00000037410 | chromosome:Sscrofa9:2:7434734:7455121:1 transcript:GENSCAN00000037410 |
| 73 | AP2B1 | Isoform 2 of AP-2 complex subunit beta |
| 74 | PLG | plasminogen precursor |
| 75 | PSME1 | proteasome activator 28 alpha subunit |
| 76 | COL1A1 | Collagen alpha-1(I) chain |
| 77 | ASPN | asporin precursor |
| 78 | HNRNPH1 | Heterogeneous nuclear ribonucleoprotein H |
| 79 | A1BG | alpha-1-B glycoprotein |
| 80 | AIMP1 | small inducible cytokine subfamily E member 1 |
| 81 | EEF2 | Elongation factor 2 |
| 82 | AP1B1 | similar to AP1B1 |
| 83 | MYL6 | myosin light polypeptide 6 |
| 84 | GENSCAN00000035285 | chromosome:Sscrofa9:9:116512127:116526965:1 transcript:GENSCAN00000035285 |
| 85 | EEF1A1 | eukaryotic translation elongation factor 1 alpha |
| 86 | ARPC2 | actin related protein 2/3 complex subunit 2 |
| 87 | ANXA4 | annexin A4 |
| 88 | FMOD | Fibromodulin |
| 89 | CLINT1 | Clathrin interactor 1 |
| 90 | S100A10 | similar to S100 calcium binding protein A10 |
| 91 | PYCR1 | Pyrroline-5-carboxylate reductase |
| 92 | APOA1 | Apolipoprotein A-I |
| 93 | CTSB | cathepsin B |
| 94 | ACTB | Actin, cytoplasmic 1 |
| 95 | HDLBP | HDL binding protein |
| 96 | HNRNPA2B1 | Isoform B1 of Heterogeneous nuclear ribonucleoproteins A2/B1 |
| 97 | COX6A1 | cytochrome c oxidase subunit VIa polypeptide 1 |
| 98 | SQRDL | sulfide:quinone oxidoreductase, mitochondrial |
| 99 | HK1 | similar to hexokinase 1 |
| 100 | CAPZA1 | F-actin capping protein subunit alpha 1 |
| 101 | APOH | beta-2-glycoprotein 1 precursor |
| 102 | PPIB | similar to peptidylprolyl isomerase B |
| 103 | CAP1 | 56 kda actin-sequestering protein, ASP-56 = peptide T26/27 |
| 104 | S100A4 | similar to Protein S100-A4 (S100 calcium-binding protein A4) (Metastasin) (Protein Mts1) (Placental calcium-binding protein) (Calvasculin) isoform 2 |
| 105 | NAP1L4 | Nucleosome assembly protein 1-like 1 |
| 106 | VAT1 | Synaptic vesicle membrane protein VAT-1 homolog |
| 107 | MSN | Moesin |
| 108 | HNRNPC | Isoform C2 of Heterogeneous nuclear ribonucleoproteins C1/C2 |
| 109 | SCP2 | sterol carrier protein 2 |
| 110 | GENSCAN00000042293 | chromosome: Sscrofa9:14:49771686:49783007:1 transcript:GENSCAN00000042293 |
| 111 | HSP90; HSP90AA1 | heat shock protein HSP 90-alpha |
| 112 | FERMT3 | fermitin family homolog 3 |
| 113 | ITGB3 | glycoprotein GPIIIa |
| 114 | NUCB1 | nucleobindin 1 |
| 115 | COL6A3 | collagen, type VI, alpha 3 |
| 116 | COPB2 | Coatomer subunit beta |
| 117 | AP2M1 | cDNA FLJ53069, highly similar to AP-2 complex subunit mu-1 |
| 118 | COPG | Coatomer subunit gamma |
| 119 | LRPAP1 | alpha-2-macroglobulin receptor-associated protein |
| 120 | DYNC1H1 | Cytoplasmic dynein 1 heavy chain 1 |
| 121 | CTSC | cathepsin C |
| 122 | ATP6V1A | V-type proton ATPase catalytic subunit A |
| 123 | COPA | coatomer protein complex, subunit alpha isoform 1 |
| 124 | SERPINB1 | similar to Leukocyte elastase inhibitor (LEI) (Serpin B1) (Leukocyte neutral proteinase inhibitor) (LNPI) |
| 125 | AP2A1 | Isoform A of AP-2 complex subunit alpha-1 |
| 126 | RPL8 | similar to ribosomal protein L8 |
| 127 | SERPINH1 | serpin H1 precursor |
| 128 | PDIA6 | Protein disulfide-isomerase A6 |
| 129 | GENSCAN00000044034 | chromosome:Sscrofa9:7:22008598:22010499:-1 transcript:GENSCAN00000044034 |

TABLE 3-continued

Upregulated Proteins

| No. Acronym | Protein |
| --- | --- |
| 130 PDAP1 | 28 kDa heat- and acid-stable phosphoprotein |
| 131 ARPC3 | actin-related protein 2/3 complex subunit 3 |
| 132 HNRNPK | Isoform 2 of Heterogeneous nuclear ribonucleoprotein K |
| 133 PFN1 | Profilin-1 |
| 134 LUM | similar to lumican |
| 135 RAB14 | Ras-related protein Rab-14 |
| 136 COPE | Coatomer subunit epsilon |
| 137 GOLIM4 | Golgi integral membrane protein 4 |
| 138 COPB1 | coatomer protein subunit beta 1 |
| 139 LOC733658 | hypothetical protein |
| 140 ALB | albumin |
| 141 RPL7 | 60S ribosomal protein L7 |
| 142 ARL1 | ADP-ribosylation factor-like protein 1 |
| 143 HNRNPR | Heterogeneous nuclear ribonucleoprotein-R2 |
| 144 SERPINA3-3 | alpha-1-antichymotrypsin 3 |
| 145 ITIH1 | inter-alpha-trypsin inhibitor heavy chain H1 precursor |
| 146 STOM | Erythrocyte band 7 integral membrane protein |
| 147 ARCN1 | Coatomer subunit delta variant 2 |
| 148 H1FT | Histone H1t |
| 149 HNRNPU | Isoform Long of Heterogeneous nuclear ribonucleoprotein U |
| 150 RPL17 | 60S ribosomal protein L17 |
| 151 GNB2L1 | guanine nucleotide-binding protein subunit beta-2-like 1 |
| 152 PFKL | 6-phosphofructokinase, liver type (EC 2.7.1.11) (Phosphofructokinase 1) (Phosphohexokinase) (Phosphofructo-1-kinase isozyme B) (PFK-B). Isoform 2 |
| 153 UF | Tartrate-resistant acid phosphatase type 5 |
| 154 S100A8 | calcium-binding protein S100A8 |
| 155 GENSCAN00000011448 | chromosome:Sscrofa9:6:119512835:119582882:-1 transcript:GENSCAN00000011448 |
| 156 EIF3F | Eukaryotic translation initiation factor 3 subunit F |
| 157 HMGB2 | High mobility group protein B2 |
| 158 EIF4G1 | EIF4G1 protein |
| 159 EIF3I | Eukaryotic translation initiation factor 3 subunit I |
| 160 RPS3A | ribosomal protein S3A |
| 161 HBA1 | Hemoglobin Alpha 1 |
| 162 HBA2 | Hemoglobin Alpha 2 |
| 163 PREP | Prolyl endopeptidase |
| 164 IGHM | Immunoglobulin mu heavy chain constant region |
| 165 HBE1 | Hemoglobin Epsilon 1 |
| 166 TYSND1 | Peroxisomal leader peptide-processing protease |
| 167 RIC8B | Resistance to inhibitors of cholinesterase 8 homolog B |
| 168 KPNA3 | Karyopherin Alpha-3 (Importin-4) |
| 169 PAPPA | Pregnancy-Associated Plasma Protein A |
| 170 GRK7 | G protein-coupled receptor kinase 7 |
| 171 RPL7L1 | 60S ribosomal protein L7-like 1 |
| 172 PI4 | Protease Inhibitor 4 |
| 173 PCI | Protein C Inhibitor |
| 174 SERPINA6 | Serpin Peptidase Inhibitor, Clade A, Member 6 |
| 175 DNAH10 | Dynein, Axonemal, Heavy Chain 10 |
| 176 CYP26A1 | Cytochrome P450 26A1 |
| 177 APOA4 | Apolipoprotein A-IV |
| 178 ABO | Histo-blood group ABO system transferase |
| 179 MED12 | Mediator of RNA polymerase II transcription subunit 12 |
| 180 HIST1H4J | Histone H4 |
| 181 HIST1H2AD | Histone H2A type 1-D |
| 182 ETFB | Electron transfer flavoprotein subunit beta |
| 183 PIK3CG | Phosphoinositide-3-kinase, catalytic, gamma polypeptide |
| 184 GPX8 | Glutathione peroxidase 8 |
| 185 MYO1D | Myosin-1d |

Table 4 provides a listing of proteins that are decreased after the trauma of surgery. These proteins may be used to determine the degree of trauma resulting from the use of a particular medical device when making an incision. A decrease in the level of the protein indicates greater tissue damage from the medical device. A smaller decrease in the level of the protein can therefore be used to identify a less traumatic, hence less damaging surgical cutting instrument. In addition or in the alternative, a smaller decrease in the level of the protein may be used to identify a reduced susceptibility of a particular patient to tissue damage; and such information may thus be used to modify the selection of a medical device for use on the patient, to modify the way in which a medical device is used in/on the patient, and/or to select the type/amount of one or more agents to be administered to the patient at the wound site. The level of these proteins may in general be more useful than the level of the corresponding mRNA because these protein levels may have been directly affected by surgery rather than by upregulation of the associated gene. It should also be understood that the listing of Table 4 is not intended to be exhaustive, as other proteins may be decreased after the trauma of surgery.

TABLE 4

Downregulated Proteins

| No. | Acronym | Protein |
|---|---|---|
| 1 | FASN | Fatty Acid Synthase |
| 2 | FABP4 | Fatty Acid Binding Protein 4 |
| 3 | HLA-DQB1 | Major Histocompatibility Complex, Class II, Dq Beta-1 |
| 4 | TF | Transferrin |
| 5 | ADAM7 | A Disintegrin And Metalloproteinase Domain 7 |
| 6 | BTBD9 | BTB/POZ Domain-Containing Protein 9 |
| 7 | F9 | Coagulation Factor IX |
| 8 | HPX | Hemopexin |
| 9 | BTBD1 | BTB/POZ Domain-Containing Protein 1 |
| 10 | EML5 | Echinoderm microtubule-associated protein-like 5 |
| 11 | AACT | Alpha-1-Antichymotrypsin |
| 12 | PLIN | Perilipin |
| 13 | TOP2A | DNA Topoisomerase 2 |
| 14 | COL6A2 | Alpha 2 Type VI Collagen |
| 15 | CHDH | Choline dehydrogenase, mitochondrial |
| 16 | GSN | Gelsolin |
| 17 | TUBB | Tubulin beta polypeptide |
| 18 | ANKRD60 | Ankyrin Repeat Domain 60 |
| 19 | BMP1 | Bone Morphogenetic Protein 1 |
| 20 | PS1TP5BP1 | PS1TP5-binding protein 1 |
| 21 | VDAC1P5 | voltage-dependent anion-selective channel protein 3 |
| 22 | UQCRC1 | similar to ubiquinol--cytochrome c reductase |
| 23 | UQCRQ | cytochrome b-c1 complex subunit 8 |
| 24 | ATP5B | mitochondrial ATP synthase, H+ transporting F1 complex beta subunit |
| 25 | ATP2A1 | sarcoplasmic/endoplasmic reticulum calcium ATPase 1 |
| 26 | EPM2A | similar to Laforin (Lafora PTPase) (LAFPTPase) |
| 27 | ATP2A2; SERCA2 | Sarcoplasmic/endoplasmic reticulum calcium ATPase 2 |
| 28 | GENSCAN00000038257 | chromosome:Sscrofa9:13:76148115:76308481:1 transcript:GENSCAN00000038257 |
| 29 | NIPSNAP3A | similar to Protein NipSnap homolog 3A (NipSnap3A) (NipSnap4) (Target for Salmonella secreted protein C) (TassC) |
| 30 | DHRS7C | dehydrogenase/reductase (SDR family) member 7C |
| 31 | FH | Fumarate hydratase, mitochondrial |
| 32 | MACROD1 | MACRO domain containing 1 |
| 33 | HIBADH | 3-hydroxyisobutyrate dehydrogenase |
| 34 | OGDH | OGDH protein |
| 35 | TRDN | Triadin |
| 36 | HECW1 | E3 ubiquitin-protein ligase HECW1 |
| 37 | Srl | sarcalumenin |
| 38 | Casq1 | similar to calsequestrin skeletal muscle |
| 39 | CACNB1 | Isoform 2 of Voltage-dependent L-type calcium channel subunit beta-1 |
| 40 | GENSCAN00000042606 | chromosome:Sscrofa9:6:32691305:32779467:-1 transcript:GENSCAN00000042606 |
| 41 | RYR1 | ryanodine receptor |
| 42 | PYGM | muscle glycogen phosphorylase |
| 43 | CAMK2A | calcium/calmodulin-dependent protein kinase II alpha isoform 1 |
| 44 | Phkg1 | phosphorylase kinase, gamma 1 |
| 45 | PYGB | Glycogen phosphorylase, brain form |
| 46 | HRC | sarcoplasmic reticulum histidine-rich calcium-binding protein |
| 47 | AMPD1 | adenosine monophosphate deaminase 1 |
| 48 | IDH3B | mitochondrial NAD + isocitrate dehydrogenase 3 beta variant 1 |
| 49 | LCTHIO | long-chain 3-ketoacyl-CoA thiolase |
| 50 | RTN4 | reticulon-4 |
| 51 | AGL | amylo-1,6-glucosidase, 4-alpha-glucanotransferase-like |
| 52 | MDH2 | Malate dehydrogenase, mitochondrial |
| 53 | CACNA1S; CACNA1S | Voltage-dependent L-type calcium channel subunit alpha-1S |
| 54 | CAMK2G | calcium/calmodulin-dependent protein kinase type II subunit gamma |
| 55 | STBD1 | similar to Starch-binding domain-containing protein 1 (Genethonin-1) |
| 56 | COX7A1 | cytochrome c oxidase polypeptide VIIa-muscle/heart |
| 57 | ACO2 | Aconitate hydratase, mitochondrial |
| 58 | MURC | similar to PTRF/SDPR family protein |
| 59 | PFMK | muscle 6-phosphofructokinase |
| 60 | CKMT2 | creatine kinase S-type, mitochondrial |
| 61 | SLC25A4 | Solute carrier family 25 member 4 variant (Fragment) |
| 62 | GYS1 | Glycogen [starch] synthase, muscle |
| 63 | IDH2 | isocitrate dehydrogenase [NADP], mitochondrial |
| 64 | DLD | Dihydrolipoyl dehydrogenase |
| 65 | NDUFS6 | NADH dehydrogenase (ubiquinone) Fe—S protein 6, 13 kDa (NADH-coenzyme Q reductase) |
| 66 | PHKB | Phosphorylase b kinase regulatory subunit beta |
| 67 | CRAT | carnitine acetyl transferase |
| 68 | CPSF2 | similar to cleavage and polyadenylation specific factor 2, 100 kDa |
| 69 | NDUFS3 | NADH dehydrogenase (ubiquinone) Fe—S protein 3, 30 kDa (NADH-coenzyme Q reductase) |
| 70 | NDUFA7 | NADH dehydrogenase (ubiquinone) 1 alpha subcomplex, 7, |
| 71 | COX6B | COX6B |

TABLE 4-continued

Downregulated Proteins

| No. | Acronym | Protein |
|---|---|---|
| 72 | ATP5L | ATP synthase subunit g, mitochondrial |
| 73 | SDHA | Succinate dehydrogenase [ubiquinone] flavoprotein subunit, mitochondrial |
| 74 | COQ10A | similar to coenzyme Q10 homolog A |
| 75 | NDUFB9 | similar to NADH dehydrogenase [ubiquinone] 1 beta subcomplex subunit 9 (NADH-ubiquinone oxidoreductase B22 subunit) (Complex I-B22) (CI-B22) |
| 76 | NDUFA12 | NADH dehydrogenase [ubiquinone] 1 alpha subcomplex subunit 12 |

It will be understood by one skilled in the art that not only the specific gene or protein listed can be useful in identifying less damaging surgical instruments, but that other members of the protein family, which includes the specific gene or protein, may also be used. For example, both Alpha 3 type VI collagen and Alpha 2 type VI collagen may be decreased after surgical intervention. Other isoforms or family members of collagen could likewise be used as biomarkers of trauma induced by surgery. Assays may involve either a specific member of a family of genes or proteins, or may include a partial or complete combination of the genes or proteins of a family.

Table 5 provides a listing of proteins that are believed to be beneficial to the long-term healing process. These proteins may thus be used to determine the speed of healing from a wound, such as a wound caused by a medical device. In particular, a surgical device that increases the level of these proteins should provide a relatively more rapid wound healing (as compared to a surgical device that fails to increase the protein levels or does not increase the protein levels as much). In addition or in the alternative, these proteins may be used to determine a particular patient's propensity to heal, such that increased levels of these proteins may demonstrate a relatively greater propensity of the particular patient to heal from tissue trauma. It should also be understood that the listing of Table 5 is not intended to be exhaustive, as other proteins may be beneficial to the long-term healing process.

TABLE 5

Beneficial Upregulated Proteins

| No. | Acronym | Protein |
|---|---|---|
| 1 | MYO1D | Myosin-Id |
| 2 | ATL3 | Isoform 1 of Atlastin-3 |
| 3 | GUSB | beta-glucuronidase precursor |
| 4 | NAGA | N-acetylgalactosaminidase alpha |
| 5 | S100A6 | protein S100-A6 |
| 6 | LDHA | L-lactate dehydrogenase A chain |
| 7 | MYOF | PREDICTED: fer-1-like 3, myoferlin (C. elegans) |
| 8 | FCGR3B | Low affinity immunoglobulin gamma Fc region receptor III |
| 9 | MYOF | Isoform 1 of Myoferlin |
| 10 | SBAB-591C4.1; SLA-DRB1 | major histocompatibility complex, class II, DR beta 1 |
| 11 | NT5E | similar to 5 nucleotidase, ecto |
| 12 | Dync1h1 | cytoplasmic dynein 1 heavy chain 1 |
| 13 | Ap2a2 | adaptor-related protein complex 2, alpha 2 subunit |
| 14 | ANXA5 | annexin A5 |
| 15 | PDIA5 | protein disulfide-isomerase A5 |
| 16 | AHNAK | Neuroblast differentiation-associated protein AHNAK |
| 17 | IQGAP1 | Ras GTPase-activating-like protein IQGAP1 |
| 18 | RPL38 | 60S ribosomal protein L38 |
| 19 | TUBB2A | tubulin beta chain |
| 20 | BEST3 | bestrophin 3 |
| 21 | TUBB1 | Tubulin beta-1 chain |
| 22 | AP2S1 | Isoform 1 of AP-2 complex subunit sigma |
| 23 | PTGIS | Prostaglandin I2 (prostacyclin) synthase |
| 24 | CNN2 | h2-calponin |
| 25 | TXNDC5 | similar to Thioredoxin domain-containing protein 5 precursor (Thioredoxin-like protein p46) (Endoplasmic reticulum protein ERp46) |
| 26 | RPL9 | 60S ribosomal protein L9 |

Table 6 also provides a listing of proteins that are believed to relate to the long-term healing process. These proteins may thus be used to determine the speed of healing from a wound, such as a wound caused by a medical device. In particular, a surgical device that decreases the level of these proteins should provide a relatively more rapid wound healing (as compared to a surgical device that fails to decrease the protein levels or does not decrease the protein levels as much). In addition or in the alternative, these proteins may be used to determine a particular patient's propensity to heal, such that decreased levels of these proteins may demonstrate a relatively greater propensity of the particular patient to heal from tissue trauma. It should also be understood that the listing of Table 6 is not intended to be exhaustive, as other proteins may relate to the long-term healing process.

TABLE 6

Beneficial Downregulated Proteins

| No. | Acronym | Protein |
|---|---|---|
| 1 | Uqcrc2 | ubiquinol cytochrome c reductase core protein 2 |
| 2 | KRT10 | Keratin, type I cytoskeletal 10 |

Table 7 provides a listing of proteins that respond rapidly to surgical incisions, and are thus believed to indicate quality or speed of hemostatis. These proteins may thus be used to determine the superiority of hemostasis in response to a wound, such as a wound caused by a medical device. In particular, a surgical device that increases the level of these proteins should provide relatively better or faster hemostasis (as compared to a surgical device that fails to increase the protein levels or does not increase the protein levels as much). In addition or in the alternative, these proteins may be used to determine a particular patient's propensity to achieve hemostasis, such that increased levels of these proteins may demonstrate a relatively greater propensity of the particular patient to achieve hemostasis in response to tissue trauma. It should also be understood that the listing of Table 7 is not intended to be exhaustive, as other proteins may relate to the quality or speed of hemostasis.

TABLE 7

Upregulated Fast-response Proteins

| No. | Acronym | Protein |
|---|---|---|
| 1 | EIF3A | Eukaryotic translation initiation factor 3 subunit A |
| 2 | TPM2 | Tropomyosin 2 |
| 3 | DARS | Aspartyl-tRNA synthetase, cytoplasmic |
| 4 | RCN1 | Reticulocalbin-1 |
| 5 | PPP1CB | protein phosphatase 1 catalytic subunit beta isoform |
| 6 | LRRC59 | Leucine-rich repeat-containing protein 59 |
| 7 | EEF1G | eukaryotic elongation factor 1 gamma-like protein |
| 8 | SEC24C | SEC24 related gene family, member C (*S. cerevisiae*) |
| 9 | EIF2S3 | Eukaryotic translation initiation factor 2 subunit 3 |
| 10 | HSP70.2 | heat shock 70 kDa protein 1A |
| 11 | PSMD7 | 26S proteasome non-ATPase regulatory subunit 7 |
| 12 | GLRX5 | PRO1238 |
| 13 | NPG4 | PR-2 protein |
| 14 | HBA | Hemoglobin subunit alpha |

Table 8 also provides a listing of proteins that respond rapidly to surgical incisions, and are thus believed to indicate quality or speed of hemostatis. These proteins may thus be used to determine the superiority of hemostasis in response to a wound, such as a wound caused by a medical device. In particular, a surgical device that decreases the level of these proteins should provide relatively better or faster hemostasis (as compared to a surgical device that fails to decrease the protein levels or does not decrease the protein levels as much). In addition or in the alternative, these proteins may be used to determine a particular patient's propensity to achieve hemostasis, such that decreased levels of these proteins may demonstrate a relatively greater propensity of the particular patient to achieve hemostasis in response to tissue trauma. It should also be understood that the listing of Table 8 is not intended to be exhaustive, as other proteins may relate to the quality or speed of hemostasis.

TABLE 8

Downregulated Fast-response Proteins

| No. | Acronym | Protein |
|---|---|---|
| 1 | SYNCRIP | similar to SYNCRIP protein |
| 2 | GENSCAN00000012699 | chromosome:Sscrofa9:12:16859819: 16873906:-1 transcript:GENSCAN00000012699 |
| 3 | EPB42 | erythrocyte membrane protein band 4.2 |

III. Exemplary Uses of Biomarkers to Influence Use of Therapeutic Agents

In addition to assessing the effectiveness of surgical devices, biomarkers as described herein may also be used to assess the combination of the most desirable surgical device along with one or more therapeutic agents (or even just the most desirable therapeutic agent(s), without also determining the most desirable surgical device). Hence, concepts described herein could be used to develop a combination of a surgical device and/or one or more therapeutic agents that reduce the trauma of surgery by monitoring the levels or production of biomarkers identified in real-time during the course of the surgery. Such methods could be especially useful in chronic wounds or burns where multiple surgical debridement of dead tissue is needed throughout a prolonged recovery phase; or in any wound where the measurement of specific biomarkers would aid in the determination of the course of treatment. Additionally, matrix metalloproteinase may delay wound healing where burn studies in muscle show down-regulation of mitochondrial oxidative phosphorylation and related functions.

An example of a type of therapeutic agent that may reduce the trauma of surgery is vasoconstrictors. Vasoconstrictors, including α-adrenergic sympathomimetics, act by constricting blood vessels and hence blood flow. Since surgery can result in blood loss when veins, arteries or capillaries are breached, use of vasoconstrictors can be beneficial in reducing or preventing unintentional blood loss. By reducing blood loss, the amount of tissue trauma is also decreased, and this will be evident in a modulation of the biomarkers identified in this technology. The efficacy of the combination of surgical device with one or more vasoconstrictors may thus be assessed by monitoring the biomarkers. Although visual observation of bleeding during surgery provides some estimate of the efficacy of the vasoconstrictor, the biomarkers identified can be more beneficially used to evaluate cumulative trauma induced after the wound is closed and the incision site is no longer visible and/or when visual observation is not adequate. Examples of vasoconstrictors include, but are not limited to, amidephrine, cafaminol, cyclopentamine, deoxyepinephrine, epinephrine, felypressin, indanazoline, metizoline, midodrine, naphazoline, nordefrin, octodrine, ornipressin, oxymetazoline, phenylephrine, phenylethanolamine, phenylpropanolamine, propylhexedrine, pseudoephedrine, tetrahydrozoline, tramazoline, tuaminoheptane, tymazoline, vasopressin, xylometazoline and mixtures thereof.

Another example of a type of therapeutic agent that may reduce the trauma of surgery is corticosteroids. Corticosteroids suppress the immune system. When surgery induces tissue trauma, a severe over-reaction of the immune system can occur. By suppressing the over-reaction of the immune system, the amount of tissue trauma may also be decreased, and this may be evident in a modulation of the relevant biomarkers. The efficacy of the combination of surgical device with one or more corticosteroids may thus be assessed by monitoring the biomarkers. Examples of corticosteroids include, but are not limited to, hydrocortisone, cortisone, prednisolone, prednisone, dexamethasone, betamethasone, triamcinolone, fluocinolone, methylprednisolone, fluorometholone, or an ester thereof when chemically possible.

Another example of a type of therapeutic agent that may reduce the trauma of surgery is non-steroidal anti-inflammatory drugs (NSAIDs). NSAIDs reduce inflammation and accompanying pain. When surgery induces tissue trauma, an inflammatory response and accompanying pain may occur. By suppressing the inflammatory response, the amount of tissue trauma may also be decreased, and this may be evident in a modulation of the biomarkers identified. The efficacy of the combination of surgical device with one or more NSAIDs may thus be evaluated by monitoring the biomarkers. Examples of NSAIDs include, but are not limited to, salicylic acid, acetylsalicylic acid (aspirin), bissalicylate, benzyl-benzoic acid, diflunisal, fendosal, indomethacin, acemetacin, cinmetacin, sulindac, tolmetin, zomepirac, diclofenac, fenclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, flunixin, clonixin, phenylbutazone, feprazone, apazone, trimethazone, mofebutazone, kebuzone, suxibuzone, piroxicam, isoxicam and tenoxicam.

Another example of a therapeutic agent that may reduce the trauma of surgery is DNA. By inserting DNA into the cells at the site of the surgery, the DNA may express proteins that are beneficial in reducing surgical trauma and hasten wound healing. The inserted genes may code for any number of different proteins necessary to facilitate tissue recovery. Those proteins that may have a beneficial effect include, but are not limited to, transforming growth factor beta (TGF-β). TGF-β plays a key role in the proliferation and migration of fibroblasts which are an essential part of the wound healing process. By combining the insertion of the DNA for TGF-β into cells at the surgery site with the surgery itself, the wound healing process may be hastened, and this can be monitored by measuring the biomarkers identified.

Various methods may be used to effect insertion of DNA into cells, such as attachment of the DNA to a viral carrier, such as an adenovirus. Another method is to use electrical or mechanical poration of the cell membrane. Accordingly, in some versions, a combination of a surgical device and a separate device for DNA insertion may be used. Alternatively, the same device may be used for both the surgery and the DNA insertion. An example of a single device that would accomplish both the surgery and DNA insertion would be a surgical device energized by ultrasonics in which the ultrasonic energy both mechanically cuts tissue and also induces cell poration for insertion of DNA into cells. The biomarkers identified could then be used to evaluate the degree of tissue trauma and state of the wound healing process, and hence the efficacy of the combination of surgical device and gene therapy-based treatments. Various examples of how genes may be inserted into the cells at the site of the surgery will be described in greater detail below (e.g., section V.D., below), while other examples will be apparent to those of ordinary skill in the art in view of the teachings herein.

As described herein, therapeutic agents, etc. may be administered to a patient in response to biomarker data before, during, and/or after a surgical procedure. For instance, it should be understood that a given patient's biological response (e.g., particular sensitivities and/or propensities for pain/bleeding/healing/revascularization, etc.) to a wound (e.g., traumatic wound or iatrogenic wound, etc.) may differ from the biological response of another patient to the same kind of wound. Such variance in wound response may be based on the particular patient's genetic makeup, prior history, and/or other factors. Thus, it may be useful in some settings to anticipate a particular patient's biological response to a wound before the patient undergoes a surgical procedure. With such information, the patient may be provided certain therapies (e.g., agents) before, during, and/or after the surgery to address the anticipated wound response. In addition or in the alternative, the surgery itself may be tailored based on the anticipated wound response for that particular patient, such as by selection of surgical technique, selection of surgical instruments, selection of operating parameters for surgical instruments, etc. Being able to anticipate a particular patient's unique biological response to a wound may thus be used to optimally customize treatment for that particular patient.

By way of example only, if it is discovered before surgery that the patient has a weak propensity to clot (e.g., as evidenced by a lack of clotting factors), this may be compensated for by administration of clotting factors before a surgical procedure is performed in a highly vascularized organ. As another merely illustrative example, if it is discovered through biomarker data before surgery that the patient has an excessive response to thermal injury, a surgeon may elect to use cryoablation or a Harmonic scalpel instead of using thermal ablation or electrocautery. An excessive inflammatory response could be anticipated and countered before and after the procedure with antihistamines. As yet another merely illustrative example, a patient who will be undergoing major surgery may have a pre-surgery microwound made with an electrosurgical tool in the subcutaneous tissue of the upper arm. A biopsy may later be performed at the site (e.g., 48 hours after the microwound is inflicted) and the sample may be assayed for arginase via immunoassay. If the level is higher than normal, the subject may be given supplemental arginine prior to the surgery. Other examples of responses to biomarker data will be apparent to those of ordinary skill in the art in view of the teachings herein.

In order to anticipate a particular patient's biological response to a wound before the patient undergoes a surgical procedure, the patient may be inflicted with a relatively trivial (i.e., small, minimally affective) "test wound" such as a scratch, burn, puncture, etc., at some time before the surgical procedure is to begin. The patient's biological response (e.g., local or systemic, immunologic, protein or genomic expression changes, etc.) to that "test wound" may be measured based on biomarkers as described herein. The response may be measured within any suitable time frame(s) and for any suitable duration(s). In some settings, and if measurements can be performed rapidly enough, similar conclusions about the particular patient's biological response to a wound may be drawn and utilized to optimize a surgical procedure as the surgical procedure is being performed, such that no pre-surgical "test wound" is needed.

Continuing with the example of anticipating a particular patient's biological response to a wound, it should be understood that periodic re-exposure and evaluation might be warranted in some situations (e.g., since a person's acquired immunologic response may change with time), such that any emergency therapy may be optimized just as a planned/elective therapy could be optimized. It should also be understood that, in some instances, cells may be cultured in vitro as a less traumatic method of biomarker sampling that eliminates the need for a "test wound."

As noted previously, some biomarkers may be expressed immediately, others within hours, others within a week, others within several weeks, etc.; and it may therefore be useful in some instances to tailor biomarker monitoring based on timing, such as to only look for certain biomarkers during certain time frames. For instance, some biomarkers such as those associated with inflammatory and immune response may be expressed about two to seven days after a wound is inflicted (or the expression of such biomarkers may otherwise change around that time period). With respect to therapies or other selections that may be made, it may be desirable to take steps to reduce those biomarkers that are associated with inflammatory and immune response. As another example, some biomarkers such as those associated with angionenesis and myofiber remodeling may be expressed about three weeks after a wound is inflicted (or the expression of such biomarkers may otherwise change around that time period). With respect to therapies or other selections that may be made, it may be desirable to take steps to augment those biomarkers that are associated with remodeling. Thus, the ability to identify the proper therapeutic response to certain biomarker expressions, and to monitor the efficacy of therapeutic responses to certain biomarker expressions, may be tied to particular time frames following the infliction of a wound (be it a "test wound" or a true surgical wound, etc.).

Various other examples of ways in which therapeutic agents, etc. may be administered in response to biomarker data will be described in greater detail below (e.g., section V.B. and section V. D., below), while other examples will be apparent to those of ordinary skill in the art in view of the teachings herein. It should also be understood that various other types of adjustments may be made in response to biomarker data in addition to or in lieu of administration of therapeutic agents, etc., including but not limited to selection of surgical technique, selection of surgical instruments, selection of operating parameters for surgical instruments, etc. Various other types of actions/selections/adjustments/etc. that may be made in response to biomarker data will be apparent to those of ordinary skill in the art in view of the teachings herein.

IV. Exemplary Use of Biomarkers to Evaluate Trauma Caused by Cutting Instruments The following examples relate to various illustrative ways in which biomarkers may be used to evaluate trauma caused by cutting instruments. These examples are provided as experiments described with verbs written in the present tense, though it should be understood that various other kinds of experiments/processes may be carried out to demonstrate the teachings herein.

Example No. 1: Use of UPregulated Genes to Evaluate Surgical Instruments

Four equally-spaced midline, 4 cm length, caudal abdominal incisions are created in two pigs. The umbilical scar region is avoided. An ultrasonic scalpel (Harmonic Blade HK105, by Ethicon Endo-Surgery, Inc. of Cincinnati, Ohio) is used for two incisions and conventional monopolar electrosurgery is used for two incisions on each animal. Using a skin marker, the incision sites are marked on the ventral aspect of the abdomen and identified by level from cranial to caudal, as incision A, B, C, and D respectively. The incision is started with a scalpel blade through the skin (epidermis and dermis). Each incision is deepened through the subcutaneous tissues down to the linea alba. The Harmonic Blade HK105 is set at Power level 5 for cutting tissue and Power level 3 for coagulating bleeders. Monopolar electrosurgery is set at 40 Watts cutting and 40 Watts coagulation with Blend 2/Spray coagulation. Electrosurgery is used in the cutting mode with the coagulation Blend 2/Spray to coagulate bleeders. The linea alba is not incised.

Closure of the incision is effected by apposing the skin with 3-0 nylon in a simple interrupted pattern. Dermabond is applied to seal the epidermis. No bandages are applied to the incisions.

After three days, the pigs are euthanized and each incision site is removed enbloc from the abdominal wall. The tissue block is sliced perpendicular to the surgical incision to create slabs about 4-6 mm thick. The slab is trimmed to remove the skin from the top and muscle from the bottom of the sample. The side walls are trimmed to approximately 4 mm from the surgical incision leaving a rectangular block of subcutaneous fatty tissue. Four to six samples are taken from each incision site and from a control site, which had not previously been incised. Samples are placed in sterile DNAse-, RNAse-, protein-free Eppendorf tubes, flash frozen in liquid nitrogen ($LN_2$), and then held on dry ice throughout tissue collection. The samples are stored in a −80° C. freezer.

Total RNA is isolated in quadruplicate from 100 mg of tissue (four each of control, electrosurgery, and Harmonic). The frozen tissue samples are pulverized in liquid nitrogen and Qiazol buffer (Qiagen; 500 µL per sample) and then further homogenized using Qiashredder columns (Qiagen). RNA is purified using the RNase-Free DNase Set and the RNeasy Lipid Tissue Mini Kit (Qiagen). Isolated RNA is quantified spectrophotometrically (NanoDrop™ 1000; Thermo Scientific) and RNA quality measured (2100 Bioanalyzer and RNA 6000 Nano chips, Agilent Technologies). Only RNA with high integrity (RIN>8.0; 28S/18S>2.0) and concentration (>800 ng/µL) are used in microarray experiments and RNA samples are repurified until each exceeded these standards. Purified RNA is labeled using the One-Cycle Eukaryotic Target Labeling Assay (Affymetrix). Labeled RNA is hybridized to the GeneChip Porcine Genome Arrays (Affymetrix) which contain 23,937 probe sets to interrogate 23,256 transcripts in pig. The arrays are scanned at the Fluidics Station 400 (Affymetrix) and microarray expression data are generated with GeneChip Operating Software (GCOS; Affymetrix). Log transformed raw intensity values for all chips are normalized using RMA Express 1.0.4 (Bolstad et al. Bioinformatics 19:185-193), using Background Adjust, Quantile Normalization, PLM (Probe Level Method). Differential mRNA expression analysis is performed using t-tests. Annotations are taken from S. Tsai et al. Animal Genetics 37 423 (2006).

The measured fold-change for upregulation of mRNA expression for several genes of the test devices relative to the control device is given in the following table 5.

TABLE 5

| Upregulated Genes | | Electrosurgery/Control | | Harmonic/Control | |
|---|---|---|---|---|---|
| Acronym | Gene Name | Fold-Change | p-value | Fold-Change | p-value |
| CXCL6 | Granulocyte chemotactic protein 2 | 122.8 | <0.001 | 77.3 | p < 0.001 |
| CXCL8 | Interleukin-8 | 111.2 | <0.001 | 17.3 | <0.001 |
| ARG1 | Arginase-1 | 86.3 | <0.001 | 25.6 | <0.001 |

The fold-changes for Electrosurgery vs. Control are all higher than the fold-changes for Harmonic vs. Control. This quantitative result is in agreement with qualitative observations made over a much longer duration that the Harmonic device produces less tissue trauma and better wound healing than Electrosurgery. Hence these biomarkers are useful for fast, quantitative assessment of the quality of the surgical device.

Example No. 2: Use of Down-Regulated Genes to Evaluate Surgical Instruments

Four equally-spaced midline, 4 cm length, caudal abdominal incisions are created in two pigs. The umbilical scar region is avoided. An ultrasonic scalpel (Harmonic Blade HK105, by Ethicon Endo-Surgery, Inc. of Cincinnati, Ohio) is used for two incisions and conventional monopolar electrosurgery is used for two incisions on each animal. Using a skin marker, the incision sites are marked on the ventral aspect of the abdomen and identified by level from cranial to caudal, as incision A, B, C, and D respectively. The incision is started with a scalpel blade through the skin (epidermis and dermis). Each incision is deepened through the subcutaneous tissues down to the linea alba. The Harmonic Blade HK105 is set at Power level 5 for cutting tissue and Power level 3 for coagulating bleeders. Monopolar electrosurgery is set at 40 Watts cutting and 40 Watts coagulation with Blend 2/Spray coagulation. Electrosurgery is used in the cutting mode with the coagulation Blend 2/Spray to coagulate bleeders. The linea alba is not incised.

Closure of the incision is effected by apposing the skin with 3-0 nylon in a simple interrupted pattern. Dermabond is applied to seal the epidermis. No bandages are applied to the incisions.

After three days, the pigs are euthanized and each incision site is removed enbloc from the abdominal wall. The tissue block is sliced perpendicular to the surgical incision to create slabs about 4-6 mm thick. The slab is trimmed to remove the skin from the top and muscle from the bottom of the sample. The side walls are trimmed to approximately 4 mm from the surgical incision leaving a rectangular block of subcutaneous fatty tissue. Four to six samples are taken from each incision site and from a control site, which had not previously been incised. Samples are placed in sterile DNAse-, RNAse-, protein-free Eppendorf tubes, flash frozen in liquid nitrogen ($LN_2$), and held on dry ice throughout tissue collection. The samples are stored in a −80° C. freezer.

Total RNA is isolated in quadruplicate from 100 mg of tissue (four each of control, electrosurgery, and Harmonic). The frozen tissue samples are pulverized in liquid nitrogen and Qiazol buffer (Qiagen; 500 µL per sample) a homogenized using Qiashredder columns (Qiagen). RNA is purified using the RNase-Free DNase Set and the RNeasy Lipid Tissue Mini Kit (Qiagen). Isolated RNA is quantified spectrophotometrically (NanoDrop™ 1000; Thermo Scientific) and RNA quality measured (2100 Bioanalyzer and RNA 6000 Nano chips, Agilent Technologies). Only RNA with high integrity (RIN>8.0; 28S/18S>2.0) and concentration (>800 ng/µL) a exceeded these standards. Purified RNA is labeled using the One-Cycle Eukaryotic Target Labeling Assay (Affymetrix). Labeled RNA is hybridized to the GeneChip Porcine Genome Arrays (Affymetrix) which contain 23,937 probe sets to interrogate 23,256 transcripts in pig. The arrays are scanned at the Fluidics Station 400 (Affymetrix) and microarray expression data are generated with GeneChip Operating Software (GCOS; Affymetrix). Log transformed raw intensity values for all chips are normalized using RMA Express 1.0.4 (Bolstad et al. Bioinformatics 19:185-193), using Background Adjust, Quantile Normalization, PLM (Probe Level Method). Differential mRNA expression analysis is performed using t-tests. Annotations are taken from S. Tsai et al. Animal Genetics 37 423 (2006).

The measured fold-change for downregulation of mRNA expression for several genes of the test devices relative to the control device is given in the following table 6.

TABLE 6

| Downregulated Genes | | Control/Electrosurgery | | Control/Harmonic | |
|---|---|---|---|---|---|
| Acronym | Gene Name | Fold-Change | p-value | Fold-Change | p-value |
| PON3 | Paraoxonase 3 | 36.0 | <0.001 | 17.6 | 0.018 |
| MYOC | Myocilin | 26.3 | <0.001 | 9.6 | <0.001 |
| AGT | Angiotensin | 21.2 | <0.001 | 4.5 | 0.025 |

The fold-changes for Control vs. Electrosurgery are all greater than the fold-changes for Control vs. Harmonic. This quantitative result is in agreement with qualitative observations made over a much longer duration that the Harmonic device produces less tissue trauma and better wound healing than Electrosurgery. Hence these biomarkers are useful for fast, quantitative assessment of the quality of the surgical device.

Example No. 3: Use of Elevated Protein Levels to Evaluate Surgical Instruments

Four equally-spaced midline, 4 cm length, caudal abdominal incisions are created in two pigs. The umbilical scar region is avoided. An ultrasonic scalpel (Harmonic Blade HK105, by Ethicon Endo-Surgery, Inc. of Cincinnati, Ohio) is used for two incisions and conventional monopolar electrosurgery is used for two incisions on each animal. Using a skin marker, the incision sites are marked on the ventral aspect of the abdomen and identified by level from cranial to caudal, as incision A, B, C, and D respectively. The incision is started with a scalpel blade through the skin (epidermis and dermis). Each incision is deepened through the subcutaneous tissues down to the linea alba. The Harmonic Blade HK105 is set at Power level 5 for cutting tissue and Power level 3 for coagulating bleeders. Monopolar electrosurgery is set at 40 Watts cutting and 40 Watts coagulation with Blend 2/Spray coagulation. Electrosurgery is used in the cutting mode with the coagulation Blend 2/Spray to coagulate bleeders. The linea alba is not incised.

Closure of the incision is effected by apposing the skin with 3-0 nylon in a simple interrupted pattern. Dermabond is applied to seal the epidermis. No bandages are applied to the incisions.

After three days, the pigs are euthanized and each incision site is removed enbloc from the abdominal wall. The tissue block is sliced perpendicular to the surgical incision to create slabs about 4-6 mm thick. The slab is trimmed to remove the skin from the top and muscle from the bottom of the sample. The side walls are trimmed to approximately 4 mm from the surgical incision leaving a rectangular block of subcutaneous fatty tissue. Four to six samples are taken from each incision site and from a control site, which had not previously been incised. Samples are placed in sterile DNAse-, RNAse-, (protein-free) Eppendorf tubes, flash frozen in liquid nitrogen ($LN_2$), and then held on dry ice throughout tissue collection. The samples are stored in a −80° C. freezer.

Total protein is isolated in quadruplicate from tissue (four each of control, electrosurgery, and Harmonic). The samples are weighed and weights are normalized relative to that of the smallest sample. Samples are ground in liquid nitrogen in a mortar and pestle and collected in new tubes. Proteins are extracted from the samples using a differential detergent fractionation (DDF) procedure. This provides four protein fractions (cytosolic, membrane/organelle, nuclear and least soluble) for each sample to give a total of 48 samples to be analyzed by nano-spray 2-dimensional liquid chromatography tandem mass spectrometry (2-D LC MS2). Each DDF is then precipitated in 50% trichloroacetic acid (½ volume, 30 min) and washed twice in ice-cold acetone (ACN) to remove salts and detergents. Protein pellets are resuspended in 100 mM ammonium bicarbonate, 5% HPLC grade acetonitrile, reduced (5 mM dithiothreitol, 65 C, 10 min), alkylated (10 mM iodoacetamide, 37 C, 30 min) and digested to complete dissolution with trypsin (1:50 w/w, 37 C, 36 hrs).

The tryptic digests are then centrifuged (13,000 g) and supernatants spin-filtered (0.45 μm filter; Ultrafree MC, Millipore). The flow-through is dried out in vacuum centrifuge and resuspended in 250 μl of 2% ACN, 0.1% FA. The samples are further desalted using the Peptide Macro Trap TR1/25108/52 (Michrom Bioresources). Eluted peptides are dried again, and dissolved in 22 μl of 5% ACN and 0.1% formic acid. Twenty microliters of the filtrated peptide mixtures are subjected to 2-D LC MS2. The reverse-phase column (BioBasic C18, 0.18×100-mm Thermo Hypersil-Keystone) is coupled directly in-line with the electro-spray ionization ion trap mass spectrometer equipped with nano-spray source and a column flow rate of 500 nl/min used. The peptides are eluted from a RP column by acetonitrile gradient (in 0.1% FA) of 5%-50% for 580 min, 95% for 20 min, 5% for 25 min, a total of 625 min elution. The mass spectrometer is configured to collect the spectral data by alternating between a single full MS scan followed by three MS-MS scans on the three most intense precursor masses from the full MS scan. The collision energy is normalized to 35%, the dynamic mass exclusion windows are 2 minutes long. MS spectra are measured with an overall mass/charge (m/z) range of 300 to 1,700.

The database of all known porcine genes and human orthogs is used for searching mass spectra using TurboSEQUEST Cluster v. 3.3 SR1. Isotope-free quantitative analysis is performed and is based on spectral counting combined with the increased specificity given by including the quantitative aspects of the Sequest cross correlation (XCorr). Decoy database searching is used to calculate the probability that a tandem mass spectrometry match occurred by chance and, from these, the probability of the protein identification occurring by chance. Only peptides that are identified at $p \leq 0.05$ are used for protein identifications. Monte Carlo resampling protein expression analysis is used in conjunction with multiple testing corrections via the Benjamini-Hochberg method.

The measured levels of elevated proteins as given by the sum of the cross correlation is given for Electrosurgery, Harmonic, and Control in the following table 7.

TABLE 7

| Elevated Proteins | | Sum of Cross Correlation | | |
|---|---|---|---|---|
| Acronym | Gene Name | Electrosurgery | Harmonic | Control |
| HBB | Hemoglobin beta | 4916.3 | 1575.7 | 314.2 |
| HBA | Hemoglobin alpha | 4775.4 | 3138.0 | 796.3 |
| PREP | Prolyl endopeptidase | 1003.3 | 706.7 | 83.9 |

The protein levels are compared to Control and are all higher for Electrosurgery cases than for Harmonic cases. This quantitative result is in agreement with qualitative observations made over a much longer duration that the Harmonic device produces less tissue trauma and better wound healing than Electrosurgery. Hence these biomarkers are useful for quantitative assessment of the quality of the surgical device.

Example No. 4: Use of Decreased Protein Levels to Evaluate Surgical Instruments

Four equally-spaced midline, 4 cm length, caudal abdominal incisions are created in two pigs. The umbilical scar region is avoided. An ultrasonic scalpel (Harmonic Blade HK105, by Ethicon Endo-Surgery, Inc. of Cincinnati, Ohio) is used for two incisions and conventional monopolar electrosurgery is used for two incisions on each animal. Using a skin marker, the incision sites are marked on the ventral aspect of the abdomen and identified by level from cranial to caudal, as incision A, B, C and D respectively. The incision is started with a scalpel blade through the skin (epidermis and dermis). Each incision is deepened through the subcutaneous tissues down to the linea alba. The Harmonic Blade HK105 is set at Power level 5 for cutting tissue and Power level 3 for coagulating bleeders. Monopolar electrosurgery is set at 40 Watts cutting and 40 Watts coagulation with Blend 2/Spray coagulation. Electrosurgery is used in the cutting mode with the coagulation Blend 2/Spray to coagulate bleeders. The linea alba is not incised.

Closure of the incision is effected by apposing the skin with 3-0 nylon in a simple interrupted pattern. Dermabond is applied to seal the epidermis. No bandages are applied to the incisions.

After three days, the pigs are euthanized and each incision site is removed enbloc from the abdominal wall. The tissue block is sliced perpendicular to the surgical incision to create slabs about 4-6 mm thick. The slab is trimmed to remove the skin from the top and muscle from the bottom of the sample. The side walls are trimmed to approximately 4 mm from the surgical incision leaving a rectangular block of subcutaneous fatty tissue. Four to six samples are taken from each incision site and from a control site which had not previously been incised. Samples are placed in sterile DNAse-, RNAse-, protein-free Eppendorf tubes, flash frozen in liquid nitrogen ($LN_2$), and then held on dry ice throughout tissue collection. The samples are stored in a −80° C. freezer.

Total protein is isolated in quadruplicate from tissue (four each of control, electrosurgery, and Harmonic). The samples are weighed and weights are normalized relative to that of the smallest sample. Samples are ground in liquid nitrogen in a mortar and pestle and collected in new tubes. Proteins are extracted from the samples using a differential detergent fractionation (DDF) procedure. This results in four protein fractions (cytosolic, membrane/organelle, nuclear and least soluble) for each sample to provide a total of 48 samples to be analyzed by nano-spray 2-dimensional liquid chromatography tandem mass spectrometry (2-D LC MS2). Each DDF is then precipitated in 50% trichloroacetic acid (½ volume, 30 min) and washed twice in ice-cold acetone (ACN) to remove salts and detergents. Protein pellets are resuspended in 100 mM ammonium bicarbonate, 5% HPLC grade acetonitrile, reduced (5 mM dithiothreitol, 65 C, 10 min), alkylated (10 mM iodoacetamide, 37° C., 30 min) and digested to complete dissolution with trypsin (1:50 w/w, 37° C., 36 hrs).

The tryptic digests are then centrifuged (13,000 g) and supernatants spin-filtered (0.45 μm filter; Ultrafree MC, Millipore). The flow-through is dried out in vacuum centrifuge and resuspended in 250 μl of 2% ACN, 0.1% FA. The samples are further desalted using the Peptide Macro Trap TR1/25108/52 (Michrom Bioresources). Eluted peptides are dried again, and dissolved in 22 μl of 5% ACN and 0.1% formic acid. Twenty microliters of the filtrated peptide mixtures are subjected to 2-D LC MS2. The reverse-phase column (BioBasic C18, 0.18×100-mm Thermo Hypersil-Keystone) is coupled directly in-line with the electro-spray ionization ion trap mass spectrometer equipped with nano-spray source and a column flow rate of 500 nl/min used. The peptides are eluted from RP column by acetonitrile gradient (in 0.1% FA) of 5%-50% for 580 min, 95% for 20 min, 5% for 25 min, a total of 625 min elution. The mass spectrometer is configured to collect the spectral data by alternating between a single full MS scan followed by three MS-MS scans on the three most intense precursor masses from the full MS scan. The collision energy is normalized to 35%, the dynamic mass exclusion windows are 2 minutes long. MS spectra are measured with an overall mass/charge (m/z) range of 300 to 1,700.

The database of all known porcine genes and human orthogs is used for searching mass spectra using TurboSEQUEST Cluster v. 3.3 SR1. Isotope-free quantitative analysis is used and is based on spectral counting combined with the increased specificity given by including the quantitative aspects of the Sequest cross correlation (XCorr). Decoy database searching is used in order to calculate the probability that a tandem mass spectrometry match occurred by chance and, from these, the probability of the protein identification occurring by chance. Only peptides that are identified at p≤0.05 are used for protein identifications. For differential protein expression analysis, Monte Carlo resampling and multiple testing corrections are employed using the Benjamini-Hochberg method.

The measured levels of decreased proteins as given by the sum of the cross correlation is given for Electrosurgery, Harmonic, and Control in the following table 8.

TABLE 8

| Decreased Proteins | | Sum of Cross Correlation | | |
|---|---|---|---|---|
| Acronym | Gene Name | Electrosurgery | Harmonic | Control |
| ALB | Albumin | 3442.3 | 5533.6 | 12052.4 |
| FASN | Fatty acid synthase | 61.8 | 226.3 | 668.4 |
| FABP4 | Fatty acid binding protein 4 | 40.9 | 149.3 | 622.2 |

The protein levels compared to Control are all decreased more for Electrosurgery than for Harmonic. This quantitative result is in agreement with qualitative observations made over a much longer duration that the Harmonic device produces less tissue trauma and better wound healing than Electrosurgery. Hence these biomarkers are useful for fast, quantitative assessment of the quality of the surgical device.

Example 5: Evaluation of the Combination of a Surgical Device and a Vasoconstrictor A Harmonic Blade (by Ethicon Endo-Surgery, Inc. of Cincinnati, Ohio) is used to create an incision in tissue while the tissue is irrigated with an 0.5% phenylephrine HCl solution. A separate incision is made with the Harmonic Blade alone. The incisions are closed and three days later samples are extracted at the incision site. The samples are assayed for the proteins hemoglobin beta, hemoglobin alpha and prolyl endopeptidase. Lower levels of analytes for one of the two samples indicates a superior method of treatment.

Example 6: Evaluation of the Combination of a Surgical Device and a Corticosteroid A Harmonic Blade (by Ethicon Endo-Surgery, Inc. of Cincinnati, Ohio) is used to create an incision in tissue while the tissue is irrigated with an 0.05% dexamethasone solution. A separate incision is made with the Harmonic Blade alone. The incisions are closed and three days later samples are extracted at the incision site. The samples are assayed for mRNA for CXCL6, IL8 and CXCL2. Lower levels of analytes for one of the two samples indicates a superior method of treatment.

Example 7: Evaluation of the Combination of a Surgical Device and an NSAID

A Harmonic Blade (by Ethicon Endo-Surgery, Inc. of Cincinnati, Ohio) is used to create an incision in tissue while the tissue is irrigated with an 0.1% sodium naproxen solution. A separate incision is made with the Harmonic Blade alone. The incisions are closed and three days later samples are extracted at the incision site. The samples are assayed for IL8 and IL6. Lower levels of analytes for one of the two samples indicates a superior method of treatment.

Example 8: Combination Device for Dissection and DNA Delivery

A Harmonic Blade (by Ethicon Endo-Surgery, Inc. of Cincinnati, Ohio) is used to create an incision in tissue while the tissue is irrigated with DNA for TGF-β (20 µg total) ensconced in Optison (GE Healthcare, Little Chalfont, Buckinghamshire, UK). The Harmonic Blade acts both as a tissue scalpel and a cell poration device. A separate incision is made with the Harmonic Blade alone. The incisions are closed and three days later samples are extracted at the incision site. The samples are assayed for IL8 and IL6. Lower levels of analytes for one of the two samples indicates a superior method of treatment.

It should be appreciated from the foregoing that various types of biomarkers may be monitored, quantified, and/or otherwise processed or analyzed to evaluate the type and/or degree of trauma caused to tissue (and/or to evaluate other types of biological effects) by various types of surgical instruments. It should also be appreciated from the foregoing that such evaluations of effects caused by surgical instruments may be used to evaluate the efficacy of the surgical instruments. In addition, it should be understood that biomarker related data may be used to evaluate a particular patient's susceptibility to trauma, propensity for pain/bleeding/healing/revascularization, and/or other biological traits of the particular patient, in addition to or in lieu of being used to evaluate the efficacy of surgical instruments. The evaluation of the efficacy of a surgical instrument and/or the evaluation of biological traits of a particular patient may in turn influence decisions on which surgical instruments to use in particular procedures, how to modify the surgical instruments in subsequent designs, how to modify the use of a given surgical instrument, decisions regarding use of therapeutic agents, and/or various other types of decisions. Other types of decisions that biomarker related evaluations may influence, as well as ways in which biomarker related evaluations may influence those decisions, will be apparent to those of ordinary skill in the art in view of the teachings herein.

V. Exemplary Implementation of Biomarker Monitoring Principles in Medical Devices While examples discussed above include conventional steel scalpels, ultrasonic scalpels, and electrosurgical scalpels, it should be understood that the systems and methods described herein may also be applied to a variety of types of surgical instruments. By way of example only, the systems and methods described herein may be applied to any of the following types of devices: non-energized cutting devices (e.g., scalpels, scissors, etc.); electrosurgical devices (e.g., monopolar or bipolar devices, such as the ENSEAL device by Ethicon Endo-Surgery, Inc. of Cincinnati, Ohio, etc.); ultrasonic devices (e.g., the HARMONIC series of ultrasonic devices by Ethicon Endo-Surgery, Inc. of Cincinnati, Ohio, etc.); surgical stapling devices (e.g., the ECHELON, CONTOUR, or PROXIMATE series of stapling devices by Ethicon Endo-Surgery, Inc. of Cincinnati, Ohio, etc.); trocar devices (e.g., the ENDOPATH XCEL series of trocars by Ethicon Endo-Surgery, Inc. of Cincinnati, Ohio, etc.); hand ports (e.g., the ENDOPATH DEXTRUS series of hand ports by Ethicon Endo-Surgery, Inc. of Cincinnati, Ohio, etc.); other types of access devices (e.g., the SSL access device by Ethicon Endo-Surgery, Inc. of Cincinnati, Ohio, etc.); clip applying devices (e.g., the LIGAMAX or LIGACLIP series of biopsy devices by Ethicon Endo-Surgery, Inc. of Cincinnati, Ohio, etc.); liposuction/tissue suction devices (e.g., ultrasonic liposuction/tissue suction devices or other types, etc.); hard tissue cutting devices (e.g., saws, drills, shavers, etc.); and/or other types of surgical instruments. The methods described herein may also be applicable to any chemical or physical mechanism used to effect surgical procedures, including use of electromagnetic radiation such as radiofrequency, microwave (MASER), infrared, visible (LASER), ultraviolet, x-ray and gamma-ray; sonic or ultrasonic sound waves; fluidics, such as water jets; pneumatics; chemical agents such as acidic or caustic materials, etc. Additional applicable surgical instruments may include HIFU devices or potentially some of the wound healing/enhancing ultrasonic devices such as those used to aid in bone healing. Various other types of surgical instruments to which the systems and methods described herein may be applied, as well as various ways in which the systems and methods described herein may be applied to such surgical instruments, will be apparent to those of ordinary skill in the art in view of the teachings herein.

In addition, while the foregoing examples relate mainly to trauma created by surgical instruments, it should be understood that biomarkers may be monitored, quantified, and/or otherwise processed or analyzed to evaluate the type and/or degree of trauma (and/or other types of biological effects) caused to tissue by other types of medical devices that may not be considered "surgical instruments." By way of example only, the systems and methods described herein may be applied to any of the following types of devices: sutures; surgical staples (e.g., staples from any of the above-mentioned stapling devices, among others); surgical clips (e.g., clips from any of the above-mentioned clip applying devices, among others); gastric bands (e.g., the REALIZE gastric band by Ethicon Endo-Surgery, Inc. of Cincinnati, Ohio, and its associated components, etc.); stents (e.g., any type of stent device by Cordis Corporation of Bridgewater, N.J., etc.); prosthetics (e.g., any type of prosthetic device by DePuy Orthopaedics, Inc. of Warsaw, Ind. or DePuy Spine, Inc. of Raynham, Mass. or DePuy Mitek, Inc. of Raynham, Mass., etc.); implantable drug infusion devices; cardiovascular implants, such as pacemakers; neurological stimulators or inhibitors; closed suction drain systems; low vacuum wound healing systems; and/or other types of implanted devices. Various other types of medical devices to which the systems and methods described herein may be applied, as well as various ways in which the systems and methods described herein may be applied to such medical devices, will be apparent to those of ordinary skill in the art in view of the teachings herein.

A. Exemplary Devices for Capture of Biomarker Data

Several ways in which biomarker data may be captured have already been described herein. However, FIGS. 2-7 show additional specific yet merely illustrative examples of how biomarker data may be captured. The following examples are provided in the context of a harmonic surgical instrument. By way of example only, the teachings below may be readily applied to a harmonic surgical instrument as shown and described in U.S. Pub. No. 2006/0079874, entitled "Tissue Pad for Use with an Ultrasonic Surgical Instrument," published Apr. 13, 2006, now abandoned, the disclosure of which is incorporated by reference herein. As another example, the teachings below may be readily applied to a harmonic surgical instrument as shown and described in U.S. Pub. No. 2007/0191713, entitled "Ultrasonic Device for Cutting and Coagulating," published Aug. 16, 2007, now abandoned, the disclosure of which is incorporated by reference herein. As yet another example, the teachings below may be readily applied to a harmonic surgical instrument as shown and described in U.S. Pub. No. 2007/0282333, entitled "Ultrasonic Waveguide and Blade," published Dec. 6, 2007, now abandoned, the disclosure of which is incorporated by reference herein. As still another example, the teachings below may be readily applied to a harmonic surgical instrument as shown and described in U.S. Pub. No. 2008/0200940, entitled "Ultrasonic Device for Cutting and Coagulating," published Aug. 21, 2008, now abandoned, the disclosure of which is incorporated by reference herein. Still other suitable types of harmonic surgical instruments to which the below teachings may be readily applied will be apparent to those of ordinary skill in the art in view of the teachings herein. It should be understood that, in some versions, harmonic surgical instruments may provide sonoporation capabilities that facilitate gene therapy without the use of viral carriers. Exemplary uses of harmonic surgical instruments for gene therapy through sonoporation will be described in greater detail below in section V.D. Thus, it should be understood that in some versions, a single harmonic device may be used to both obtain biomarker data as described in section V.A. and administer a gene therapy (or other form of therapy/treatment/etc.) based at least in part on such biomarker data.

It is also contemplated that the below teachings may be readily applied to various other kinds of medical devices, including but not limited to surgical instruments, medical implants, etc. For instance, the below teachings may be readily applied to virtually any of the kinds of medical devices that are referred to herein. Still other suitable devices to which the below teachings may be readily applied will be apparent to those of ordinary skill in the art in view of the teachings herein. It should therefore be understood that the below examples include harmonic surgical instruments by way of illustration only, and that the below teachings are not intended to be limited to just harmonic surgical instruments.

It should also be understood that once biomarker data is acquired, either in accordance with the below teachings or otherwise, information from that biomarker data may be used in various ways. For instance, various examples of what may be done with information from biomarker data are described in greater detail elsewhere herein (e.g., section V.B., section V.C., and section V.D., below). Still other suitable examples of what may be done with information from biomarker data will be apparent to those of ordinary skill in the art in view of the teachings herein.

Figure 2:
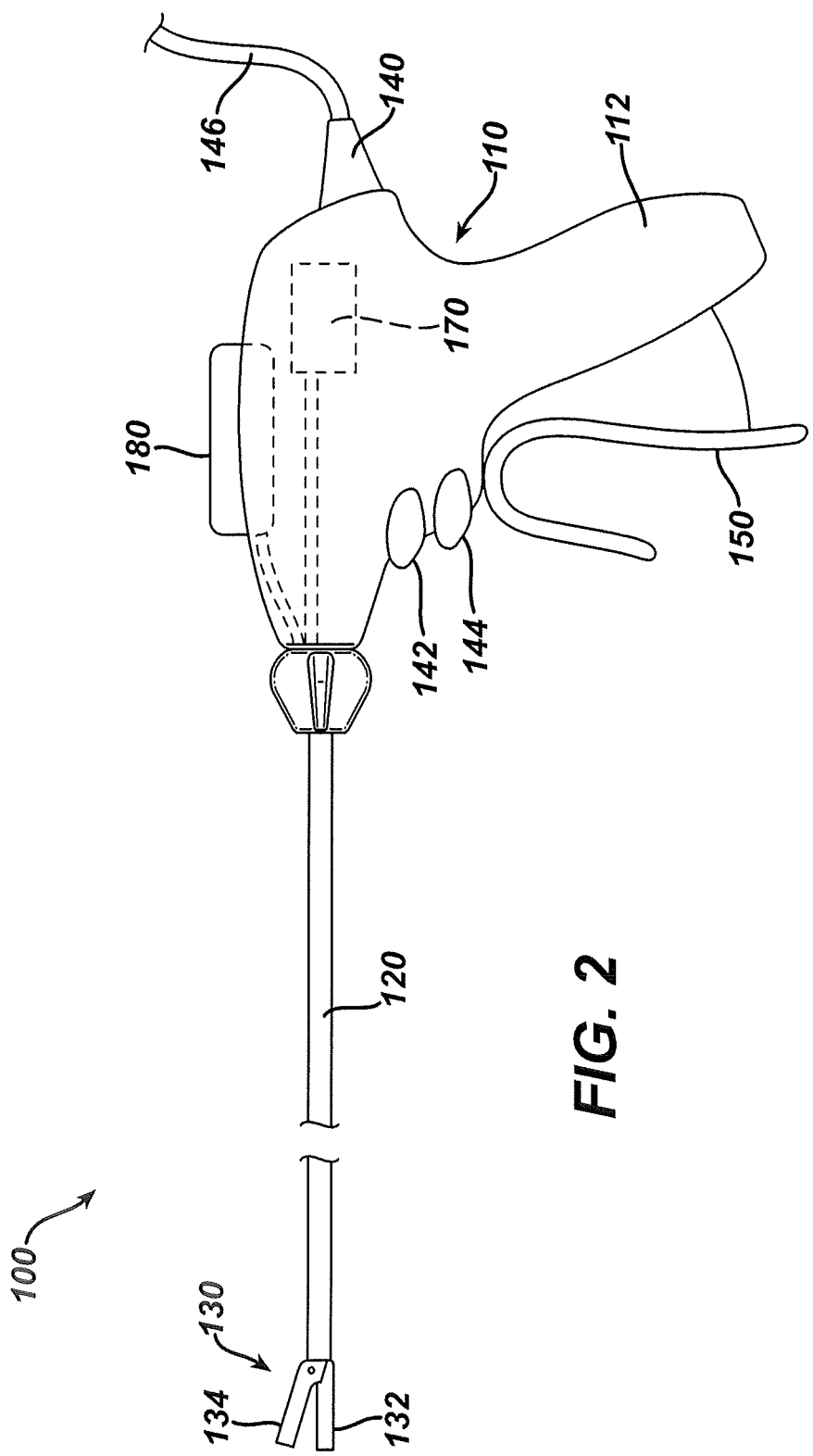
FIG. 2 depicts a side view of an exemplary harmonic surgical instrument having a biomarker collection feature.

1. Exemplary Device for Capture and Retention of Biomarkers for Subsequent Analysis FIG. 2 shows an exemplary device (100) that may be used to capture and retain biomarker data. In the present example, device (100) is essentially a modified version of the harmonic surgical instrument shown and described in U.S. Pub. No. 2006/0079874, now abandoned, though device (100) may of course have any other suitable features, components, and/or configurations, etc. Device (100) of this example has a handle portion (110) including a pistol grip (112). A shaft (120) extends distally from handle portion (110). An end effector (130) is disposed at the distal end of shaft (120). End effector (130) includes a harmonic blade (132) and a clamp pad (134). Harmonic blade (132) is operable to vibrate or oscillate at ultrasonic frequencies (e.g., 55.5 kHz). An ultrasonic transducer (140) is disposed in handle portion (110) and drives harmonic blade (132) through a waveguide (not shown) that is disposed in shaft (120). Ultrasonic transducer (140) receives power from a generator via cable (146). Buttons (142, 144) are operable to selectively activate harmonic blade (132). For instance, one button (142) may provide maximum intensity while the other button (144) provides minimum intensity. Device (100) of this example is configured such that either button (142, 144) must be held down in order to keep ultrasonic blade (132) in an active state, such that harmonic blade (132) returns to an inactive state as soon as a held button (142, 144) is released.

Clamp pad (134) is operable to pivot relative to harmonic blade (132), such as to selectively clamp tissue between clamp pad (134) and harmonic blade (132). In particular, clamp pad (134) is coupled with trigger member (150), which pivots relative to pistol grip (112). A user may thus squeeze trigger member (150) toward pistol grip (112) to pivot clamp pad (134) toward harmonic blade (132) and release trigger member (150) to pivot clamp pad (134) away from harmonic blade (132). In some versions, trigger member (150) is resiliently biased to the position shown in FIG. 2, whereby clamp pad (134) is pivoted away from harmonic blade (132).

Figure 3:
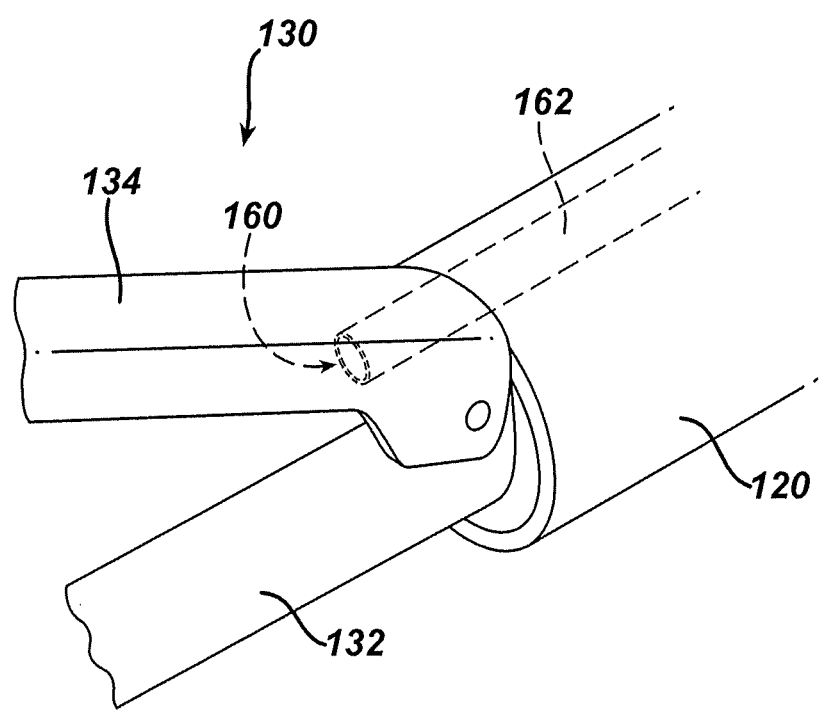
FIG. 3 depicts a partial view of the end effector of the harmonic surgical instrument of FIG. 2.

As shown in FIG. 3, device (100) of this example includes a suction port (160) at end effector (130). Its position at end effector (130) allows suction port (160) to directly draw mist at a wound site as harmonic blade (132) is activated to create the wound and/or to otherwise address the wound (e.g., blade (132) activated to stop bleeding at the wound, etc.). Suction port (160) is at the distal end of a conduit (162), which extends along the full length of shaft (120). A suction pump (170), which is positioned in handle portion (110), is in fluid communication with conduit (162), such that suction pump (170) is operable to draw suction through suction port (160). Suction pump (170) receives power via cable (146). In some versions, suction pump (170) is in communication with buttons (142, 144), such that suction pump (170) is selectively activated/deactivated simultaneously with harmonic blade (132). In some such versions, a control logic activates suction pump (170) as soon as harmonic blade (132) is activated; yet keeps suction pump (170) activated for a certain time period following deactivation of a previously activated harmonic blade (132), allowing suction pump (170) and suction port (160) to draw in any additional mist that may be still emanating or lingering shortly after harmonic blade (132) has been deactivated. In some other versions, a separate button is provided for suction pump (170), such that suction pump (170) may be activated independently of harmonic blade (132). It should also be understood that suction pump (170) may be omitted, and device (100) may include a feature for coupling with an external source of suction/vacuum.

As also shown in FIG. 2, device (100) of the present example includes a capture vessel (180) in communication with conduit (162). In particular, capture vessel (180) is configured to receive and retain cell fragments and/or other biological materials that are picked up in mist drawn through suction port (160). Capture vessel (180) is removable from handle portion (110), such that after a surgical procedure is complete, capture vessel (180) may be taken to a biomarker testing system to process biomarkers embodied in the cell fragments and/or other biological materials that are contained in capture vessel (180). By way of example only, biological materials that are contained in capture vessel (180) may be processed in accordance with the teachings of FIG. 1 and the corresponding written description, in accordance with any other teachings herein, and/or in accordance with any other methods as will be apparent to those of ordinary skill in the art in view of the teachings herein. Capture vessel (180) is configured to maintain the integrity of materials contained therein, allowing those materials to be processed at some time after their capture. In some versions, device (100) includes one or more additional features that are configured to at least partially process biological materials before they reach capture vessel (180) and/or once they reach capture vessel (180). Various suitable components, features, configurations, and operabilities of capture vessel (180) will be apparent to those of ordinary skill in the art in view of the teachings herein. Similarly, various suitable ways in which device (100) may be otherwise modified will be apparent to those of ordinary skill in the art in view of the teachings herein.

2. Exemplary System for Capture and Analysis of Biomarkers in Real Time

Figure 4:
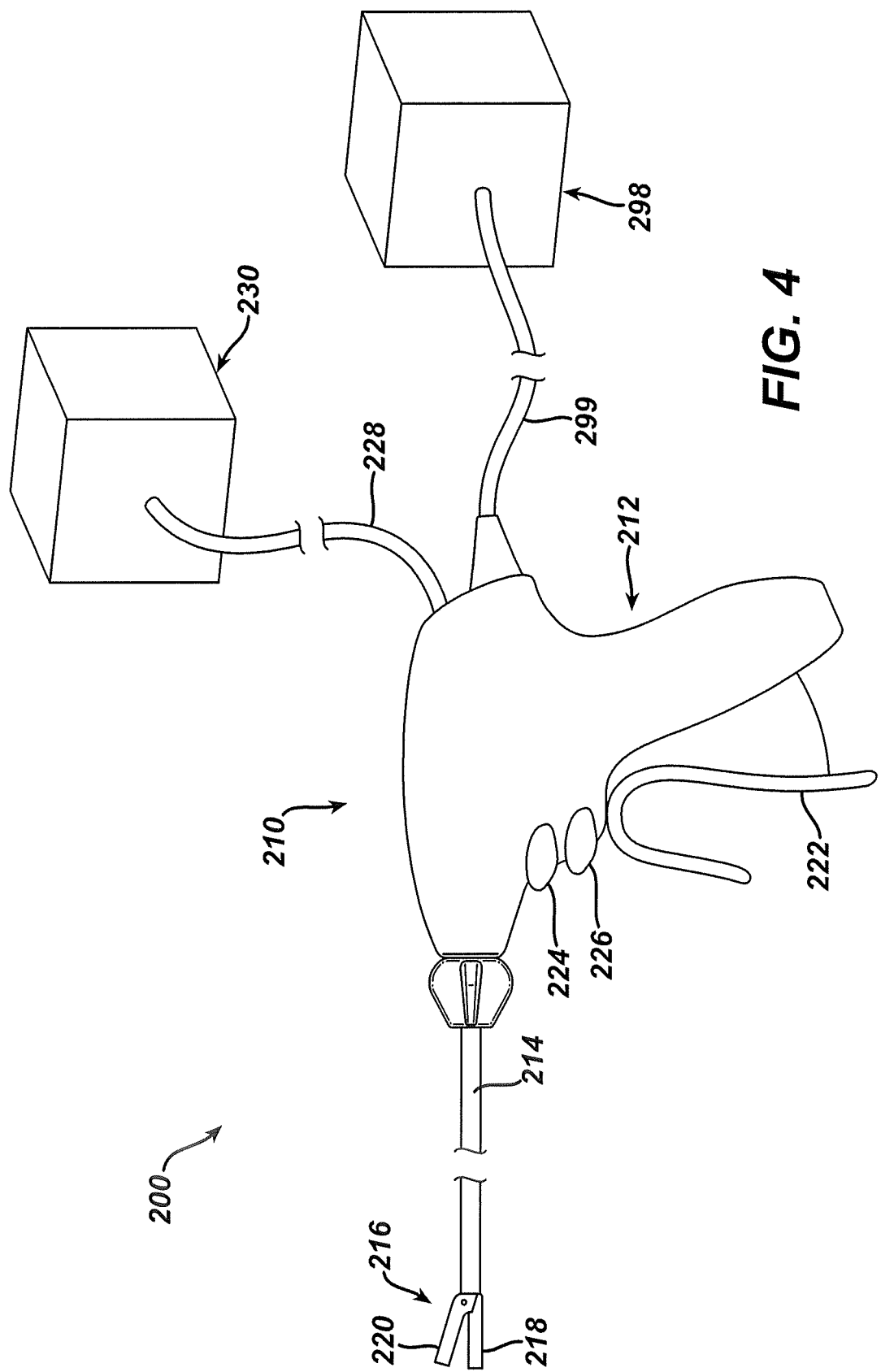
FIG. 4 depicts a schematic view of an exemplary biomarker collection and processing system.
Figure 5:
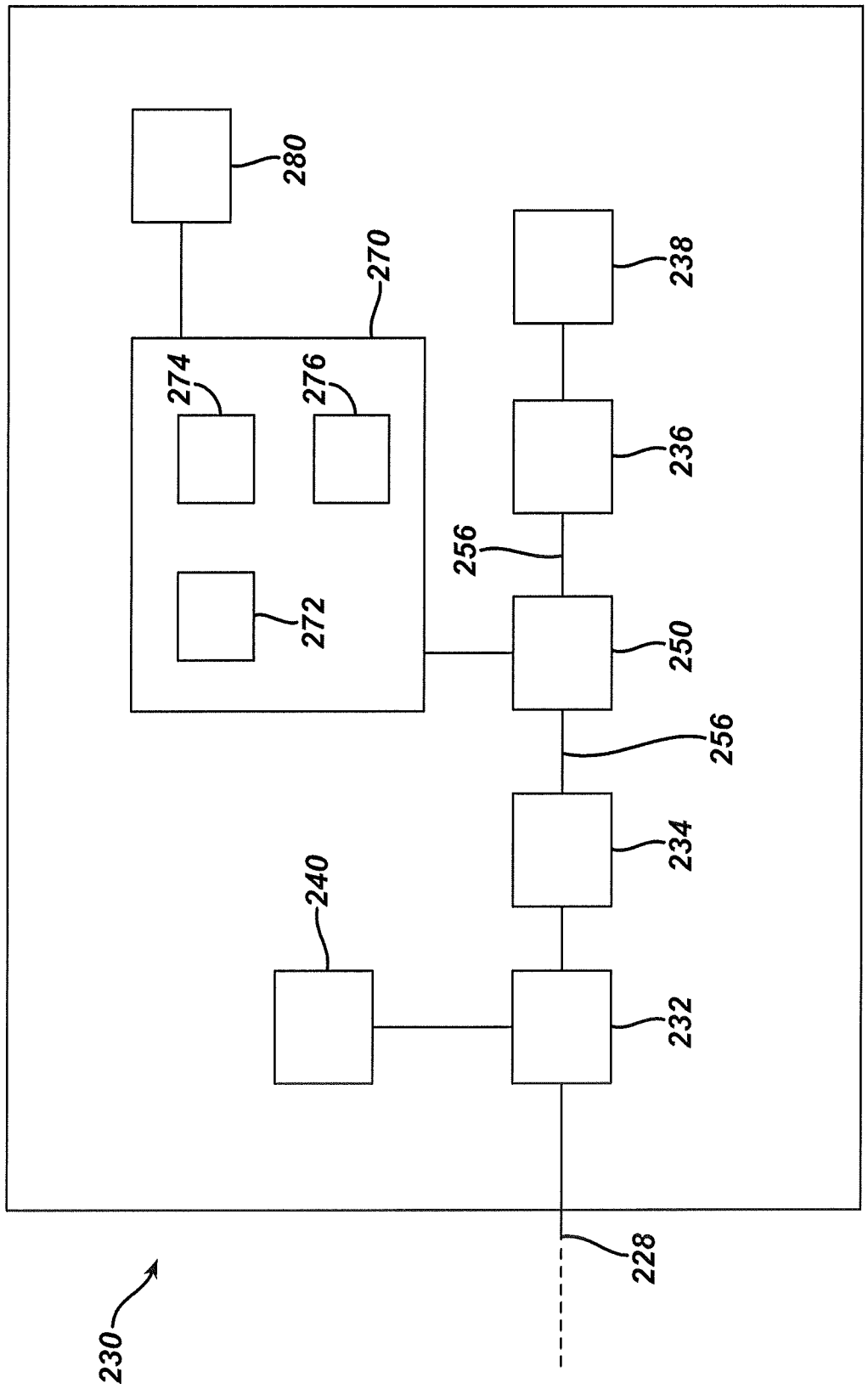
FIG. 5 depicts a schematic view of biomarker processing components of the system of FIG. 4.

FIG. 4 shows an exemplary system (200) that may be used to capture and process biomarker data in real time or near-real time. System (200) of this example includes a harmonic surgical instrument (210), a biomarker processing module (230), and a harmonic generator (298). Harmonic surgical instrument (210) of this example is similar in several ways to device (100) described above. In particular, harmonic surgical instrument (210) of the present example is essentially a modified version of the harmonic surgical instrument shown and described in U.S. Pub. No. 2006/0079874, though harmonic surgical instrument (210) may of course have any other suitable features, components, and/or configurations, etc. Harmonic surgical instrument (210) of this example includes a handle portion (212), a shaft (214) extending distally from handle portion (212), and an end effector (216) positioned at the distal end of shaft (214). End effector (216) includes an harmonic blade (218) and a pivoting clamp member (220). A trigger member (222) is operable to selectively pivot clamp member (220), while buttons (224, 226) are operable to selectively activate harmonic blade (218). End effector (216) of this example also includes a suction port (not shown), much like suction port (160) shown in FIG. 3. A cable (299) couples harmonic surgical instrument (210) with harmonic generator (298), which is operable to energize an ultrasonic transducer (not shown) in handle portion (212) to activate harmonic blade (218). A conduit (228) is also coupled with handle portion (212). Conduit (228) is configured to communicate a mist drawn in by the suction port at end effector (216) to biomarker processing module (230). While biomarker processing module (230) is shown as being a component that is separate from (but tethered to) harmonic surgical instrument (210) in this example, it should be understood that harmonic surgical instrument (210) may be readily modified to include biomarker processing module (230) on board (e.g., within handle portion (212), on handle portion (212), etc.).

Biomarker processing module (230) of the present example is operable to perform at least some of the processing shown in FIG. 1 and described in greater detail above. Of course, it should be understood that biomarker processing module (230) may be operable to perform various other kinds of processing. In the present example, biomarker processing module (230) includes a filter and dilution stage (232), an enzyme cleave stage (234), a biomarker sensor (250), a reservoir (236), and a suction source (238). Suction source (238) is operable to draw a mist through the suction port at end effector (216) during use of harmonic surgical instrument (210), and to continue drawing that mist (and saline and/or other fluids) through biomarker processing module (230) in accordance with block (10) of FIG. 1. While suction source (238) is shown as being an integral component of biomarker processing module (230), it should be understood that suction source (238) may be external to biomarker processing module (230) in some versions. Reservoir (236) is configured to collect and retain fluids that are communicated along the fluid path past biomarker sensor (250). Reservoir (236) may be removable from biomarker processing module (230). In addition, one or more filters may be provided to substantially isolate suction source (238) from liquids and/or debris during operation of biomarker processing module (230). In some other versions, no filters are used with respect to suction source (238). It should also be understood that reservoir (236) may be an integral part of suction source (238) or may even be omitted altogether.

As noted above with respect to the process shown in FIG. 1, saline may be used while processing biomarkers. To that end, biomarker processing module (230) of the present example includes a saline source (240) coupled with filter and dilution stage (232). Filter and dilution stage (232) may also include one or more features that are configured to provide ultrasonic sieving, electrostatic sieving, and/or some other type of filtering of the mist passing through filter and dilution stage (232). Filter and dilution stage (232) is thus operable to filter and dilute the mist in accordance with block (20) of FIG. 1 as the mist proceeds toward biomarker sensor (250). Various suitable components, features, and configurations that may be included in filter and dilution stage (232) will be apparent to those of ordinary skill in the art in view of the teachings herein. Of course, as with other components described herein, filter and dilution stage (232) may be modified, substituted, supplemented, or even omitted, as desired.

In the present example, after being filtered and diluted, the mist reaches enzyme cleave stage (234), which is operable to cleave biomarkers in the mist with enzymes in accordance with block (30) of FIG. 1 as the mist continues to proceed toward biomarker sensor (250). Various suitable components, features, and configurations that may be included in enzyme cleave stage (234) will be apparent to those of ordinary skill in the art in view of the teachings herein. Of course, as with other components described herein, filter and dilution stage (232) may be modified, substituted, supplemented, or even omitted, as desired.

Figure 6:
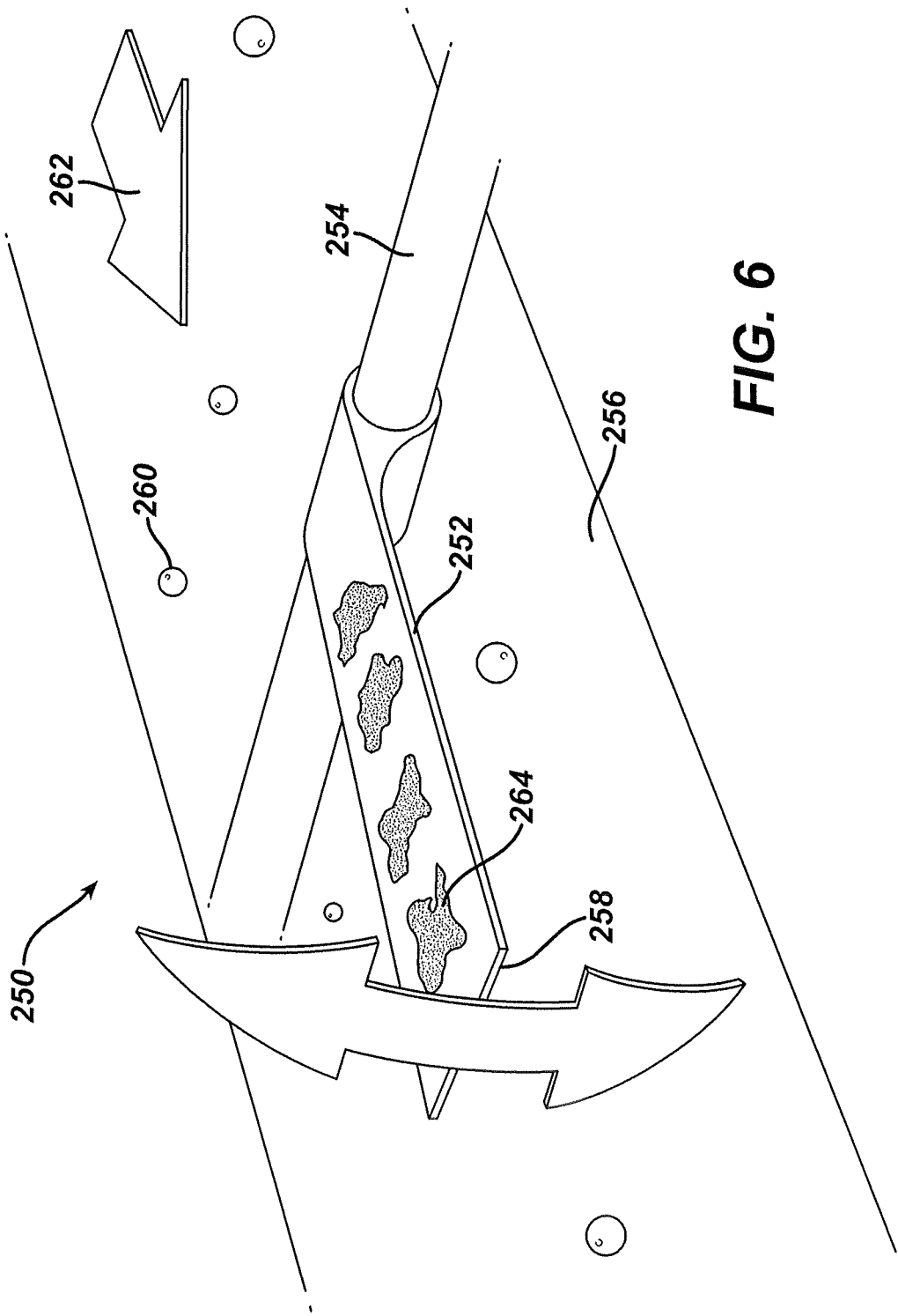
FIG. 6 depicts a partial perspective view of a biomarker sensor of the system of FIG. 4, during a biomarker collection phase.
Figure 7:
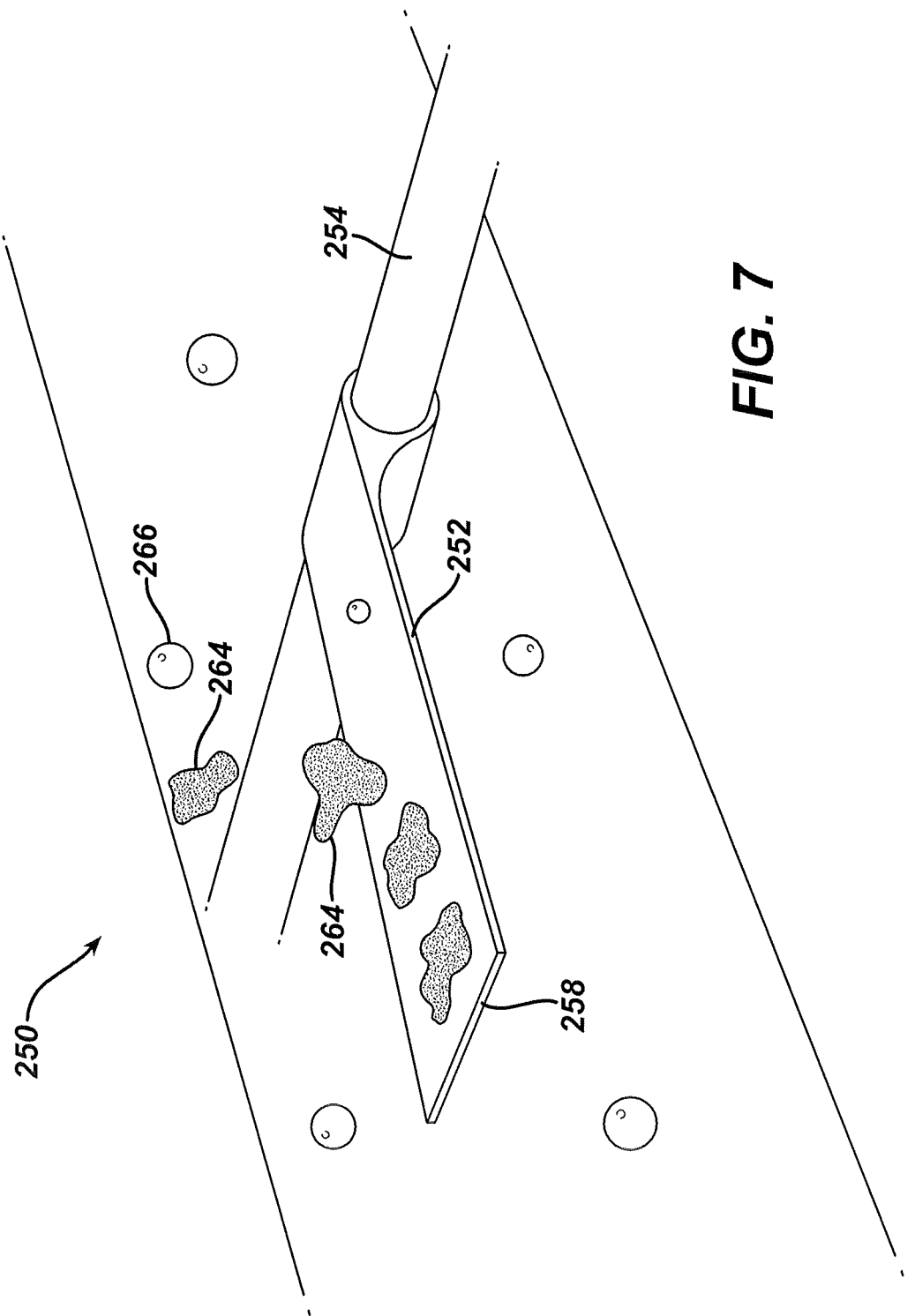
FIG. 7 depicts a partial perspective view of the biomarker sensor of FIG. 6, during a sensor cleansing phase.

Exemplary components for sensor (250) are shown in greater detail in FIGS. 6-7. In particular, sensor (250) of the present example includes a cantilever beam (252) extending outwardly from a shaft (254). Beam (252) is positioned within the main conduit (256) of biomarker processing module (230). Mist particles (260) flow through main conduit (256) as indicated by arrow (262), flowing across beam (252). In some versions, beam (252) includes one or more particular antibodies selected to attract specific complementary antigens/proteins (264) that serve as useful biomarkers in mist particles (260). In addition or in the alternative, beam (252) may include one or more particular nucleotide base pair sequence amino acids selected to attract specific complementary nucleotide sequences (e.g., gene fragments) that serve as useful biomarkers in mist particles (260). Various suitable ways in which such antibodies and/or nucleotide base pair sequence amino acids may be provided on beam (252) will be apparent to those of ordinary skill in the art in view of the teachings herein. It should also be understood that antibodies and/or nucleotide base pair sequence amino acids may be provided on beam (252) as microdot arrays. In addition, it should be understood that antibodies and nucleotide base pair sequence amino acids are just two examples of things that may be provided on beam (252) to attract biomarkers. Other suitable things that may be provided on beam (252) to attract biomarkers (or otherwise be sensitive to biomarkers) will be apparent to those of ordinary skill in the art in view of the teachings herein.

Furthermore, it should be understood that a plurality of beams (252) may be provided in main conduit (256), each beam (252) having its own shaft (254). Regardless of whether just a single beam (252) or more than one beam (252) is provided in main conduit (256), it should be understood that any given beam (252) may be formulated to attract just one biomarker or a combination of biomarkers. Thus, in some versions, several beams (252) are used, such that sensor (250) is capable of detecting several different biomarkers substantially simultaneously. In versions where sensor (250) is capable of detecting several different biomarkers, biomarker processing module (230) may be configured to allow a user to selectively activate only certain beams (252) to selectively detect only one or only some of the kinds of biomarkers that biomarker processing module (230) is capable of detecting. For instance, sensor reader (270) within biomarker processing module (230) may be configured to only take readings from just one or just some of the beams (252) based on user input. As another merely illustrative example, main conduit (256) may be branched into separate sub-conduits via a manifold, each sub-conduit having its own one or more beams (252) dedicated to detection of specific respective biomarkers or specific respective combinations of biomarkers. In some such versions, biomarker processing module (230) may be configured to selectively provide communication of the mist through only those sub-conduits associated with specific biomarkers (or biomarker combinations) specified by the user, such as by controlling a system of valves or gates to distribute the mist based on user selections. Other suitable ways in which a biomarker processing module (230) that is sensitive to different kinds of biomarkers may be carried out will be apparent to those of ordinary skill in the art in view of the teachings herein.

As beam (252) picks up biomarkers from mist particles (260), the mass/weight of beam (252) increases. The results of this effect may be emphasized by concentrating the antibodies and/or nucleotide base pair sequence amino acids, etc. at or near the free end (258) of beam (252). In some versions, beam (252) is substantially rigid, the coupling between beam (252) and shaft (254) is substantially rigid, and shaft (254) is rotatable within main conduit (256) about the longitudinal axis of shaft (254). Thus, as the weight of beam (252) increases from biomarkers being picked up by beam (252), beam (252) and shaft (254) begin to pivot downwardly within main conduit (256). In some such versions, sensor reader (270) within biomarker processing module (230) is able to sense such rotation of shaft (254). In some other versions, beam (252) is substantially rigid, the coupling between beam (252) and shaft (254) is substantially rigid, and shaft (254) is not rotatable within main conduit (256). Thus, as the weight of beam (252) increases from biomarkers being picked up by beam (252), the torsional stress on shaft (254) increases, and the acoustic resonant frequency of shaft (254) changes. Sensor reader (270) may thus be configured to sense the changed torsional stress and/or changed acoustic resonant frequency of shaft (254). As another merely illustrative example, shaft (254) may flex (without necessarily pivoting) as biomarkers gather on beam (252), and such flexing may be picked up by sensor reader (270). In still other versions, beam (252) is substantially rigid, beam (252) is rotatable about shaft (254), and shaft (254) is not rotatable within main conduit (256). Thus, as the weight of beam (252) increases from biomarkers being picked up by beam (252), beam (252) rotates about shaft (254). Sensor reader (270) may thus be configured to sense the rotation of beam (252) about shaft (254). As yet another merely illustrative example, beam (252) is flexible, the coupling between beam (252) and shaft (254) is substantially rigid, and shaft (254) is not rotatable within main conduit (256). Thus, as the weight of beam (252) increases from biomarkers being picked up by beam (252), beam (252) begins to bend downwardly. Sensor reader (270) may thus be configured to sense the bending of beam (252). In some such versions, a strain gauge may be provided on beam (252) to facilitate detection of bending. It should also be understood that one or more reference sensors may also be included. Such reference sensors may be configured to respond to environmental conditions without capturing biomarkers (e.g., to improve signal-to-noise ratio, etc.).

While the above description provides several merely illustrative examples of how different properties, configurations, and relationships of beam (252) and shaft (254) may yield different kinds of mechanical effects in response to biomarkers collecting on beam (252), it should be understood that there are various ways to detect and measure the mechanical effects on beam (252) and/or shaft (254) as biomarkers collect on beam (252). For instance, these mechanical effects may be detected and measured optically (e.g., machine vision directed to one or more optical markers on beam (252) and/or shaft (254), etc.), capacitively (e.g., monitoring changes in capacitance due to movement of and/or stresses in beam (252) and/or shaft (254), etc.), acousitically (e.g., monitoring changes in acoustic resonant frequency of beam (252) and/or shaft (254), etc.), and/or otherwise. Other suitable ways in which the mechanical effects of biomarker collection on beam (252) may be detected and measured will be apparent to those of ordinary skill in the art in view of the teachings herein. In the present example, processing hardware (272) in sensor reader (270) includes the necessary hardware (together with any monitoring hardware in sensor (250) itself) to detect and monitor the mechanical changes and convert such information into information that is usable by the user and/or one or more additional components of system (200).

In some settings, it may be desirable to clean sensor (250) by effectively washing away biomarkers that have collected on beam (252). For instance, sensor (250) may eventually become essentially saturated with biomarkers to the point where it loses sensitivity or effectiveness, such that it is necessary to "recharge" sensor (250). This may become desirable during a single session of use of system (200) for a single patient/subject. In addition or in the alternative, in versions where biomarker processing module (230) is configured to be reusable for several different use sessions (e.g., for the same patient/subject and/or for different patients/subjects), it may be desired to clear out sensor (250) between use sessions. There are various ways in which sensor (250) may be cleaned for re-use. For instance, as shown in FIG. 7, a saline wash (266) may be used to free antigens/proteins (264) and/or nucleotide sequences (e.g., gene fragments), etc. from beam (252). In some versions, saline wash (266) is provided at a temperature that both differs from the temperature of the original mist and is selected to free antigens/proteins (264) and/or nucleotide sequences (e.g., gene fragments), etc. from beam (252). In addition or in the alternative, antigens/proteins (264) and/or nucleotide sequences (e.g., gene fragments), etc. may be substantially cleared from beam (252) electrostatically and/or by changing the pH of the flow over beam (252). Other suitable ways in which antigens/proteins (264) and/or nucleotide sequences (e.g., gene fragments), etc. may be substantially cleared from beam (252) will be apparent to those of ordinary skill in the art in view of the teachings herein. Once antigens/proteins (264) and/or nucleotide sequences (e.g., gene fragments), etc. have been substantially cleared from beam (252), the antibodies and/or nucleotide base pair sequence amino acids, etc. remain on beam (252), such that sensor (250) may be re-used. Of course, sensor (250) may alternatively be configured such that sensor (250) is not re-usable.

It should also be understood that undesirably excessive buildup of biomarkers on beam (252) may be reduced or avoided by selective activation or use of sensor (250). This may be accomplished by providing suction from suction source (238) on a selective basis. For instance, the activation of suction source (238) may be tied to activation of buttons (224, 226) in a manner similar to that described above with respect to device (100). In addition or in the alternative, the mist may be selectively diverted upstream of biomarker processing module (230) or within biomarker processing module (230) before reaching sensor (250). For instance, the mist may be selectively diverted to reservoir (236) and/or to atmospheric air. Still other suitable ways in which undesirably excessive buildup of biomarkers on beam (252) may be reduced or avoided will be apparent to those of ordinary skill in the art in view of the teachings herein.

In some versions, sensor (250) is provided at a MEMS scale size. Alternatively, sensor (250) may have any other suitable size.

Referring back to FIG. 5, and as noted above, sensor reader (270) is coupled with sensor (250) and includes processing hardware (272) that is operable to detect and monitor the mechanical changes and convert such information into information that is usable by the user and/or one or more additional components of system (200). Various suitable components that may be incorporated into processing hardware (272) will be apparent to those of ordinary skill in the art in view of the teachings herein. Sensor reader (270) of the present example also includes a storage medium (274) in communication with processing hardware (272). Storage medium (274) may include volatile memory and/or non-volatile memory that is accessed by processing hardware (272) to process data obtained from sensor (250) (e.g., to check against tables stored in storage medium, etc.). In addition or in the alternative, storage medium (274) may store data processed by processing hardware (272) for subsequent retrieval.

Sensor reader (270) of the present example also includes a communication port (276) that is configured to communicate data from sensor reader (270) to an external device. For instance, communication port (276) may communicate biomarker related data to a desktop computer, laptop computer, smartphone, computer network, hospital mainframe, and/or other device/system that may be used by a user and/or computer to view and/or process biomarker related information. As another merely illustrative example, communication port (276) may communicate data from sensor reader (270) to another medical device, such as a surgical instrument (e.g., any of the devices referred to in section V.B.1, section V.B.2, or section V.D., below, etc.), an implanted device (e.g., any of the devices referred to in section V.C., below, etc.), an/or any other type of device. Communication port (276) may be configured to provide such communication via wire and/or wirelessly. It should also be understood that communication port (276) may be configured to receive incoming communications from an external device. For instance, communication port (276) may receive firmware updates for processing hardware (272), additional tables or other data for storage on storage medium (274), etc. Various other suitable configurations, operabilities, and uses for communication port (276) will be apparent to those of ordinary skill in the art in view of the teachings herein. It should also be understood that, as with other components described herein, communication port (276) is merely optional and may simply be omitted if desired.

Biomarker processing module (230) of the present example also includes a graphical user interface (280) that is coupled with sensor reader (270). Graphical user interface (280) may thus be configured to present biomarker related information to a user. For instance, in accordance with block (60) of FIG. 1, graphical user interface (280) may indicate to the user which kind of therapeutic agent to administer to the patient, based on biomarker data obtained by biomarker processing module (230). In addition or in the alternative, in accordance with block (70) of FIG. 1, graphical user interface (280) may indicate to the user which kind of surgical instrument to use on the patient, based on biomarker data obtained by biomarker processing module (230). In addition or in the alternative, in accordance with block (80) of FIG. 1, graphical user interface (280) may indicate to the user which kind of adjustments should be made to a surgical instrument that will be used on the patient, based on biomarker data obtained by biomarker processing module (230). In addition or in the alternative, in accordance with block (90) of FIG. 1, graphical user interface (280) may indicate to the user which kind of surgical technique to use on a patient, based on biomarker data obtained by biomarker processing module (230). Other suitable types of information that may be presented to a user via graphical user interface (280) will be apparent to those of ordinary skill in the art in view of the teachings herein. It should also be understood that graphical user interface (280) may be configured to receive input from the user, including but not limited to programming of processing hardware (272), selection of which biomarkers to detect, etc. Again, though, as with other components described herein, graphical user interface (280) is merely optional and may simply be omitted if desired.

As with other components of system (200), the foregoing components, features, configurations, and operabilities of biomarker processing module (230) are merely illustrative examples. It should be understood that biomarker processing module (230) may alternatively have any other suitable components, features, configurations, and/or operabilities. Other suitable components, features, configurations, and operabilities that may be provided in biomarker processing module (230) will be apparent to those of ordinary skill in the art in view of the teachings herein.

B. Exemplary Systems for Making Adjustments to Surgical Instruments/Techniques Based on Biomarker Feedback As noted above, feedback received through monitoring, analysis, or other processing of biomarkers as described herein may be used to make adjustments during a surgical procedure. In some situations, such adjustments may be made in real time or in near-real time during the surgical procedure. Furthermore, some such adjustments may be automated as will be described in greater detail below. By way of example only, surgical adjustments made in response to biomarkers may include any or all of the following: adjusting the administration of active and/or therapeutic agents; adjusting the operating parameters of a surgical instrument; and/or adjusting the technique by which a surgical instrument is used by a surgeon during a procedure. Several examples of ways in which surgical systems may provide adjustments based at least in part on biomarker feedback are shown in FIGS. 8-11 and are described in greater detail below, while various other examples will be apparent to those of ordinary skill in the art in view of the teachings herein.

It should also be understood that biomarker influenced adjustments as described below may be made based on various techniques for processing biomarker data. For instance, an adjustment may be made when one or more detected biomarker levels exceed a threshold. It should also be understood that adjustments may be made based on linear or nonlinear combinations of several detected biomarker levels. For instance, control algorithms may provide one or more scores based on various permutations of detected biomarker levels, and such scores may be used to provide adjustments as described below. Various suitable ways in which control algorithms may be formulated and based on various biomarker data points will be apparent to those of ordinary skill in the art in view of the teachings herein.

Figure 8:
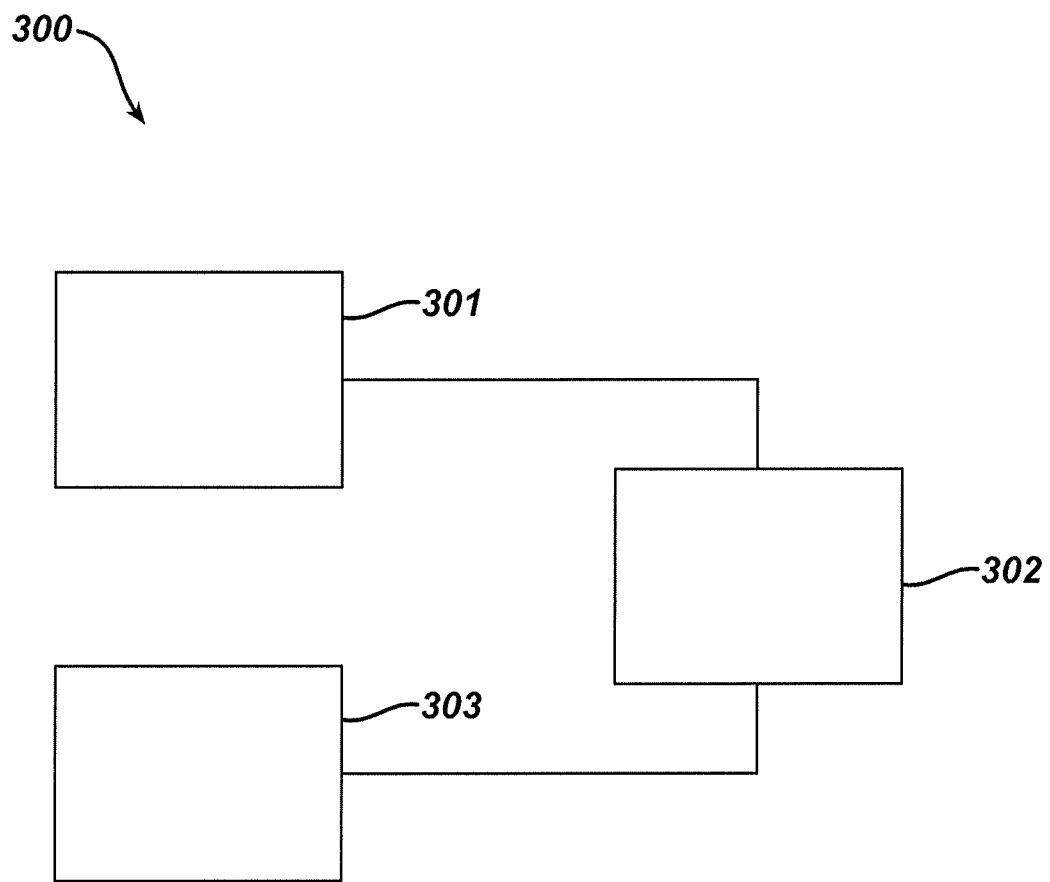
FIG. 8 depicts a schematic view of an exemplary surgical instrument system including biomarker sensor feedback, where the biomarker sensor feedback is used to automatically control or adjust a surgical instrument.

1. Exemplary System for Automatic Adjustments to Surgical Instrument Based on Biomarker Feedback As shown in FIG. 8, a surgical system (300) includes a biomarker sensor (301), a control module (302), and a surgical instrument (303). Surgical system (300) of this example provides control of surgical instrument (303) based at least in part on biomarker expressions detected by biomarker sensor (301). Biomarker sensor (301) is in communication with control module (302), and is operable to communicate sensed biomarker data to control module (302). Control module (302) is in communication with surgical instrument (303), and is operable to control surgical instrument (303) based at least in part on biomarker data communicated from biomarker sensor (301). While FIG. 8 shows biomarker sensor (301), control module (302), and surgical instrument (303) as separate components, it should be understood that one or more of these components may in fact be integrated into a single device. For instance, biomarker sensor (301) and control module (302) may be integral components of surgical instrument (303). As another merely illustrative example, control module (302) may be an integral component of surgical instrument (303) while biomarker sensor (301) is a separate component that is nevertheless in communication with control module (302). The components shown in FIG. 1 may also be provided in plural form. For instance, surgical system (300) may include two control modules (302)—one directly associated with biomarker sensor (301) and another directly associated with instrument (303)—with those two control modules (302) being in communication with each other. It should also be understood that communication between components may be provided in various ways, including but not limited to wired, wireless, or combinations of wired and wireless.

Biomarker sensor (301) may take a variety of forms. By way of example only, biomarker sensor (301) may comprise one or more of the following: a biochip array, an immunoassay device, a spectrophotometry device, a mass spectrometry device, a chromatography device, a radioactivity measuring device, and/or any other suitable device or combination of devices. In some versions, biomarker sensor (301) monitors just one type of biomarker. In some other versions, biomarker sensor (301) monitors more than one type of biomarker. For instance, biomarker sensor (301) may be configured to simultaneously monitor expressions of various biomarkers. Regardless of whether biomarker sensor (301) is used to detect expressions of just one biomarker or more than one biomarker, the type(s) of biomarker(s) detected by biomarker sensor (301) may include (but need not be limited to) any of the types of biomarkers referred to herein. It should also be understood that biomarker sensor (301) may include any or all of the components of biomarker processing module (230) and/or possible components. Other forms that biomarker sensor (301) may take will be apparent to those of ordinary skill in the art in view of the teachings herein.

Control module (302) may also take a variety of forms. In some versions, control module (302) comprises an integral component of instrument (303), such that control module (302) is located on or within instrument (303). In some other versions, control module (302) is located within a piece of capital equipment that is coupled with instrument (303). In still other versions, control module (302) is formed by a combination of one or more components located on or within instrument (303) as well as one or more component located on or within a piece of capital equipment that is coupled with instrument (303). By way of example only, control module (302) may comprise a processor, such as a conventional microprocessor or chip; or some other type of processor (e.g., conventional, customized, etc.). Control module (302) may also comprise a memory, such as a flash memory device, a memory chip, or some other type of memory. For instance, system (300) may be configured such that a biomarker related response should be provided through instrument (303) only when a certain biomarker level (or certain combination of levels of different biomarkers) exceeds or falls below a threshold level. Thus, a processor in control module (302) may include a control logic configured to compare biomarker data from biomarker sensor (301) against one or more threshold values stored in the memory of control module (302), and only trigger a response through instrument (303) when the biomarker data from biomarker sensor (301) exceeds or falls below threshold data stored on the memory of control module (302); and/or when the biomarker data otherwise meets some criteria defined in the memory.

In some other versions, biomarker data is not compared against one or more baselines stored in memory in control module (302). For instance, biomarker sensor (301) may have a preconfigured sensitivity such that it simply does not detect biomarker data (or does not otherwise communicate biomarker data to control module (302)) unless one or more biomarker expression values exceed or fall below a threshold. Still other suitable relationships between biomarker sensor (301) and control module (302), as well as various other ways in which control module (302) may process and react to biomarker data from biomarker sensor (301), will be apparent to those of ordinary skill in the art in view of the teachings herein.

Instrument (303) may comprise any of the types of surgical instruments referred to herein. Alternatively, instrument (303) may comprise any other suitable type of surgical instrument. In versions where instrument (303) has an end effector that contacts the patient's tissue during performance of a surgical procedure, it should be understood that biomarker sensor (301) may be incorporated into or near such an end effector or otherwise be in communication with one or more features of end effector. In some versions, instrument (303) comprises an electrosurgical instrument (e.g., monopolar or bipolar) having an end effector that is configured to cut and coagulate tissue. In some such versions, control module (302) is configured to adjust the frequency and/or power level of energy that is applied through the end effector, based on biomarker feedback obtained through biomarker sensor (301). For instance, such biomarker feedback may relate to biomarker expressions associated with thermal damage to tissue, coagulation of blood, etc. Such adjustments may be made in real time or in near-real time (e.g., control module (302) responsively adjusts frequency and/or power level of instrument (303) immediately after processing biomarker data from sensor (301), etc.).

In some other versions, instrument comprises an ultrasonic instrument having an end effector that is configured to cut and coagulate tissue. Again, control module (302) may be configured to adjust the frequency and/or power level of energy that is applied through the end effector, based on biomarker feedback obtained through biomarker sensor (301). And again, such biomarker feedback may relate to biomarker expressions associated with thermal damage to tissue, coagulation of blood, etc. And as with the electrosurgical example, such ultrasonic adjustments may be made in real time or in near-real time (e.g., control module (302) responsively adjusts frequency and/or power level of instrument (303) immediately after processing biomarker data from sensor (301), etc.).

As a merely illustrative example, biomarker sensor (301) may be configured to monitor levels of Tumor Necrosis Factor alpha (TNF-α), one of the earliest mediators of an inflammatory response. If biomarker sensor (301) reports a level of (TNF-α) greater than previously observed historical norms, then control module (302) could decrease the energy supplied to the surgical device (303). As another merely illustrative example, biomarker sensor (301) may be configured to measure TNF-α, and control module (302) or some other feature may be configured to measure tissue electrical resistance. If control module (302) observes that either TNF-α levels or tissue electrical resistance are beyond historical norms, then control module (302) can decrease energy being supplied to the surgical device (303). As yet another merely illustrative example, biomarker sensor (301) may be configured to measure TNF-α, and control module (302) or some other feature may be configured to measure pulse rate. If control module (302) observes that either TNF-α levels or pulse rate are beyond historical norms, then control module (302) can decrease energy being supplied to surgical device (303).

Still other suitable forms that instrument (303) may take will be apparent to those of ordinary skill in the art in view of the teachings herein. Similarly, other ways in which a biomarker sensor (301) may be used to adjust the operating parameters of a surgical instrument (303), in real time or otherwise, will be apparent to those of ordinary skill in the art in view of the teachings herein.

Figure 9:
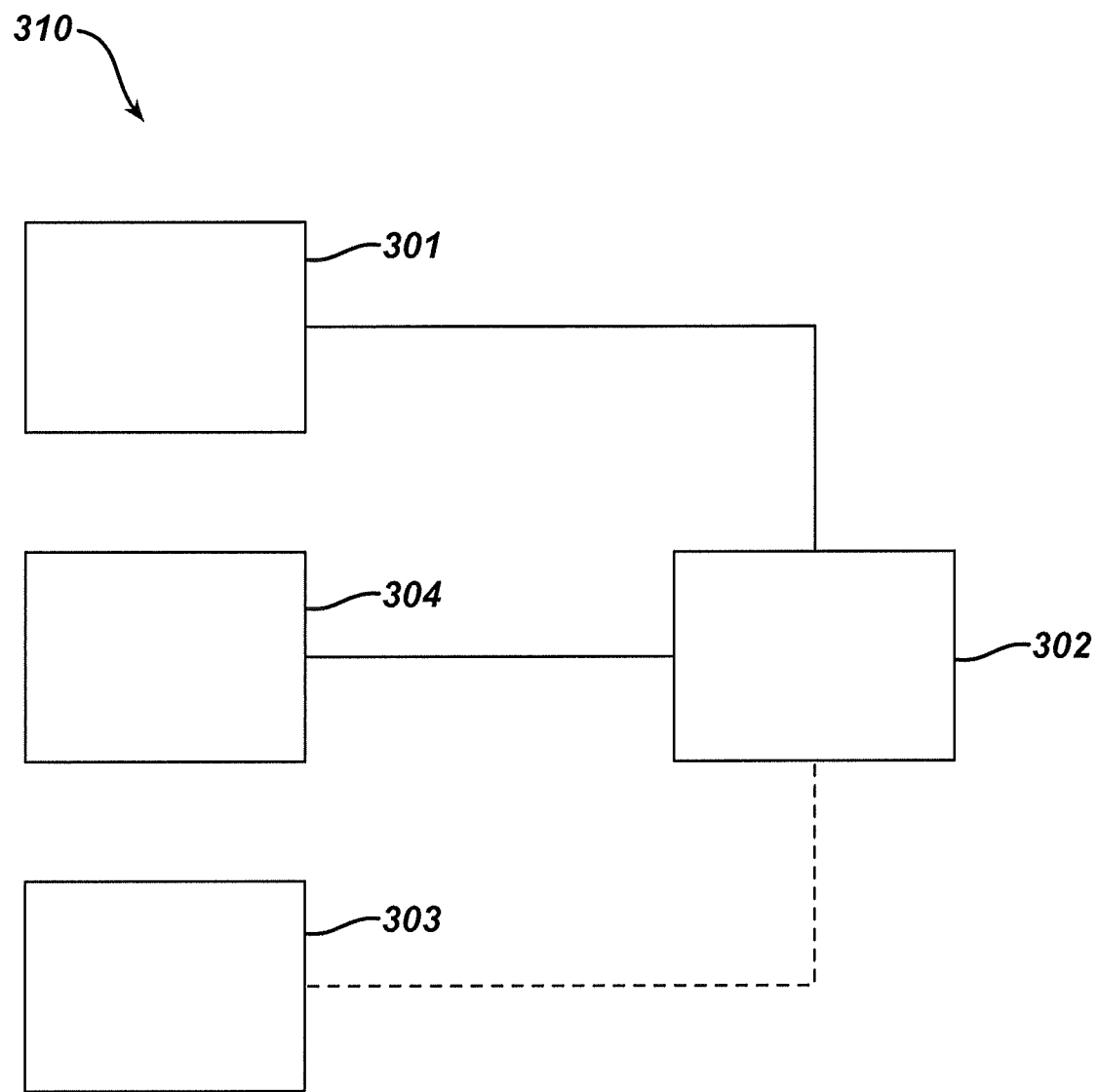
FIG. 9 depicts a schematic view of another exemplary surgical instrument system including biomarker sensor feedback, where the biomarker sensor feedback is used to control an agent administration device.

2. Exemplary System for Automatic Administration of Therapy Based on Biomarker Feedback FIG. 9 shows a surgical system (310) that includes a biomarker sensor (301), a control module (302), a surgical instrument (303), and an agent administration device (304). Surgical system (310) of this example provides control of agent administration device (304) based at least in part on biomarker expressions detected by biomarker sensor (301). Biomarker sensor (301) is in communication with control module (302), and is operable to communicate sensed biomarker data to control module (302). Control module (302) is in communication with agent administration device (304), and is operable to control agent administration device (304) based at least in part on biomarker data communicated from biomarker sensor (301). Optionally, control module (302) may also be in communication with surgical instrument (303), much like in the example of surgical system (300) described above.

While FIG. 9 shows biomarker sensor (301), control module (302), surgical instrument (303), and agent administration device (304) as separate components, it should be understood that one or more of these components may in fact be integrated into a single device. For instance, biomarker sensor (301), control module (302), and agent administration device (304) may be integral components of surgical instrument (303). As another merely illustrative example, biomarker sensor (301) and control module (302) may be an integral component of agent administration device (304) while instrument (303) is a completely separate component that is not even in communication with control module (302). The components shown in FIG. 9 may also be provided in plural form. For instance, surgical system (310) may include two control modules (302)—one directly associated with biomarker sensor (301) and another directly associated with agent administration device (304)—with those two control modules (302) being in communication with each other. It should also be understood that communication between components may be provided in various ways, including but not limited to wired, wireless, or combinations of wired and wireless.

Biomarker sensor (301) may take a variety of forms. By way of example only, biomarker sensor (301) may be configured in accordance with the teachings provided above in the context of surgical system (300). Control module (302) may also take a variety of forms. By way of example only, control module (302) may be configured in accordance with the teachings provided above in the context of surgical system (300). In some versions, control module (302) controls agent administration device (304) based at least in part on biomarker data communicated from biomarker sensor (301); such as when biomarker data from biomarker sensor (301) exceeds or falls below one or more threshold values and/or when the biomarker data otherwise meets some predefined criteria. Control module (302) may also control instrument (303) based at least in part on biomarker data communicated from biomarker sensor (301); such as when biomarker data from biomarker sensor (301) exceeds or falls below one or more threshold values and/or when the biomarker data otherwise meets some predefined criteria. Still other suitable relationships between biomarker sensor (301) and control module (302), as well as various other ways in which control module (302) may process and react to biomarker data from biomarker sensor (301), will be apparent to those of ordinary skill in the art in view of the teachings herein.

Instrument (303) may also take a variety of forms. By way of example only, instrument (303) may be configured in accordance with the teachings provided above in the context of surgical system (300). For instance, instrument (303) may comprise any of the types of surgical instruments referred to herein. In versions where instrument (303) has an end effector that contacts the patient's tissue during performance of a surgical procedure, it should be understood that biomarker sensor (301) may be incorporated into or near such an end effector or otherwise communicate with a component at or near end effector. In some versions, control module (302) is configured to control instrument (303) based at least in part on biomarker data communicated from biomarker sensor (301), as in the examples described above in the context of surgical system (300). Such operability may be provided in addition to control module (302) controlling agent administration device (304) based at least in part on biomarker data communicated from biomarker sensor (301). Alternatively, control module (302) may just control agent administration device (304) in some versions, without also controlling instrument (303). In some such versions, instrument (303) may be controlled in any suitable conventional fashion.

Agent administration device (304) may comprise a variety of types of devices that are operable to administer an active agent and/or a therapeutic agent to a surgical site. For instance, agent administration device (304) may include some type of reservoir or other component containing the agent, a nozzle or output port that is configured to dispense the agent at the surgical site, and a pump or other component that is operable to drive the agent from the reservoir through the nozzle or port to the surgical site. In versions where instrument (303) has an end effector or other component that is placed into contact with or near tissue in a patient, a nozzle or output port of agent administration device (304) may be positioned on or near such an end effector or other component of instrument (303). Agent administration device (304) may therefore administer one or more agents at an incision (before, during, and/or after the incision is created) and/or at some other type of surgical site. For instance, instrument (303) and/or agent administration device (304) may be constructed in accordance with any of the teachings provided below in section V.D. The agent contained in agent administration device (304) may comprise coagulation agents, vasoconstrictors, anti-inflammatory agents, cell specific chemotactic agents, corticosteroids, NSAIDs, DNA, and/or any other suitable type of agent(s). Other suitable agents that may be contained in agent administration device (304) will be apparent to those of ordinary skill in the art in view of the teachings herein.

It should also be understood that agent administration device (304) may contain more than one type of agent. In particular, agent administration device (304) and control module (302) may be configured such that particular agents and/or combinations of agents are selected and administered through agent administration device (304) based on biomarker expressions detected through biomarker sensor (301). For instance, certain biomarker expressions may warrant administrations of a certain agent or a certain combination of agents. Control module (302) may include a memory storing "prescriptions" of agents, and a processor in control module (302) may include a control logic that is configured to compare biomarker data from biomarker sensor (301) against such prescriptions and select the prescription that best fits the biomarker data received from biomarker sensor (301). Control module (302) may then execute the selected prescription by commanding agent administration device (304) to administer one or more agents to the surgical site, based on the selected prescription. Regardless of whether agent administration device (304) simply provides one type of agent or allows selection of more than one agent based on a prescription, etc., administration of agents through agent administration device (304) may be provided in real time or in near-real time (e.g., control module (302) responsively commands agent administration device (304) to administer one or more agents immediately after processing biomarker data from sensor (301), etc.).

As a merely illustrative example, biomarker sensor (301) may be designed to measure total reactive oxygen species. If control module (302) observes a higher level of total reactive species than desired according to historical norms measured by biomarker sensor (301), then control module (302) can either decrease the energy to surgical device (303) or release an antioxidizing agent, such as ascorbic acid, from administration device (304), or both. Another merely illustrative example would be where biomarker sensor (301) and agent administration device (304) are implanted at the surgical site (or catheter ports are implanted and in communication with an extracorporeal device). Biomarker sensor (301) then measures specific biomarkers for biological processes such as inflammation and then instructs agent administration device (304) to release anti inflammatory agents based on the level of biomarker identified. Still other suitable forms that agent administration device (304) may take (e.g., components, configurations, operability, etc.) will be apparent to those of ordinary skill in the art in view of the teachings herein. Similarly, other ways in which a biomarker sensor (301) may be used to control an agent administration device (304), in real time or otherwise, will be apparent to those of ordinary skill in the art in view of the teachings herein.

Figure 10:
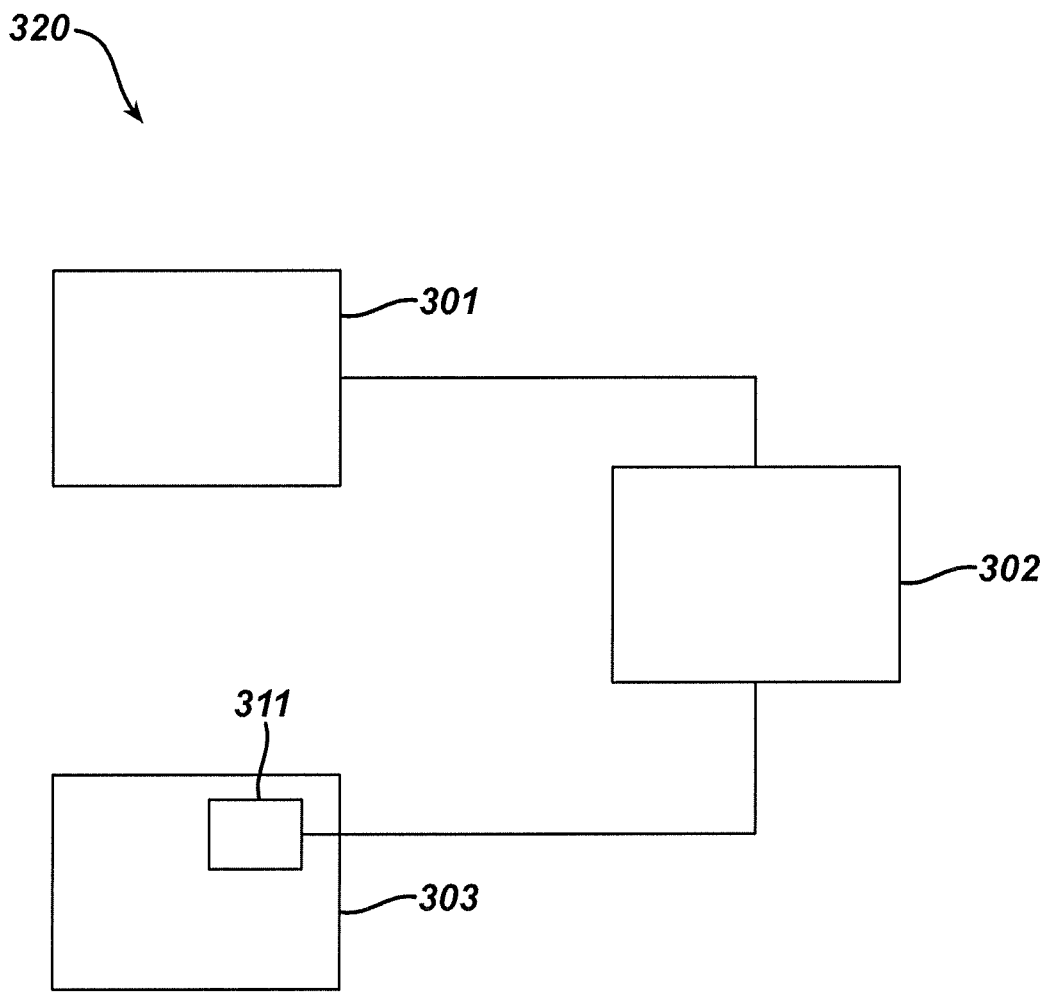
FIG. 10 depicts a schematic view of another exemplary surgical instrument system including biomarker sensor feedback, where biomarker sensor feedback is provided to the user through a user feedback feature of a surgical instrument.

3. Exemplary System for Biomarker Feedback to User Via a Surgical Instrument Feature FIG. 10 shows a surgical system (320) that includes a biomarker sensor (301), a control module (302), and a surgical instrument (303). Surgical system (320) of this example provides user feedback to a surgeon operating instrument (303), based at least in part on biomarker expressions detected by biomarker sensor (301). Biomarker sensor (301) is in communication with control module (302), and is operable to communicate sensed biomarker data to control module (302). Control module (302) is in communication with surgical instrument (303), and is operable to provide user feedback to a surgeon through instrument (303), based at least in part on biomarker data communicated from biomarker sensor (301). While FIG. 10 shows biomarker sensor (301), control module (302), and surgical instrument (303) as separate components, it should be understood that one or more of these components may in fact be integrated into a single device. For instance, biomarker sensor (301) and control module (302) may be integral components of surgical instrument (303). As another merely illustrative example, control module (302) may be an integral component of surgical instrument (303) while biomarker sensor (301) is a separate component that is nevertheless in communication with control module (302). The components shown in FIG. 10 may also be provided in plural form. For instance, surgical system (320) may include two control modules (302)—one directly associated with biomarker sensor (301) and another directly associated with instrument (303)—with those two control modules (302) being in communication with each other. It should also be understood that communication between components may be provided in various ways, including but not limited to wired, wireless, or combinations of wired and wireless.

Biomarker sensor (301) may take a variety of forms. By way of example only, biomarker sensor (301) may be configured in accordance with the teachings provided above in the context of surgical system (300). Control module (302) may also take a variety of forms. By way of example only, control module (302) may be configured in accordance with the teachings provided above in the context of surgical system (300). Instrument (303) of the present example includes a user feedback feature (311), which is in communication with control module (302). User feedback feature (311) is configured to provide the surgeon with some form of feedback during use of instrument (303). Such feedback may include audio, visual, and/or tactile feedback. For instance, user feedback feature (311) may include one or more LEDs and/or other type(s) of visual feedback device; a speaker and/or other type(s) of audio feedback device; and/or a vibrating device and/or other type(s) of tactile feedback device. User feedback feature (311) may provide one or more of the various kinds of feedback described above with reference to graphical user interface (280) and/or various other kinds of feedback.

In some versions, control module (302) controls user feedback feature (311) of instrument (303) based at least in part on biomarker data communicated from biomarker sensor (301); such as when biomarker data from biomarker sensor (301) exceeds or falls below one or more threshold values and/or when the biomarker data otherwise meets some predefined criteria. Control module (302) may also control operational parameters of instrument (303) (e.g., frequency and/or power of energy applied through instrument (303), etc.) based at least in part on biomarker data communicated from biomarker sensor (301); such as when biomarker data from biomarker sensor (301) exceeds or falls below one or more threshold values and/or when the biomarker data otherwise meets some predefined criteria. Still other suitable relationships between biomarker sensor (301) and control module (302), as well as various other ways in which control module (302) may process and react to biomarker data from biomarker sensor (301), will be apparent to those of ordinary skill in the art in view of the teachings herein.

In addition to including user feedback feature (311), instrument (303) may be configured in accordance with the teachings provided above in the context of surgical system (300). For instance, instrument (303) may comprise any of the types of surgical instruments referred to herein. In versions where instrument (303) has an end effector that contacts the patient's tissue during performance of a surgical procedure, it should be understood that biomarker sensor (301) may be incorporated into or near such an end effector or otherwise communicate with a component at or near end effector. In some versions, control module (302) is configured to control operational parameters of instrument (303) (e.g., frequency and/or power of energy applied through instrument (303), etc.), based at least in part on biomarker data communicated from biomarker sensor (301), as in the examples described above in the context of surgical system (300). Such operability may be provided in addition to control module (302) controlling user feedback feature (311) based at least in part on biomarker data communicated from biomarker sensor (301). Alternatively, control module (302) may just control user feedback feature (311) in some versions, without also controlling operational parameters of instrument (303). In some such versions, operational parameters of instrument (303) may be controlled in any suitable conventional fashion.

In the present example, it is up to the surgeon (or some other person) to react in accordance with feedback provided through user feedback feature (311). For instance, the surgeon may alter the technique through which he or she is using instrument (303) in the surgical procedure, based at least in part on biomarker related feedback provided through user feedback feature (311). As a merely illustrative example, biomarker sensor (301) may be "tuned" to detect biomarkers associated with cancerous tumors. As a surgeon is operating near a cancerous tumor (e.g., to excise the tumor), it may be undesirable to sever, pierce, or otherwise compromise the structural integrity of the tumor itself with the surgical instrument. Thus, a biomarker sensor (301) that is tuned to detect biomarkers associated with cancerous tumors may sense when a blade or other component of a surgical instrument is getting too close to a tumor and may trigger an audio and/or visual alarm to the surgeon via user feedback feature (311) in real time or near-real time to inform the surgeon that they are getting too close to the tumor. The surgeon may alter his or her approach accordingly.

In addition or in the alternative, the surgeon (or some other person) may manually adjust the operating parameters of instrument (303), based at least in part on biomarker related feedback provided through user feedback feature (311). For instance, the surgeon (or some other person) may manipulate control features on instrument (303) and/or control features of a piece of capital equipment that is coupled with instrument (303) in response to biomarker related feedback provided through user feedback feature (311). It should be understood that feedback may be provided to the surgeon through user input feature (305) in real time or near-real time. The surgeon (or other person) may thus alter the technique through which he or she is using instrument (303) in the surgical procedure and/or manually adjust the operating parameters of instrument (303) in real time or near-real time, based at least in part on biomarker related feedback provided through user feedback feature (311).

Figure 11:
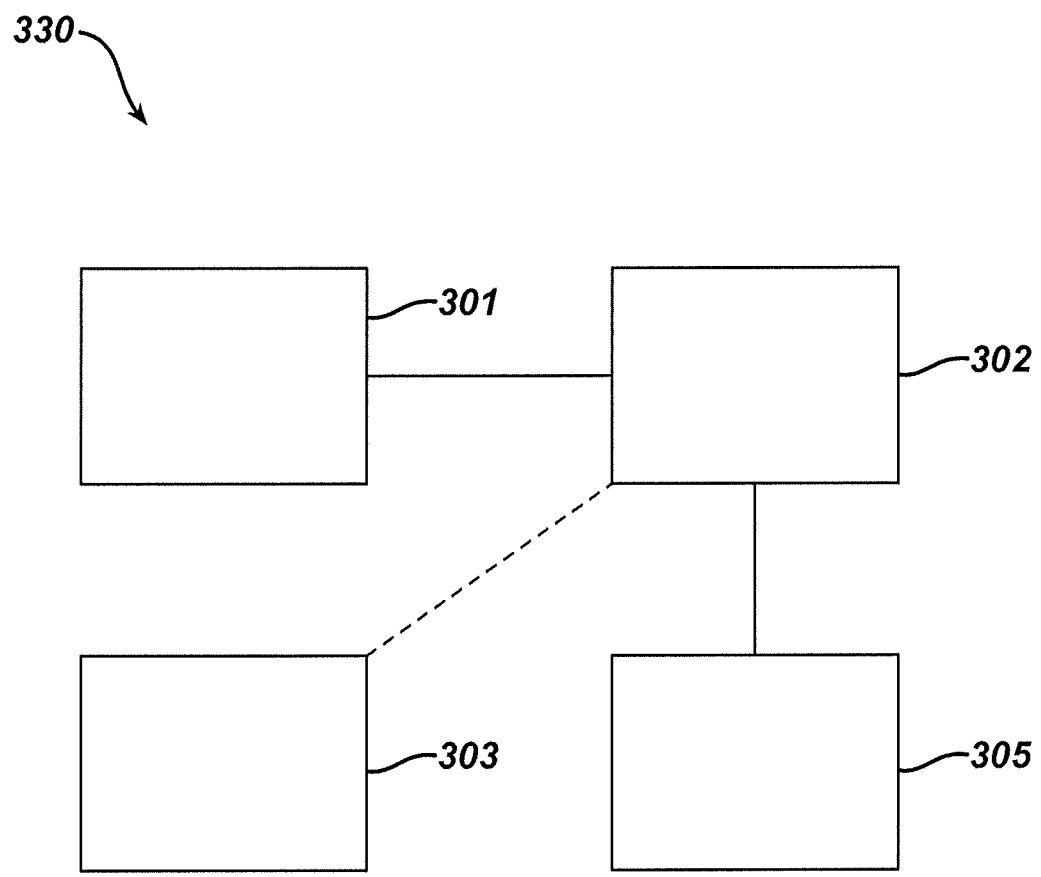
FIG. 11 depicts a schematic view of another exemplary surgical instrument system including biomarker sensor feedback, where biomarker sensor feedback is provided to the user through a dedicated user feedback device.

4. Exemplary System for Biomarker Feedback to User Via a Separate User Interface FIG. 11 shows an example of a surgical system (330) that is essentially a variation of surgical system (320) described above. In particular, surgical system (330) includes a biomarker sensor (301), a control module (302), and a surgical instrument (303). Surgical system (330) of this example also provides user feedback to a surgeon operating instrument (303), based at least in part on biomarker expressions detected by biomarker sensor (301). However, system (330) of this example includes a separate user feedback device (305) instead of having a user feedback feature (311) incorporated into instrument (303). In this example, biomarker sensor (301) is in communication with control module (302), and is operable to communicate sensed biomarker data to control module (302). Control module (302) is in communication with user feedback device (305), and is operable to control user feedback device (305) based at least in part on biomarker data communicated from biomarker sensor (301). Optionally, control module (302) may also in communication with surgical instrument (303), much like in the example of surgical system (300) described above.

While FIG. 11 shows biomarker sensor (301), control module (302), and surgical instrument (303) as separate components, it should be understood that one or more of these components may in fact be integrated into a single device. For instance, biomarker sensor (301) and control module (302) may be integral components of surgical instrument (303). As another merely illustrative example, control module (302) may be an integral component of surgical instrument (303) while biomarker sensor (301) is a separate component that is nevertheless in communication with control module (302). The components shown in FIG. 11 may also be provided in plural form. For instance, surgical system (330) may include two control modules (302)—one directly associated with biomarker sensor (301) and another directly associated with instrument (303). It should also be understood that communication between components may be provided in various ways, including but not limited to wired, wireless, or combinations of wired and wireless.

Biomarker sensor (301) may take a variety of forms. By way of example only, biomarker sensor (301) may be configured in accordance with the teachings provided above in the context of surgical system (300). Control module (302) may also take a variety of forms. By way of example only, control module (302) may be configured in accordance with the teachings provided above in the context of surgical system (300). Similarly, instrument (303) may take any suitable form. For instance, instrument (303) may be configured in accordance with the teachings provided above in the context of surgical system (300). In addition, biomarker sensor (301) may be incorporated into instrument (303) as described herein, if desired. It should also be understood that the relationships and interoperability between control module (302) and user feedback device (305) may be the same as the relationships and interoperability between control module (302) and user feedback feature (311) described above. Alternatively, control module (302) and user feedback device (305) may have any other suitable relationships and interoperability.

User feedback device (305) may also take a variety of forms. Like user feedback feature (311) described above, user feedback device (305) is configured to provide the surgeon with some form of feedback during use of instrument (303). Such feedback may include audio, visual, and/or tactile feedback. By way of example only, user feedback device (305) may comprise a conventional desktop computer; a conventional laptop computer; a portable electronic device (e.g., BlackBerry, iPhone, etc.); some other type of conventional device operable to provide audio, visual, and/or tactile feedback to a user; a customized device operable to provide audio, visual, and/or tactile feedback to a user; and/or any other suitable type of device(s), including combinations thereof. In addition, user feedback device (305) (or some other component in communication with user feedback device (305)) may be configured to store biomarker related data and/or communicate such data over a network to another location, such as for further analytical purposes, statistical purposes, and/or educational purposes, etc.

As with user feedback feature (311) described above, the surgeon (or some other person) may react in accordance with feedback provided through user feedback device (305). For instance, the surgeon may alter the technique through which he or she is using instrument (303) in the surgical procedure, based at least in part on biomarker related feedback provided through user feedback device (305). As a merely illustrative example, the cancerous tumor example provided above with respect to user feedback feature (311) may be equally applicable for user feedback device (305). In addition or in the alternative, the surgeon (or some other person) may manually adjust the operating parameters of instrument (303), based at least in part on biomarker related feedback provided through user feedback device (305). For instance, the surgeon (or some other person) may manipulate control features on instrument (303) and/or control features of a piece of capital equipment that is coupled with instrument (303) in response to biomarker related feedback provided through user feedback device (305). It should be understood that feedback may be provided to the surgeon through user input device (305) in real time or near-real time. The surgeon (or other person) may thus alter the technique through which he or she is using instrument (303) in the surgical procedure and/or manually adjust the operating parameters of instrument (303) in real time or near-real time, based at least in part on biomarker related feedback provided through user feedback device (305).

In some versions of system (330), surgical instrument (303) is operated by a surgeon and the surgeon receives feedback through user feedback device (305). However, surgical instrument (303) may be controlled by the patient instead in some versions. For instance, in one merely illustrative alternative example, surgical instrument (303) comprises a patient-controlled iontophoresis device that may be activated by the patient in response to something such as pain. In some such versions, biomarker sensor (301) is configured to sense certain biomarkers such as those associated with the early onset of inflammation. In some versions of this example, user feedback device comprises a portable electronic device such as a cell phone, iPhone, or Blackberry, etc. In addition, control module (302) may be configured to indicate to the patient, through their portable electronic device, to activate their iontophoresis device. Still other ways in which feedback received through monitoring, analysis, or other processing of biomarker expressions as described herein may be used to make adjustments during a surgical procedure, in real time or otherwise, will be apparent to those of ordinary skill in the art in view of the teachings herein. It should be understood from the foregoing that the systems (320, 330) described above with reference to FIGS. 10-11 may be useful in real surgical scenarios with human patients or other types of patients. It should also be understood that the systems (320, 330) described above with reference to FIGS. 10-11 may be useful in surgical training scenarios (e.g., where an instrument (303) is being used in a lab-type setting, etc.). For instance, people training to become surgeons, training to improve their surgical skills, and/or training to learn how to use a particular instrument (303) may be able to use feedback provided through user feedback feature (311) or feedback device (305) to improve their surgical skills and techniques.

Figure 13:
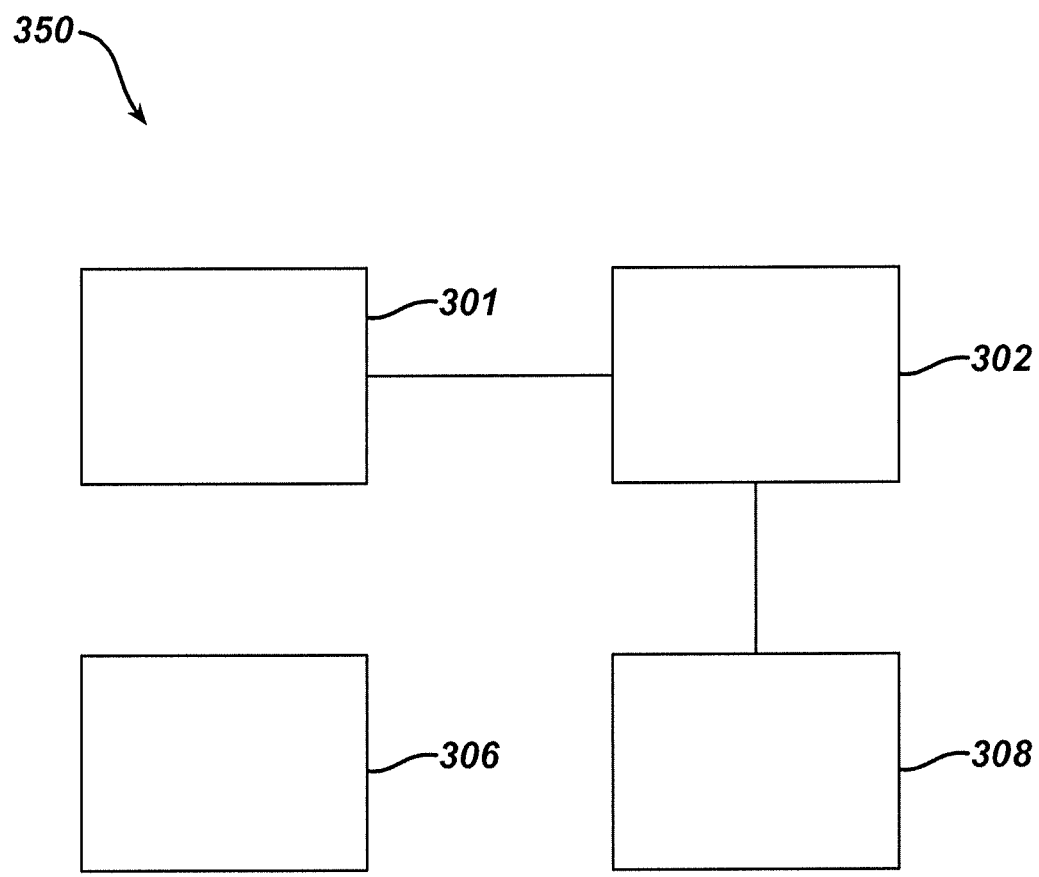
FIG. 13 depicts a schematic view of another exemplary gastric band system including biomarker sensor feedback, where biomarker sensor feedback is used to provide implant-originated feedback to a patient or clinician.
Figure 14:
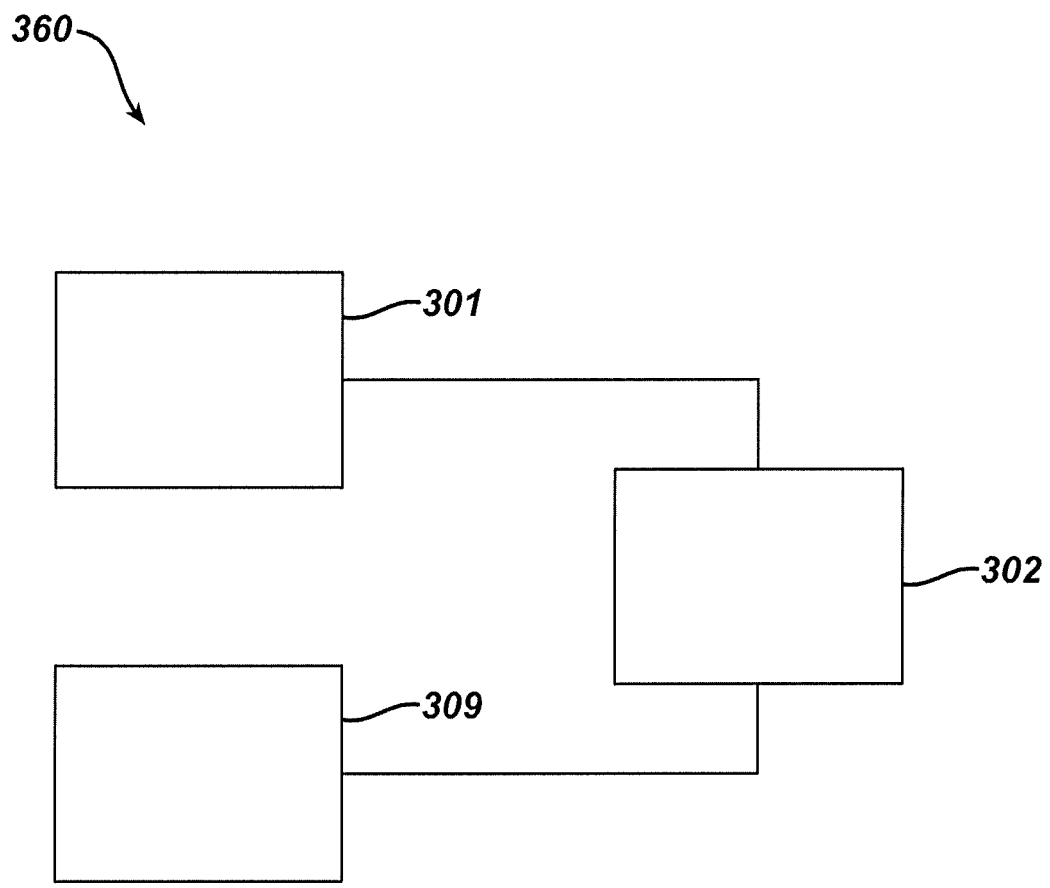
FIG. 14 depicts a schematic view of an exemplary drug infusion system including biomarker sensor feedback, where biomarker sensor feedback is used to provide automatic adjustment of drug delivery by a drug infusion device.

C. Exemplary Systems for Making Adjustments in Medical Implants Based on Biomarker Feedback As another merely illustrative example, feedback received through monitoring, analysis, or other processing of biomarker expressions as described herein may be used to automatically control or otherwise affect the operation of one or more devices that are implanted within a patient. Several examples of ways in which implanted device systems may incorporate biomarker feedback are shown in FIGS. 12-14 and are described in greater detail below, while various other examples will be apparent to those of ordinary skill in the art in view of the teachings herein.

1. Exemplary Automatic Adjustment of Gastric Band Based on Biomarker Feedback

Figure 12:
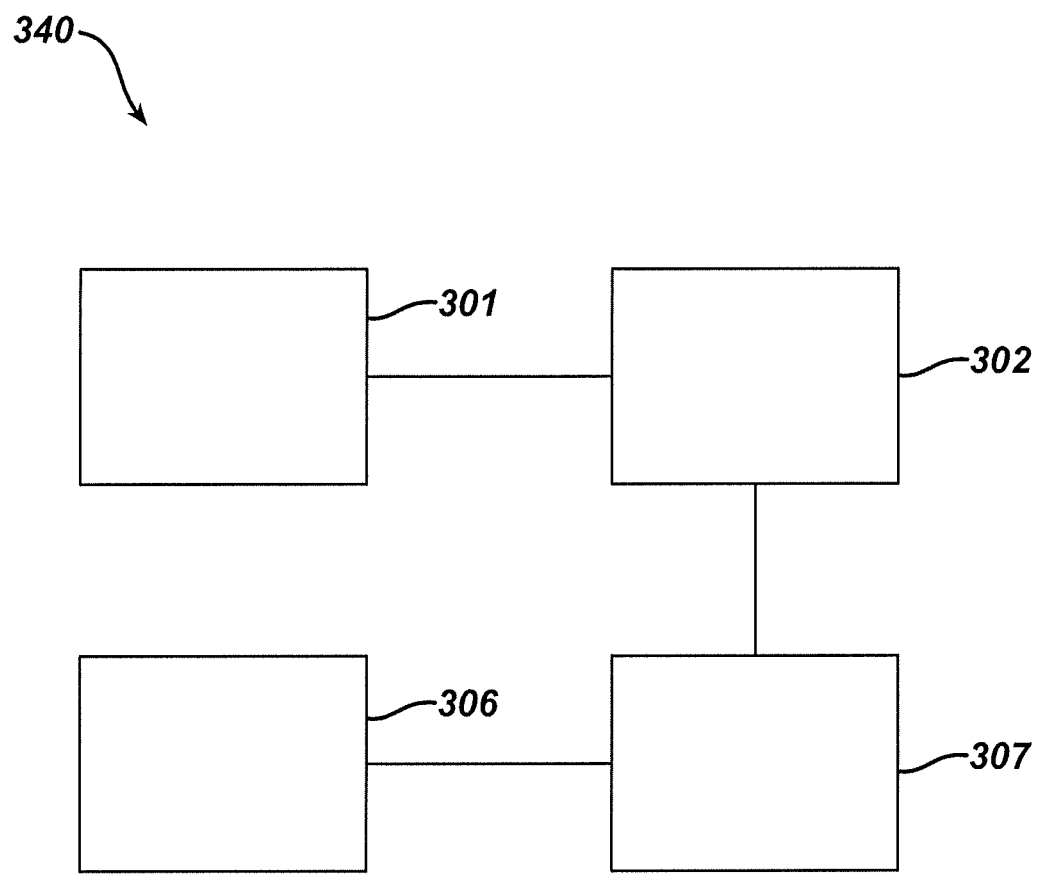
FIG. 12 depicts a schematic view of an exemplary gastric band system including biomarker sensor feedback, where biomarker sensor feedback is used to automatically adjust a gastric band.

FIG. 12 shows an adjustable gastric band system (340) that includes a biomarker sensor (301), a control module (302), an adjustable gastric band (306), and a pump/reservoir system (307). In the present example, biomarker sensor (301), control module (302), adjustable gastric band (306), and pump/reservoir system (307) are all implanted within a patient. Gastric band system (340) of this example provides adjustment of gastric band (306) based at least in part on biomarker expressions detected by biomarker sensor (301). Biomarker sensor (301) is in communication with control module (302), and is operable to communicate sensed biomarker data to control module (302). Control module (302) is in communication with pump/reservoir system (307), and is operable to control pump/reservoir system (307) based at least in part on biomarker data communicated from biomarker sensor (301).

While FIG. 12 shows biomarker sensor (301), control module (302), adjustable gastric band (306), and pump/reservoir system (307) as separate components, it should be understood that one or more of these components may in fact be integrated into a single device. For instance, biomarker sensor (301) may be an integral component of gastric band (306); with control module (302) being an integral component of pump/reservoir system (307). The components shown in FIG. 12 may also be provided in plural form. For instance, surgical system (340) may include two control modules (302)—one directly associated with biomarker sensor (301) and another directly associated with pump/reservoir system (307)—with those two control modules (302) being in communication with each other. It should also be understood that communication between components may be provided in various ways, including but not limited to wired, wireless, or combinations of wired and wireless.

Biomarker sensor (301) may take a variety of forms. By way of example only, biomarker sensor (301) may be configured in accordance with the teachings provided above in the context of surgical system (300). Control module (302) may also take a variety of forms. By way of example only, control module (302) may be configured in accordance with the teachings provided above in the context of surgical system (300). Gastric band (306) may also take a variety of forms. For instance, gastric band (306) may comprise a fluid filled bladder that is coupled with pump/reservoir system (307) via a catheter, forming a closed fluid circuit. Gastric band (306) may be wrapped about a portion of a patient's stomach (e.g., the gastro-esophageal junction), and fluid may be added to the fluid filled bladder to form a food intake restriction stoma within the patient's stomach. Such a restricted stoma may form a pouch in the patient's stomach, above gastric band (306), with such a pouch having a smaller volume than the patient's stomach, such that the patient experiences a relatively early sense of satiety during consumption of food. By way of example only, gastric band (306) may be configured in accordance with the teachings of U.S. Pat. No. 7,416,528, entitled "Latching Device for Gastric Band," issued Aug. 26, 2008, the disclosure of which is incorporated by reference herein. Other suitable forms that gastric band (306) may take will be apparent to those of ordinary skill in the art in view of the teachings herein.

Pump/reservoir system (307) of the present example is operable to selectively add fluid to (or withdraw fluid from) the bladder of gastric band (306), which will in turn affect the degree of restriction created within the patient's stomach by gastric band (306). By way of example only, pump/reservoir system (307) may be configured in accordance with the teachings of U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. As another merely illustrative example, pump/reservoir system (307) may be configured in accordance with the teachings of U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. Other suitable forms that pump/reservoir system (307) may take will be apparent to those of ordinary skill in the art in view of the teachings herein.

In some versions, control module (302) controls pump/reservoir system (307) based at least in part on biomarker data communicated from biomarker sensor (301); such as when biomarker data from biomarker sensor (301) exceeds or falls below one or more threshold values and/or when the biomarker data otherwise meets some predefined criteria. For instance, in some settings it may be desirable to adjust a gastric band (306) based on a degree of irritation of the tissue that is adjacent to gastric band (306) and/or based on some other effect (e.g., strain, abrasion, perforation, etc.) on the tissue that is adjacent to gastric band (306). Accordingly, biomarker sensor (301) may be configured to detect biomarkers associated with such irritation (or other effects); and control module (302) may be configured to control pump/reservoir system (307) to loosen (or tighten) gastric band (306) based on the detection of biomarker expressions that are associated with irritation of (or other effects on) tissue that is adjacent to gastric band (306). Such adjustments may be made in real time, in near-real time, or otherwise.

As another merely illustrative example, it may be desirable in some scenarios to relax the degree of restriction provided by gastric band (306) when the patient is between meals; and/or increase the degree of restriction provided by gastric band (306) when the patient is eating. Accordingly, biomarker sensor (301) may be configured to detect biomarkers associated with fasting and/or consumption. In some such versions control module (302) may be configured to control pump/reservoir system (307) to loosen gastric band (306) based on the detection of biomarker expressions that are associated with fasting and/or tighten gastric band (306) when biomarker expressions that are associated with fasting are no longer detected. In addition or in the alternative, control module (302) may be configured to control pump/reservoir system (307) to tighten gastric band (306) based on the detection of biomarker expressions that are associated with eating and/or loosen gastric band (306) when biomarker expressions that are associated with eating are no longer detected. Again, such adjustments may be made in real time, in near-real time, or otherwise.

As yet another merely illustrative example, it may be desirable in some scenarios to relax the degree of restriction provided by gastric band (306) when the patient is sleeping; and/or increase the degree of restriction provided by gastric band (306) when the patient is awake. Accordingly, biomarker sensor (301) may be configured to detect biomarkers associated with sleep and/or a wakened state. In some such versions control module (302) may be configured to control pump/reservoir system (307) to loosen gastric band (306) based on the detection of biomarker expressions that are associated with sleeping and/or tighten gastric band (306) when biomarker expressions that are associated with sleeping are no longer detected. In addition or in the alternative, control module (302) may be configured to control pump/reservoir system (307) to tighten gastric band (306) based on the detection of biomarker expressions that are associated with the patient being awake and/or loosen gastric band (306) when biomarker expressions that are associated with the patient being awake are no longer detected. Again, such adjustments may be made in real time, in near-real time, or otherwise.

As still another merely illustrative example, it should be understood that a device like a gastric band (306) may be used to address gastroesophageal reflux disease (GERD). For instance, such a band may be placed at or near the bottom of a patient's esophagus, and may be tightened to essentially close off the patient's esophagus during the occurrence of acid reflux to reduce the likelihood of harm to the patient's esophageal tissue that might otherwise occur from the acid reflux. Such a band may also be fluid actuated like gastric band (306), and may be coupled with an analog to pump/reservoir system (307). Accordingly, biomarker sensor (301) may be configured to detect biomarkers associated with irritation (or other effects) to the patient's esophageal tissue associated with acid reflux. In some such versions control module (302) may be configured to control the analog of pump/reservoir system (307) to tighten the band based on the detection of biomarker expressions that are associated with acid reflux loosen the band when biomarker expressions that are associated with acid reflux are no longer detected. Again, such adjustments may be made in real time, in near-real time, or otherwise.

It should also be understood that a gastric band (306) (or band to address acid reflux or some other condition) need not be fluid actuated. For instance, fluid actuated gastric band (306) may be replaced with a mechanically actuated gastric band as described in U.S. Pat. No. 6,067,991, entitled "Mechanical Food Intake Restriction Device," issued May 30, 2000, the disclosure of which is incorporated by reference herein. Of course, with a version gastric band (306) that is not fluid actuated, pump/reservoir system (307) may be eliminated. In some such versions, control module (302) may instead be coupled with a motor or whatever other device drives the mechanically actuated version of gastric band (306), and may selectively tighten or loosen such a gastric band (306) in accordance with the teachings herein. Again, such adjustments may be made in real time, in near-real time, or otherwise.

2. Exemplary Presentation of Implant-Originated Feedback to Patient/Clinician Based on Biomarker Feedback FIG. 13 shows another exemplary gastric band system (350). In this example, gastric band system (350) includes a biomarker sensor (301), a control module (302), an adjustable gastric band (306), and a feedback device (308). In the present example, biomarker sensor (301), control module (302), adjustable gastric band (306), and feedback device (308) are all implanted within a patient. Gastric band system (350) of this example provides feedback to the patient through feedback device (308), based at least in part on biomarker expressions detected by biomarker sensor (301). Biomarker sensor (301) is in communication with control module (302), and is operable to communicate sensed biomarker data to control module (302). Control module (302) is in communication with feedback device (308), and is operable to control feedback device (308) based at least in part on biomarker data communicated from biomarker sensor (301). In this example, gastric band (306) is not coupled with any of biomarker sensor (301), control module (302), or feedback device (308). However, in some versions gastric band (306) may be coupled with any or all of these components, among other components.

Biomarker sensor (301) may take a variety of forms. By way of example only, biomarker sensor (301) may be configured in accordance with the teachings provided above in the context of surgical system (300). Control module (302) may also take a variety of forms. By way of example only, control module (302) may be configured in accordance with the teachings provided above in the context of surgical system (300). Gastric band (306) may also take a variety of forms. By way of example only, gastric band (306) may be configured in accordance with the teachings provided above in the context of gastric band system (340). As merely exemplary alternative, gastric band (306) may include an implanted injection port instead of pump/reservoir system (307), whereby the amount of fluid in gastric band (306) (and hence, the degree of restriction created in the patient's stomach by gastric band (306)) is adjusted using a syringe with a needle inserted in the injection port. For instance, such an injection port may be constructed and operable in accordance with the teachings of U.S. Pub. No. 2005/0283119, entitled "Implantable Medical Device with Reversible Attachment Mechanism and Method," published Dec. 22, 2005, now U.S. Pat. No. 8,007,474, issued Aug. 30, 2011, the disclosure of which is incorporated by reference herein.

Feedback device (308) of the present example is implanted in the patient and may also take a variety of forms. In some versions, feedback device (308) is configured to provide haptic feedback to the patient. For instance, feedback device (308) may include a vibration generator (e.g., similar to a vibration generator in a cell phone, etc.) that is configured to generate vibrations that can be felt by the patient. Feedback device (308) may thus provide the patient with notification of one or more conditions as described in greater detail below. In addition or in the alternative, feedback device (308) may include a communicator that is configured to communicate an alert and/or other information to a location external to the patient. For instance, such a communicator may include a wire passing through the patient's skin to an external device, a coil implanted in the patient that is operable to telemetrically communicate data to a corresponding coil that is external to the patient, or any other type of suitable communication device. Feedback device (308) may thus provide another person or system with notification of one or more conditions as described in greater detail below. In some versions, feedback device (308) is constructed in accordance with the teachings of U.S. patent application Ser. No. 12/640,048, entitled "Implantable Port with Vibratory Feedback," filed Dec. 17, 2009, now U.S. Pat. No. 8,550,981, issued Oct. 8, 2013, the disclosure of which is incorporated by reference herein.

In some versions, control module (302) controls feedback device (308) based at least in part on biomarker data communicated from biomarker sensor (301); such as when biomarker data from biomarker sensor (301) exceeds or falls below one or more threshold values and/or when the biomarker data otherwise meets some predefined criteria. For instance, biomarker sensor (301) may be configured to detect biomarkers associated with tissue irritation or other effects on tissue that may be undesirable and that may be caused by gastric band (306). In versions where feedback device (308) is configured to provide notification to the patient, control module (302) may be configured to control feedback device (308) to alert the patient to the need for gastric band (306) to be adjusted. For instance, feedback device (308) may vibrate in response to biomarker expressions that indicate the need for a gastric band (306) adjustment, and such vibrations may prompt the patient to contact their physician to obtain the adjustment. As another merely illustrative variation, biomarker sensor (301) may be configured to detect biomarker expressions associated with failure of a gastric band (306) (e.g., leakage of fluid from gastric band (306), etc.); and control module (302) may be configured to control feedback device (308) to alert the patient to the need for such failure to be addressed.

As another merely illustrative example, in versions where feedback device (308) is configured to communicate alerts or other information to an external location, feedback device (308) may also be used to communicate the need for an adjustment of gastric band (306). For instance, biomarker sensor (301) may be configured to detect biomarkers associated with tissue irritation or other effects on tissue that may be undesirable and that may be caused by gastric band (306). Control module (302) may be configured to drive feedback device (308) to communicate the need for an adjustment of gastric band (306) to an external device, in response to biomarker expressions that indicate the need for a gastric band (306) adjustment. In some versions, such communications from feedback device (308) include actual biomarker data in addition to an indication that gastric band (306) needs to be adjusted. In some other versions, such communications from feedback device (308) just include an indication that gastric band (306) needs to be adjusted. In still other versions, feedback device (308) simply communicates biomarker data when feedback device (308) is interrogated by an external device (e.g., via transcutaneous wireless telemetry). Thus, communications from feedback device (308) need not only be prompted by a determination from control module (302) that biomarker data as exceeded or fallen below threshold levels or has otherwise met some predefined condition. In other words, an external device may instead make the determination that gastric band (306) needs to be adjusted.

In versions of feedback device (308) that provide wireless communication to an external device, it should be understood that such wireless communication may be provided in various ways. For instance, feedback device (308) may be subject to interrogation by a coil placed adjacent to the patient's skin by a physician during a visit. By way of example only, feedback device (308) may thus be configured and interrogated in accordance with the teachings of U.S. Pub. No. 2006/0189888, entitled "Device for Non-Invasive Measurement of Fluid Pressure in an Adjustable Restriction Device," published Aug. 24, 2006, now U.S. Pat. No. 7,699,770, issued Apr. 20, 2010, the disclosure of which is incorporated by reference herein. As another merely illustrative example, the patient may be provided with a device that is worn externally to the patient and that is in wireless communication with feedback device (308). Such an external device may be configured and operable in accordance with the teachings of U.S. Pub. No. 2006/0199997, entitled "Monitoring of a Food Intake Restriction Device," published Sep. 7, 2006, now U.S. Pat. No. 8,016,745, issued Sep. 13, 2011, the disclosure of which is incorporated by reference herein. Such an external device may thus receive alerts and/or biomarker related data from feedback device (308), and may further communicate such alerts and/or data to a remote computer system and/or to a physician, etc. It should be understood that, in some scenarios, biomarker related data to an external device may not necessarily indicate the need for an adjustment to gastric band (306). For instance, such biomarker related data may be indicative of a patient's compliance with a dietary plan and/or other biological conditions.

It should also be understood that the above-described system architecture and operability of gastric band system (350) may be applied to virtually any type of implanted device. For instance, to the extent that another implanted device has adjustability and the need for an adjustment to the implant can be detected through biomarker expressions, an equivalent to feedback device (308) may be used to notify the patient and/or transmit notification to an external device when an adjustment is needed. Likewise, to the extent that problems associated with another implanted device can be detected through biomarker expressions, an equivalent to feedback device (308) may be used to notify the patient and/or transmit notification to an external device when a problem is detected. Furthermore, in versions where the equivalent to feedback device (308) is capable of communicating with an external device, feedback device (308) may also communicate more than just a notification of a problem (e.g., biomarker data itself, an interpretation of biomarker data, etc.). Of course, data communicated from an equivalent of feedback device (308) to an external device need not be limited to problems associated with an implanted device. For instance, an equivalent of feedback device (308) may communicate any other type of biological data detected through biomarker expressions, including but not limited to biological data relating to effects of an implant or other biological data.

It is also contemplated that an alternative system may include a biomarker sensor (301), a control module (302), and a feedback device (308) without necessarily needing to include any other implanted device. In other words, gastric band (306) may be omitted from system (350), and no other implanted device needs to be provided in place of gastric band (306). It should be appreciated that such systems may be used to detect virtually any type of medical condition and provide communication to the patient, to an external device, to a physician, etc., via feedback device (308). By way of example only, biomarker sensor (301) may be configured to detect biomarker expressions associated with infection (e.g., in a patient that has just undergone a surgical procedure presenting an appreciable risk of infection); to detect biomarker expressions associated with a heart attack (e.g., in a patient that has already had a heart attack or is at a significantly high risk of a heart attack); to detect biomarker expressions associated with hypoglycemia (e.g., in a patient that has diabetes); to detect biomarker expressions associated with cancer (e.g., in a high-risk patient from whom cancerous tumors or lesions have already been removed); or to detect biomarker expressions associated with various other medical/biological conditions. As in system (350) described above, control module (302) may command feedback device (308) when biomarker sensor (301) detects biomarker expressions associated with such medical/biological conditions. As also in system (350) described above, a feedback device (308) so commanded may provide a haptic notification to the patient and/or may communicate the presence of such medical/biological conditions to an external device via wire or wirelessly. Furthermore, like in system (350) described above, such information and/or notifications may be communicated in real time, in near-real time, or in some other suitable fashion. For instance, storage module (302) may store such information and only communicate it after feedback device (308) is interrogated by an external device.

3. Exemplary Automatic Adjustment of Drug Delivery by Drug Infusion System Based on Biomarker Feedback As yet another merely illustrative example, FIG. 14 depicts an exemplary drug infusion system (360) that includes a biomarker sensor (301), a control module (302), and a drug infusion device (309). In the present example, biomarker sensor (301), control module (302), and drug infusion device (309) are all implanted within a patient. Drug infusion system (360) of this example provides administration of drugs through drug infusion device (309) based at least in part on biomarker expressions detected by biomarker sensor (301). Biomarker sensor (301) is in communication with control module (302), and is operable to communicate sensed biomarker data to control module (302). Control module (302) is in communication with pump/reservoir system (307), and is operable to control drug infusion device (309) based at least in part on biomarker data communicated from biomarker sensor (301). While FIG. 14 shows biomarker sensor (301), control module (302), and drug infusion device (309) as separate components, it should be understood that one or more of these components may in fact be integrated into a single device. The components shown in FIG. 14 may also be provided in plural form. It should also be understood that communication between components may be provided in various ways, including but not limited to wired, wireless, or combinations of wired and wireless.

Biomarker sensor (301) may take a variety of forms. By way of example only, biomarker sensor (301) may be configured in accordance with the teachings provided above in the context of surgical system (300). Control module (302) may also take a variety of forms. By way of example only, control module (302) may be configured in accordance with the teachings provided above in the context of surgical system (300). Drug infusion device (309) may comprise any suitable conventional or non-conventional type of drug infusion device. In particular, drug infusion device (309) may include a drug or other type of agent, and may be operable to administer that drug or agent to the patient in a regulated fashion. By way of example only, drug infusion device (309) may contain and administer vasoconstrictors, corticosteroids, NSAIDs, DNA, and/or any other suitable type of agent(s), drugs, and/or other substances. While the term "drug" is used in the phrase "drug infusion device (309)" it is contemplated that drug infusion device (309) may contain and administer various types of substances (e.g., liquids, etc.) that might not necessarily fit within conventional understandings of the term "drug." Such substances may be administered for therapeutic or remedial purposes, for prophylactic or preventative purposes, and/or for any other suitable purpose(s).

In some versions, control module (302) controls drug infusion device (309) based at least in part on biomarker data communicated from biomarker sensor (301); such as when biomarker data from biomarker sensor (301) exceeds or falls below one or more threshold values and/or when the biomarker data otherwise meets some predefined criteria. For instance, drug infusion device (309) may be implanted in a patient to address a particular medical/biological condition. Examples of such conditions, as well as substances that may be administered by drug infusion device (309) to address such conditions, will be apparent to those of ordinary skill in the art in view of the teachings herein. In the present example, biomarker sensor (301) is configured to detect biomarker expressions that relate to the medical/biological condition that drug infusion device (309) is intended to address. Accordingly, control module (302) may be configured to regulate the administration of a drug, agent, or other type of substance by drug infusion device (309), based at least in part on biomarker data obtained by biomarker sensor (301). For instance, control module (302) may increase or decrease the dosage provided to the patient by drug infusion device (309), based at least in part on biomarker data obtained by biomarker sensor (301).

Drug infusion system (360) may also include an equivalent to feedback device (308) as described above. For instance, in contexts where drug infusion device (309) is capable of having its administered substance replenished from an external source (e.g., via injection), feedback device (308) may be configured to communicate to the patient and/or to an external device a need for such substance to be replenished. In addition or in the alternative, feedback device (308) may be configured to communicate to the patient and/or to an external device a notification that drug infusion device (309) is not working properly. As yet another merely illustrative variation, feedback device (308) may be configured to communicate to the patient and/or to an external device an adverse reaction by the patient to a substance administered by drug infusion device (309). In addition or in the alternative, feedback device (308) may be configured to communicate to the patient and/or to an external device any other medical/biological condition that is or is not related to drug infusion device (309). In any of the foregoing examples, information communicated by feedback device (308) may (or may not) be based at least in part on biomarker expressions detected by biomarker sensor (301).

As a merely illustrative example, a sensor device (301) could be designed to measure levels of melatonin. When control module (302) observes levels of melatonin below those of historical norms, control module (302) could increase neurological stimulation provided by an implanted device (303) in order to achieve optimum levels of sedation. Still other ways in which feedback received through monitoring, analysis, or other processing of biomarkers as described herein may be used to automatically control or otherwise affect the operation of one or more devices that are implanted within a patient, in real time or otherwise, will be apparent to those of ordinary skill in the art in view of the teachings herein. Similarly, other ways in which feedback received through monitoring, analysis, or other processing of biomarkers as described herein may be used to detect undesirable conditions within a patient, regardless of whether such conditions are associated with another implanted device, will be apparent to those of ordinary skill in the art in view of the teachings herein. In addition, other ways in which biological conditions detected through the expressions of biomarkers (regardless of whether such biological conditions are desirable or not) may be communicated to a patient and/or to other persons or systems, in real time or otherwise, will be apparent to those of ordinary skill in the art in view of the teachings herein.

D. Exemplary Devices for Administration of Agents Based on Biomarker Feedback or Otherwise As noted above with reference to block (60) of FIG. 1, therapies or treatments may be selected and administered based at least in part on biomarker related information. By way of example only, in some instances, despite the cauterizing capabilities of electrosurgical devices, surgeons may be reluctant to use an electrosurgical device due to the threat of undesired thermal injury that might be caused by some such devices. It may therefore be desirable to provide hemostatic capabilities to a non-electrosurgical cutting device (e.g., a "cold" scalpel) or enhance the existing hemostatic capabilities of a non-electrosurgical cutting device (e.g., a harmonic scalpel). Such hemostatic capabilities may be particularly desirable where biomarker data indicates that a patient has a high propensity to bleed and/or a reduced propensity to clot, etc. Hemostatic capabilities may be provided or enhanced for a non-electrosurgical cutting device by providing the cutting device with the capability of dispensing hemostatic substances. For instance, an unenergized scalpel may be configured to dispense a clotting agent as a mist, flood, or attached flow at the surgical site as the scalpel is being used to cut (and/or after a cut is made with the scalpel). Similarly, a harmonic device may be configured to dispense an aerosol of a clotting agent, which may be dispersed by the vibratory motion of the blade of the harmonic device as the harmonic blade is being used to cut (and/or after a cut is made with the harmonic blade). In addition to or in lieu of clotting agents, vasoconstrictive materials may be employed to give temporary hemostasis that resolves in such a time frame as to enable unimpeded blood flow to healing tissues. Of course, various other types of agents or substances may be administered by a medical device.

The below examples are provided mainly in the context of administering gene therapies in response to biomarker related information as described elsewhere herein (e.g., in accordance with block (60) of FIG. 1). It should be understood, however, that the below teachings may be readily applied to the administration of any other suitable type of therapy or treatment, including but not limited to non-gene therapies or treatments. Various examples of therapies or treatments that may be provided are described elsewhere herein, while still other examples will be apparent to those of ordinary skill in the art in view of the teachings herein. It should also be understood that, while the below teachings are provided in the context of administering therapies or treatments in response to biomarker related information, the below teachings may also be readily applied to the administration of therapies or treatments in response to other information (e.g., from conventional diagnostic techniques) in addition to or in the absence of biomarker related information. In other words, the below teachings are not necessarily limited to the administration of therapies or treatments in response to biomarker related information, as the below teachings may be readily applied to the broader context of administering therapies or treatments in general (e.g., without biomarker related information).

To the extent that therapies or treatments provided in accordance with the below teachings are based on biomarker related information, such biomarker related information may be collected based on the teachings of section V.A. above, based on other teachings herein, and/or based on any other suitable biomarker information collection techniques/devices/systems as will be apparent to those of ordinary skill in the art in view of the teachings herein. Thus, it should be understood that in some versions, a single harmonic device may be used to both obtain biomarker data as described above in section V.A. and administer a gene therapy (or other form of therapy/treatment/etc.) as described below, based at least in part on such biomarker data, and in real time or near-real time. Furthermore, it should be understood that any of the teachings below may be readily combined with any of the teachings provided above in section V.B.2. and/or with any other teachings herein.

The following examples are also provided in the context of a harmonic surgical instrument. It should be understood that, in some versions, harmonic surgical instruments may provide sonoporation capabilities that facilitate gene therapy without the use of viral carriers. In some instances, sonoporation may be used to porate cell nuclei in the patient in addition to porating cell walls in the patient. In addition, transfection rates for gene therapies provided in accordance with the below teachings may be improved by putting the therapeutic DNA/genes in a fat cell (lipid) emulsion. By way of example only, the devices and techniques described below may be provided in accordance with the teachings in Lin et al., "Sonoporation-Mediated Gene Transfer into Adult Rat Dorsal Root Ganglion Cells," Journal of Biomedical Science 17:44 (2010), the disclosure of which is incorporated by reference herein. As another merely illustrative example, the devices and techniques described below may be provided in accordance with the teachings in Negishi, et al., "Delivery of an Angiogenic Gene into Ischemic Muscle by Novel Bubble Liposomes Followed by Ultrasound Exposure," Pharm. Res., DOI 10.1007/s11095-010-0286-4 (2010), the disclosure of which is incorporated by reference herein. As yet another merely illustrative example, the devices and techniques described below may be provided in accordance with the teachings in Taniyama, et al., "Development of Safe and Efficient Novel Nonviral Gene Transfer Using Ultrasound: Enhancement of Transfection Efficiency of Naked Plasmid DNA in Skeletal Muscle," Gene Therapy 9, 372-380 (2002), the disclosure of which is incorporated by reference herein. As still another merely illustrative example, the devices and techniques described below may be provided in accordance with the teachings in Liang, et al., "Optimisation of Ultrasound-Mediated Gene Transfer (Sonoporation) in Skeletal Muscle Cells" Ultrasound in Med. & Biol., Vol. 30, No. 11, pp. 1523-1529 (2004), the disclosure of which is incorporated by reference herein. Various other suitable ways in which the below teachings may be carried out will be apparent to those of ordinary skill in the art in view of the teachings herein.

By way of example only, the teachings below may be readily applied to a harmonic surgical instrument as shown and described in U.S. Pub. No. 2006/0079874; now abandoned, a harmonic surgical instrument as shown and described in U.S. Pub. No. 2007/0191713, now abandoned; a harmonic surgical instrument as shown and described in U.S. Pub. No. 2007/0282333, now abandoned; and/or a harmonic surgical instrument as shown and described in U.S. Pub. No. 2008/0200940, now abandoned. As another merely illustrative example, the teachings below may be readily applied to device (100) described above or to harmonic surgical instrument (210) described above. Still other suitable types of harmonic surgical instruments to which the below teachings may be readily applied will be apparent to those of ordinary skill in the art in view of the teachings herein. It should also be understood that, in some versions of the examples provided below, the devices are configured such that the therapeutic agents are only dispensed when the harmonic blade is active. In some instances, this might reduce unnecessary waste of therapeutic agent.

It is also contemplated that the below teachings may be readily applied to various other kinds of medical devices, including but not limited to surgical instruments, medical implants, etc. For instance, the below teachings may be readily applied to virtually any of the kinds of medical devices that are referred to herein. Still other suitable devices to which the below teachings may be readily applied will be apparent to those of ordinary skill in the art in view of the teachings herein. It should therefore be understood that the below examples include harmonic surgical instruments by way of illustration only, and that the below teachings are not intended to be limited to just harmonic surgical instruments. In some instances where gene therapies are administered through a non-harmonic medical device, it may be necessary to provide such gene therapy through a viral carrier. It should also be understood that various components, features, and operabilities of the below examples may be readily combined with each other in various ways, as will be apparent to those of ordinary skill in the art in view of the teachings herein.

1. Exemplary Dispensation of Therapeutic Agent from Blade of Harmonic Device

The following examples include various harmonic surgical instrument end effectors that are operable to dispense a therapeutic agent (e.g., gene therapy fluid, etc.) through a harmonic blade. In each of these examples, it should be understood that the openings through which the therapeutic agent is delivered may be located at positions corresponding to nodes of the ultrasonic energy being transmitted through the harmonic blade. In some instances, dispensing the therapeutic agent at positions corresponding to nodes may reduce the likelihood that the ultrasonic energy has an adverse effect on the therapeutic agent itself. In some other instances, the ultrasonic energy may have no adverse effect on the therapeutic agent itself regardless of where the therapeutic agent is administered along the length of the harmonic blade.

Figure 15:
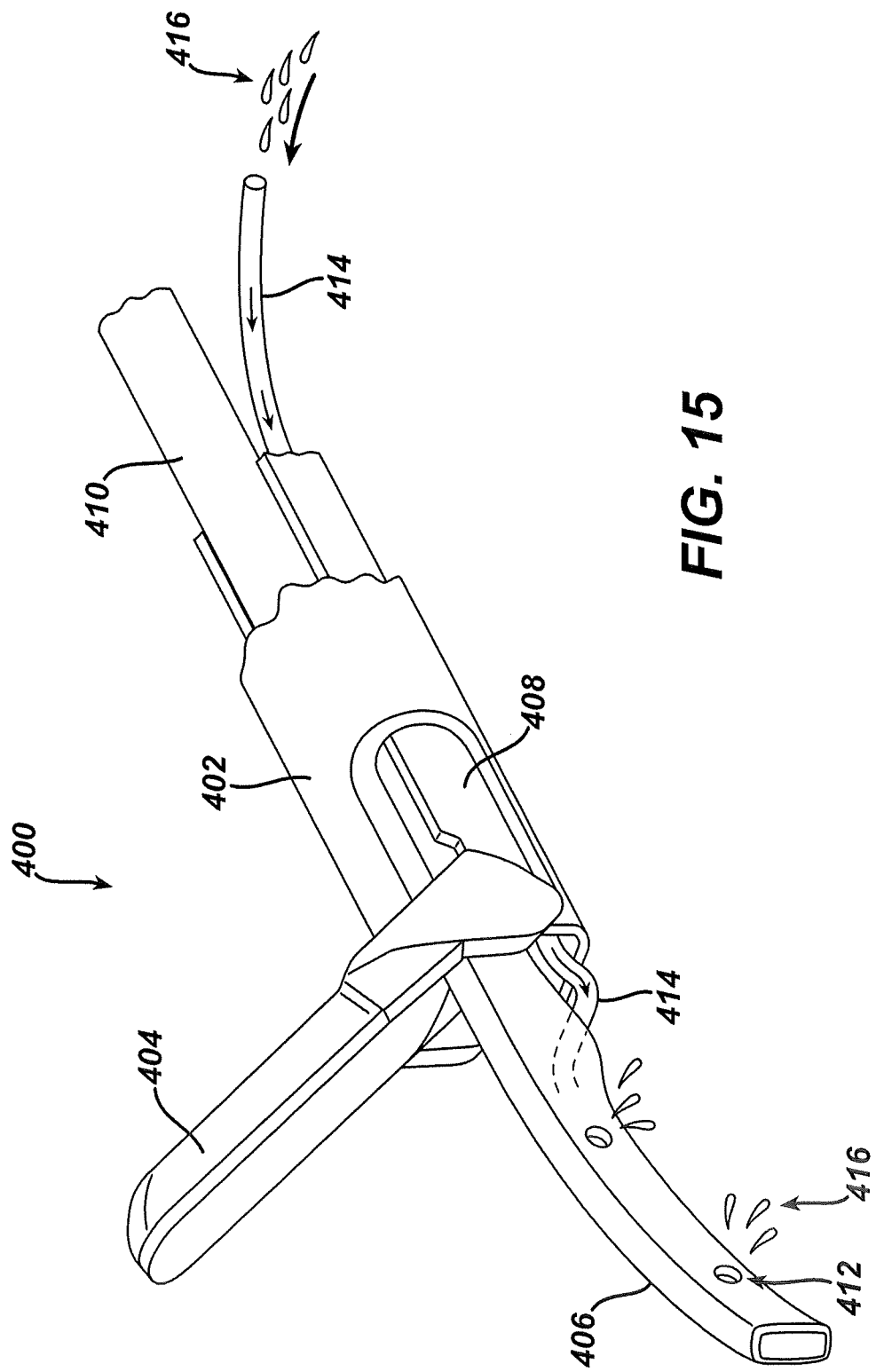
FIG. 15 depicts a partial perspective view of the distal end of an exemplary harmonic surgical instrument with a harmonic blade having a therapeutic agent delivery feature.

FIG. 15 depicts an exemplary end effector (400) that may be provided on a harmonic surgical instrument to deliver a therapeutic agent (e.g., gene therapy fluid, etc.) at a surgical site or other wound site. It should be understood that end effector (400) may be provided on any harmonic surgical instrument referred to herein, among other types of surgical instruments. As shown, end effector (400) is provided at the distal end of a shaft (402), and includes a clamp pad (404) and a harmonic blade (406). Clamp pad (404) is coupled with a pair of actuator arms (408), which are slidably disposed within shaft (402) and selectively translate to pivot clamp pad (404) relative to harmonic blade (406). A waveguide (410) also extends through shaft (402) and is configured to transmit ultrasonic energy from an ultrasonic transducer to harmonic blade (406).

Harmonic blade (406) of the present example also includes a pair of openings (412) formed in its side. While two openings (412) are shown, it should be understood that any other suitable number of openings (412) may be used and that openings (412) may be located at any suitable positions along the length of harmonic blade (406). A conduit (414) is in fluid communication with openings (412). Conduit (414) extends through shaft (402) adjacent to actuator arms (408) and waveguide (410). In an exemplary use, a therapeutic agent (416) is dispensed at a surgical site or other wound site via openings (412). Examples of various suitable structures that may be coupled with conduit (414) to communicate therapeutic agent (416) to openings (412) will be described below in section V.D.3., while other examples will be apparent to those of ordinary skill in the art in view of the teachings herein. As noted above, sonoporation provided by harmonic blade (406) may facilitate transfection in instances where therapeutic agent (416) comprises DNA/genes. Thus, in some examples, therapeutic agent (416) is administered when harmonic blade (406) is actively oscillating. It should also be understood that an oscillating harmonic blade (406) may aerosolize therapeutic agent (416) as therapeutic agent (416) is dispensed through openings (412).

Figure 16:
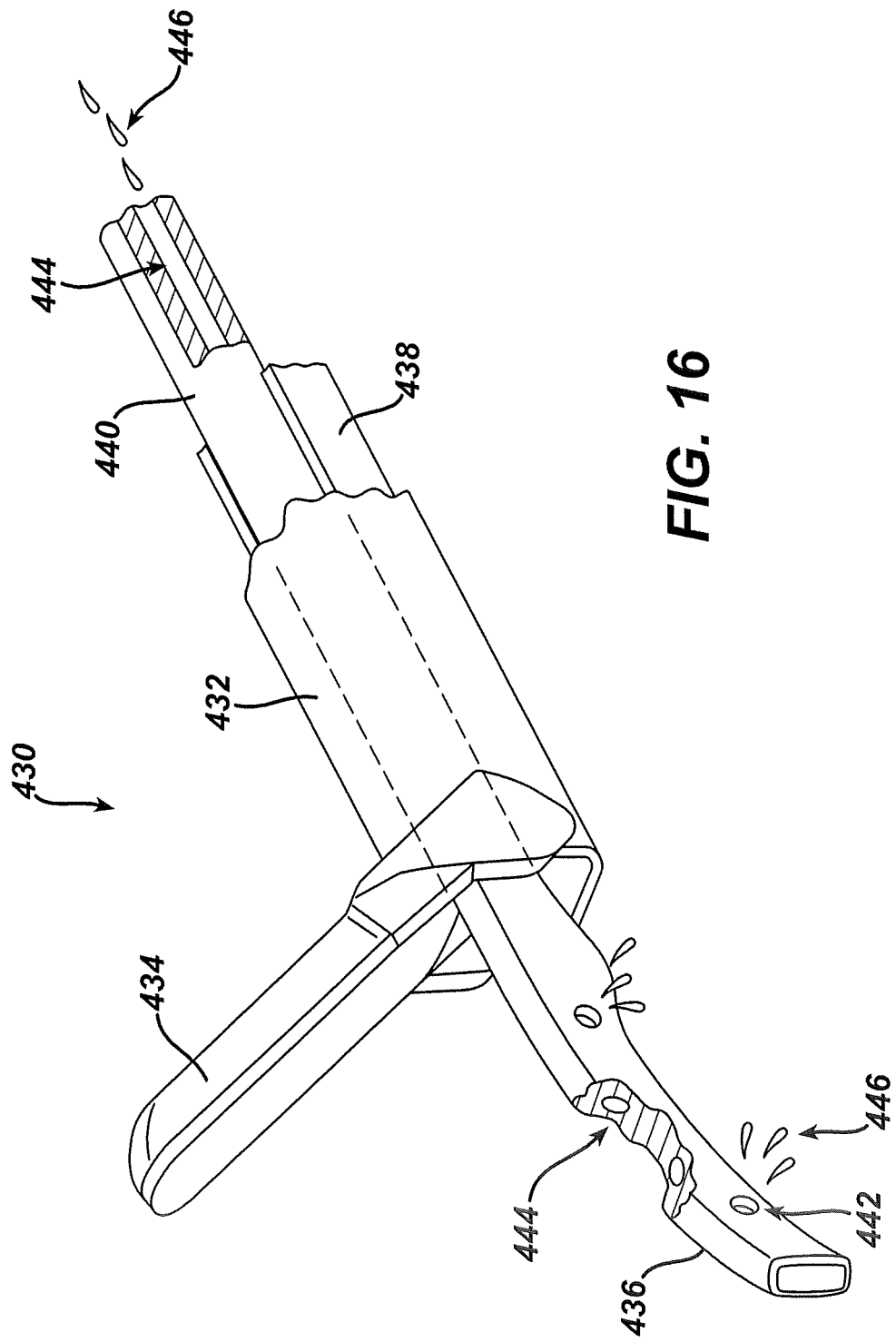
FIG. 16 depicts a partial perspective view of the distal end of another exemplary harmonic surgical instrument with a harmonic blade having a therapeutic agent delivery feature.

FIG. 16 depicts another exemplary end effector (430) that may be provided on a harmonic surgical instrument to deliver a therapeutic agent (e.g., gene therapy fluid, etc.) at a surgical site or other wound site. It should be understood that end effector (430) may be provided on any harmonic surgical instrument referred to herein, among other types of surgical instruments. As shown, end effector (430) is provided at the distal end of a shaft (432), and includes a clamp pad (434) and a harmonic blade (436). Clamp pad (434) is coupled with a pair of actuator arms (438), which are slidably disposed within shaft (432) and selectively translate to pivot clamp pad (434) relative to harmonic blade (436). A waveguide (440) also extends through shaft (432) and is configured to transmit ultrasonic energy from an ultrasonic transducer to harmonic blade (436).

Harmonic blade (436) of the present example also includes a pair of openings (442) formed in its side. While two openings (442) are shown, it should be understood that any other suitable number of openings (442) may be used and that openings (442) may be located at any suitable positions along the length of harmonic blade (436). A lumen (444) is in fluid communication with openings (412). Lumen (444) is formed through waveguide (440) and harmonic blade (436). End effector (430) of this example is thus similar to end effector (400) of FIG. 15, except that end effector (430) has lumen (444) instead of having a separate conduit (414). In an exemplary use, a therapeutic agent (446) is dispensed at a surgical site or other wound site via openings (442). Examples of various suitable structures that may be coupled with lumen (444) to communicate therapeutic agent (446) to openings (442) will be described below in section V.D.3., while other examples will be apparent to those of ordinary skill in the art in view of the teachings herein. As noted above, sonoporation provided by harmonic blade (436) may facilitate transfection in instances where therapeutic agent (446) comprises DNA/genes. Thus, in some examples, therapeutic agent (446) is administered when harmonic blade (436) is actively oscillating. It should also be understood that an oscillating harmonic blade (436) may aerosolize therapeutic agent (446) as therapeutic agent (446) is dispensed through openings (442).

Figure 17:
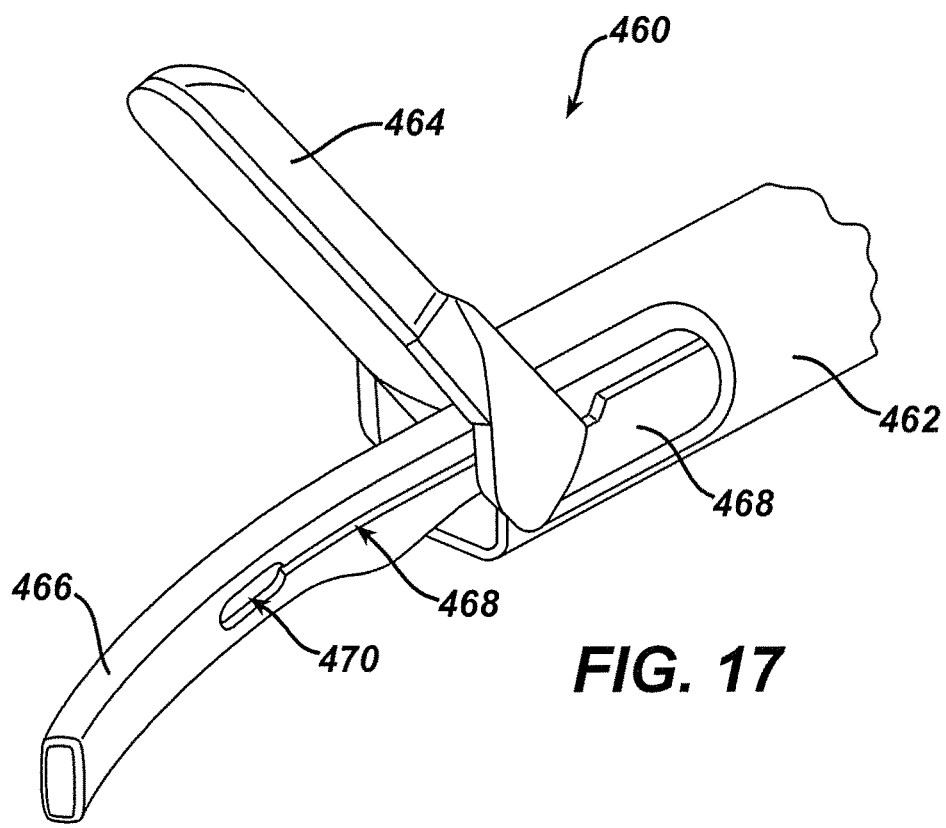
FIG. 17 depicts a partial perspective view of the distal end of another exemplary harmonic surgical instrument with a harmonic blade having a therapeutic agent delivery feature.

FIG. 17 depicts another exemplary end effector (460) that may be provided on a harmonic surgical instrument to deliver a therapeutic agent (e.g., gene therapy fluid, etc.) at a surgical site or other wound site. It should be understood that end effector (460) may be provided on any harmonic surgical instrument referred to herein, among other types of surgical instruments. As shown, end effector (460) is provided at the distal end of a shaft (462), and includes a clamp pad (464) and a harmonic blade (466). Clamp pad (464) is coupled with a pair of actuator arms (468), which are slidably disposed within shaft (462) and selectively translate to pivot clamp pad (464) relative to harmonic blade (466). A waveguide (not shown) also extends through shaft (462) and is configured to transmit ultrasonic energy from an ultrasonic transducer to harmonic blade (466).

Figure 18A:
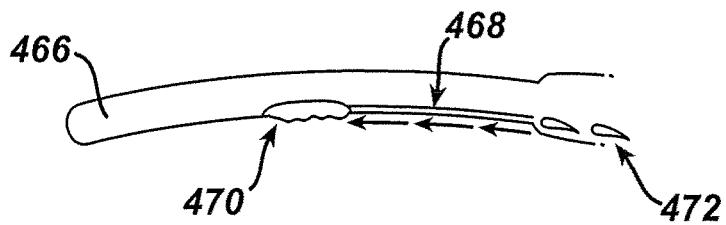
FIG. 18A depicts a top view of the harmonic blade of the harmonic surgical instrument of FIG. 17, in an inactive state.
Figure 18B:
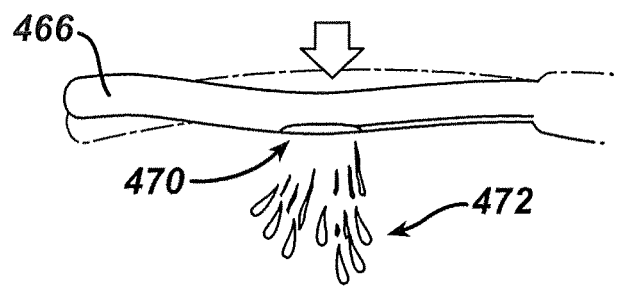
FIG. 18B depicts a top view of the harmonic blade of the harmonic surgical instrument, in an active state.

Harmonic blade (466) of the present example also includes a recessed channel (468) formed in its side and a recessed pool (470) at the distal end of channel (468). While pool (470) is shown at approximately the mid-point along the length of harmonic blade (466), it should be understood that pool (470) may be located at any other suitable position along the length of harmonic blade (466). The proximal end of channel (468) may be in fluid communication with a conduit (e.g., similar to conduit (414) described above), with an internal lumen formed in the waveguide and/or in harmonic blade (466) (e.g., similar to lumen (444) described above), or with any other suitable structure configured to communicate fluid to channel (468). In an exemplary use, a therapeutic agent (472) is dispensed at a surgical site or other wound site via pool (470). In particular, FIG. 18A shows harmonic blade (466) in a non-activated state while FIG. 18B shows harmonic blade (466) in an activated state. When harmonic blade (466) is in a non-activated state as shown in FIG. 18A, therapeutic agent (472) wicks down channel (468) and pools up in pool (470). When harmonic blade (466) is activated as shown in FIG. 18B, the oscillating action of harmonic blade (466) throws therapeutic agent (472) from pool (470). It should be understood that therapeutic agent (472) may continue to wick down channel (468) and be thrown from pool (470) while harmonic blade (466) remains activated. It should also be understood that an activated harmonic blade (466) may also aerosolize therapeutic agent (472). Examples of various suitable structures that may be coupled with channel (468) to communicate therapeutic agent (472) to pool (470) will be described below in section V.D.3., while other examples will be apparent to those of ordinary skill in the art in view of the teachings herein. It should also be understood that, as noted above, sonoporation provided by harmonic blade (466) may facilitate transfection in instances where therapeutic agent (472) comprises DNA/genes.

FIGS. 19A-C and 20 show an exemplary harmonic blade (500) that may be incorporated into an end effector of a harmonic surgical instrument to deliver a therapeutic agent (e.g., gene therapy fluid, etc.) at a surgical site or other wound site. It should be understood that harmonic blade (500) may be provided on any harmonic surgical instrument referred to herein, among other types of surgical instruments. Harmonic blade (500) of the present example includes a recessed channel (510) formed in its side. While channel (510) is shown as being formed in only one side of harmonic blade (500), it should be understood that more than one side of harmonic blade (500) may include a channel (510). Channel (510) of this example includes a plurality of pocket regions (512) that are defined in part by fingers (514), which create narrow regions (516) in channel (510). Each finger (514) includes a distally-inclined distal face (518) and a distally inclined proximal face (520). The distally-inclined orientations of faces (518, 520) are configured to facilitate distal communication of therapeutic agent (522) along channel (510). This action may be seen by viewing FIGS. 19A-19C as a series where harmonic blade (500) is activated.

Figure 19A:
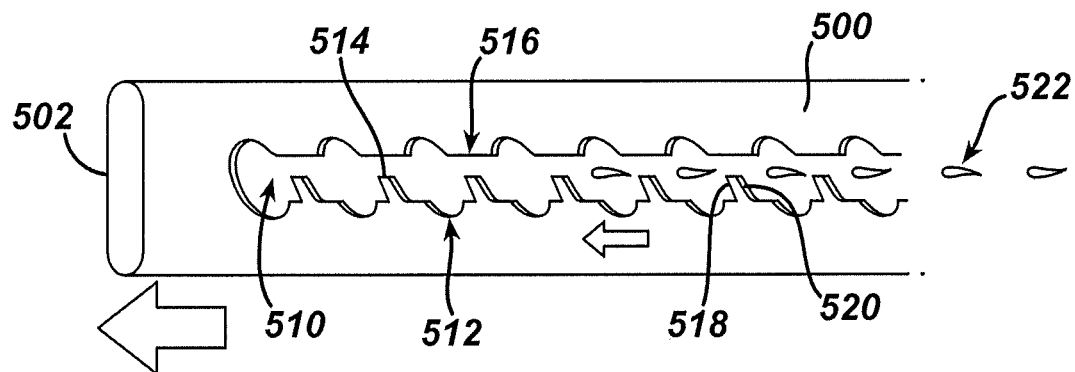
FIG. 19A depicts a side view of another exemplary harmonic blade having a therapeutic agent delivery feature, in a distal position at a first instant while activated.
Figure 19B:
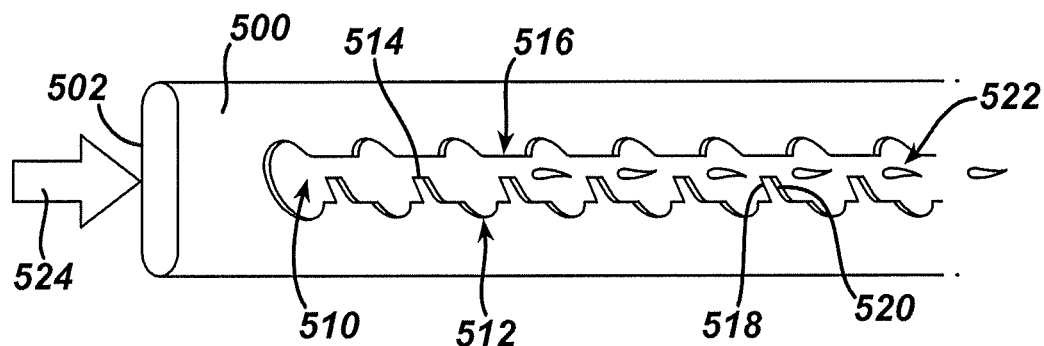
FIG. 19B depicts a side view of the harmonic blade of FIG. 19A, in a proximal position at a second instant while activated.
Figure 19C:
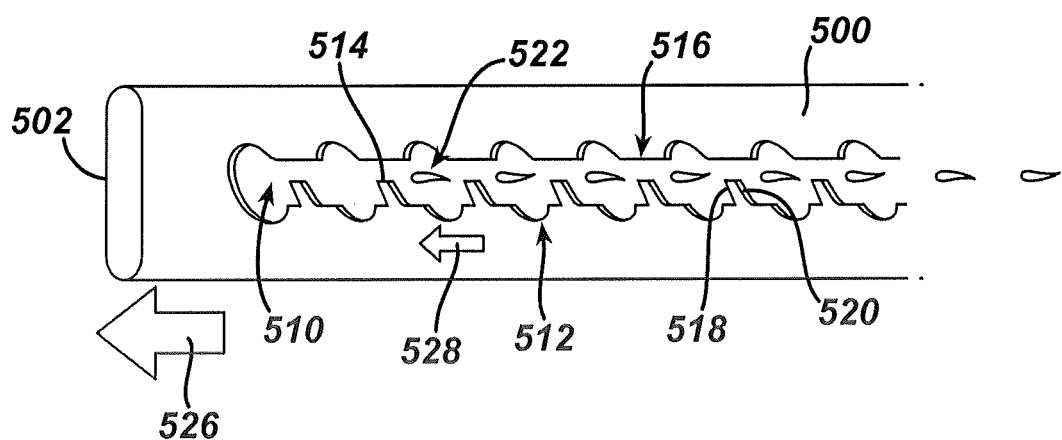
FIG. 19C depicts a side view of the harmonic blade of FIG. 19A, in the proximal position at a third instant while activated.
Figure 20:
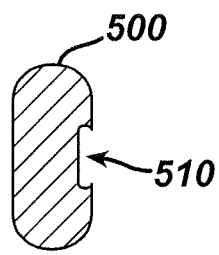
FIG. 20 depicts a cross-sectional end view of the harmonic blade of FIG. 19A.

FIG. 19A shows harmonic blade (500) at a distal position at a first time instant during activation. At this stage, therapeutic agent (522) has reached the fifth pocket region (512) from the distal end (502) of harmonic blade (500). In FIG. 19B, harmonic blade (500) has moved proximally during oscillation at a second time instant, as indicated by arrow (524). The inertia of therapeutic agent (522) has kept the position of therapeutic agent (522) constant relative to the external environment, yet the proximal movement of harmonic blade (500) has effectively "advanced" therapeutic agent (522) to the fourth pocket region (512) from distal end (502) of harmonic blade (500). The distally-inclined orientation of proximal face (520) also substantially prevents finger (514) from pushing therapeutic agent (522) proximally as harmonic blade (500) moves proximally, allowing therapeutic agent (522) to essentially "ride over" finger (514) as harmonic blade (500) moves proximally. In FIG. 19C, harmonic blade (500) has moved distally during oscillation at a third time instant, as indicated by arrow (526). The distally-inclined orientation of distal face (518) has allowed finger (514) to throw therapeutic agent (522) distally to the third pocket region (512) from distal end (502) of harmonic blade (500), as indicated by arrow (528). As harmonic blade (500) continues to oscillate, this distal progression of therapeutic agent (522) continues. Any therapeutic agent (522) that makes it to the distal-most pocket region (512) will be thrown out laterally from harmonic blade (500). Of course, at least some therapeutic agent (522) may be thrown laterally from harmonic blade (500) before it ever reaches the distal-most pocket region (512). It should also be understood that pressure from the source of therapeutic agent (522) may facilitate distal communication of therapeutic agent (522) along channel (510). Furthermore, it should be understood that an oscillating harmonic blade (500) may aerosolize therapeutic agent (522) as therapeutic agent (522) is thrown from harmonic blade (500).

Examples of various suitable structures that may be coupled with channel (510) to communicate therapeutic agent (522) to harmonic blade (500) will be described below in section V.D.3., while other examples will be apparent to those of ordinary skill in the art in view of the teachings herein. It should also be understood that, as noted above, sonoporation provided by harmonic blade (500) may facilitate transfection in instances where therapeutic agent (522) comprises DNA/genes.

Figure 21:
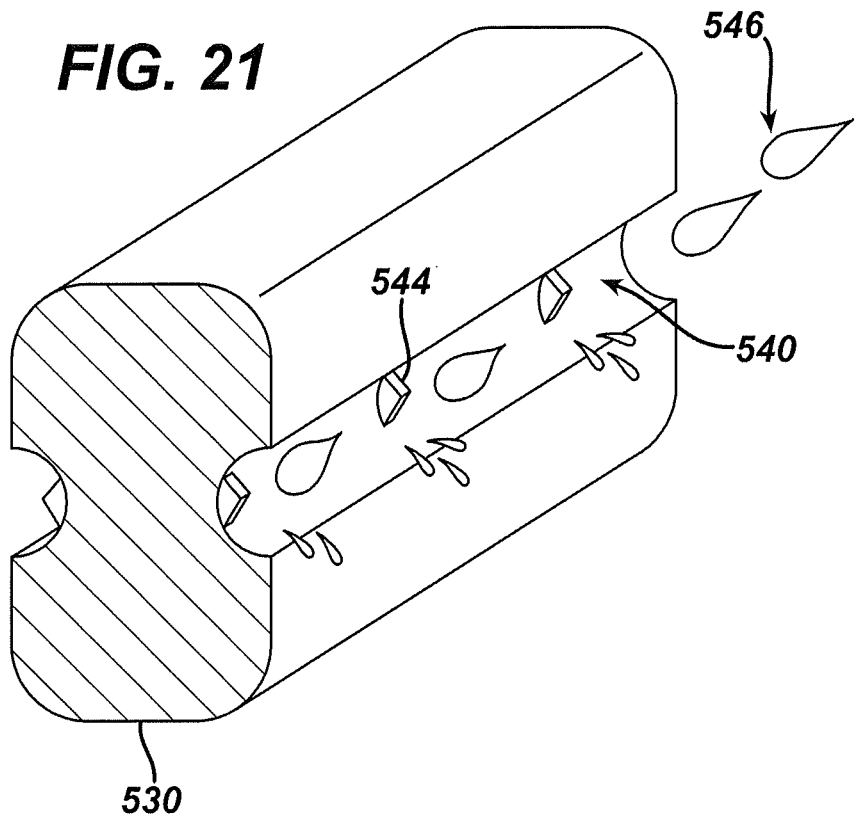
FIG. 21 depicts a perspective cross-sectional view of another exemplary harmonic blade having a pair of therapeutic agent delivery features.

FIG. 21 shows another exemplary harmonic blade (530) that may be incorporated into an end effector of a harmonic surgical instrument to deliver a therapeutic agent (e.g., gene therapy fluid, etc.) at a surgical site or other wound site. It should be understood that harmonic blade (530) may be provided on any harmonic surgical instrument referred to herein, among other types of surgical instruments. Harmonic blade (530) of the present example includes a pair of recessed channels (540) formed in its sides. Recessed channels (540) each include several spaced apart and outwardly extending spikes (544) along the length of each channel (540). In some versions, spikes (544) are configured to assist in conveying therapeutic agent (546) distally along the length of harmonic blade (530) as harmonic blade (530) oscillates. In addition or in the alternative, spikes (544) may be configured to assist in throwing therapeutic agent (546) from harmonic blade (530) as harmonic blade (530) oscillates. Various suitable configurations and spacings that may be used for channels (540) and spikes (544) will be apparent to those of ordinary skill in the art in view of the teachings herein. By way of example only, spikes (544) may alternatively be formed as rounded protrusions instead of having sharp points as shown. Furthermore, it should be understood that an oscillating harmonic blade (530) may aerosolize therapeutic agent (546) as therapeutic agent (546) is thrown from harmonic blade (530). Examples of various suitable structures that may be coupled with channels (540) to communicate therapeutic agent (546) to harmonic blade (530) will be described below in section V.D.3., while other examples will be apparent to those of ordinary skill in the art in view of the teachings herein.

Figure 22:
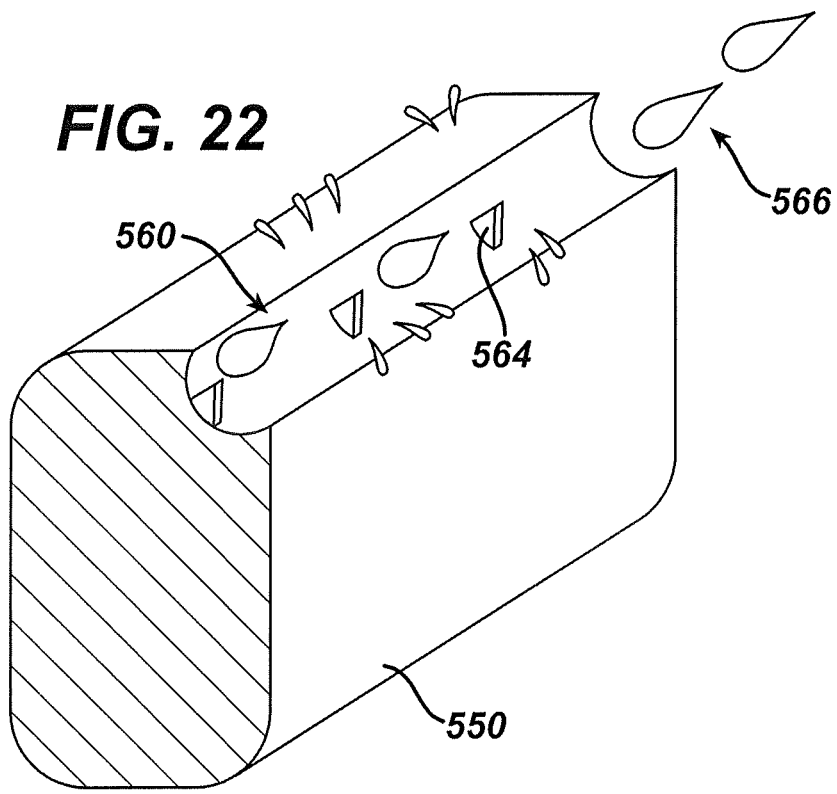
FIG. 22 depicts a perspective cross-sectional view of another exemplary harmonic blade having a therapeutic agent delivery feature.

FIG. 22 shows another exemplary harmonic blade (550) that may be incorporated into an end effector of a harmonic surgical instrument to deliver a therapeutic agent (e.g., gene therapy fluid, etc.) at a surgical site or other wound site. It should be understood that harmonic blade (550) may be provided on any harmonic surgical instrument referred to herein, among other types of surgical instruments. Harmonic blade (550) of the present example includes a recessed channel (560) formed along one of its longitudinally extending edge corners. While harmonic blade (550) is shown with channel (560) extending along only one edge corner, it should be understood that one or more additional longitudinally extending edge corners of harmonic blade (550) may include a channel (560). Recessed channel (560) includes several spaced apart and outwardly extending spikes (564) along the length of channel (560). In some versions, spikes (564) are configured to assist in conveying therapeutic agent (566) distally along the length of harmonic blade (550) as harmonic blade (550) oscillates. In addition or in the alternative, spikes (564) may be configured to assist in throwing therapeutic agent (566) from harmonic blade (550) as harmonic blade (550) oscillates. Various suitable configurations and spacings that may be used for channel (550) and spikes (564) will be apparent to those of ordinary skill in the art in view of the teachings herein. By way of example only, spikes (564) may alternatively be formed as rounded protrusions instead of having sharp points as shown. Furthermore, it should be understood that an oscillating harmonic blade (550) may aerosolize therapeutic agent (566) as therapeutic agent (566) is thrown from harmonic blade (550). Examples of various suitable structures that may be coupled with channel (560) to communicate therapeutic agent (566) to harmonic blade (550) will be described below in section V.D.3., while other examples will be apparent to those of ordinary skill in the art in view of the teachings herein.

Figure 23A:
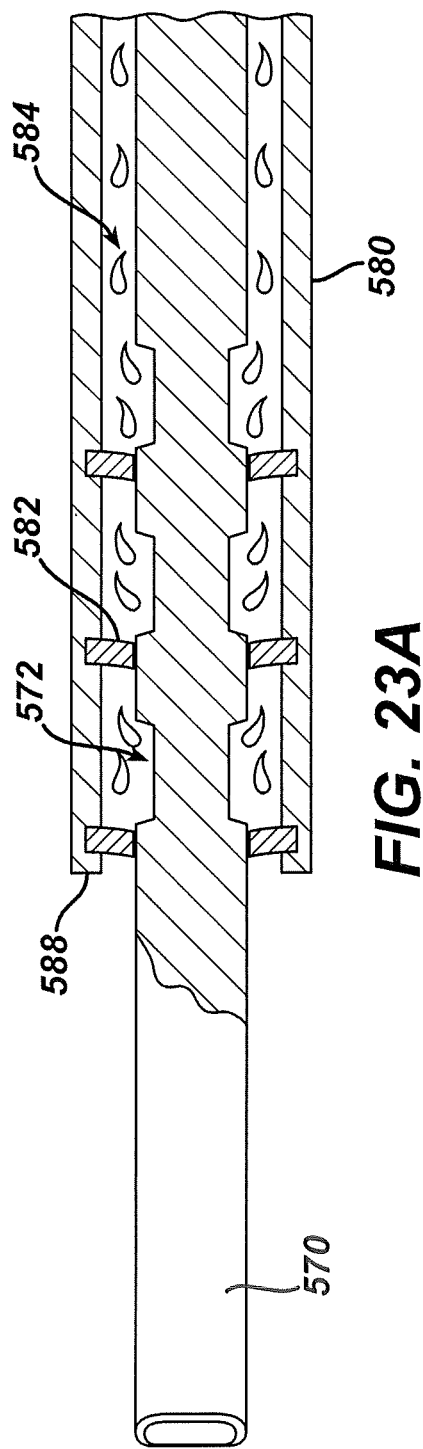
FIG. 23A depicts a top cross-sectional view of another exemplary harmonic blade having a sheath and therapeutic agent delivery features, with the blade in a proximal position while activated.
Figure 23B:
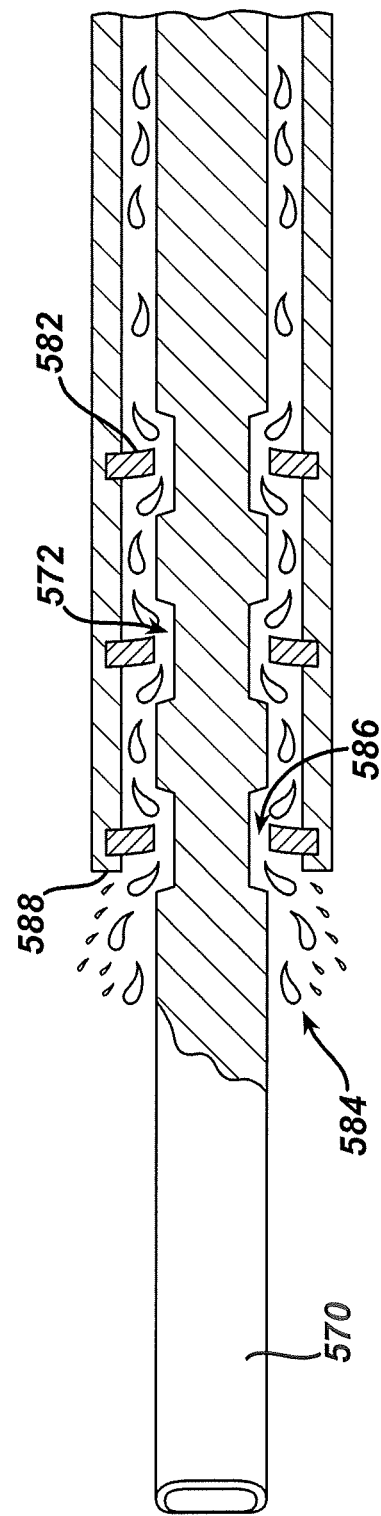
FIG. 23B depicts a top cross-sectional view of the harmonic blade of FIG. 23A, with the blade in a distal position while activated.

FIGS. 23A-B show another exemplary harmonic blade (570) that may be incorporated into an end effector of a harmonic surgical instrument to deliver a therapeutic agent (e.g., gene therapy fluid, etc.) at a surgical site or other wound site. It should be understood that harmonic blade (570) may be provided on any harmonic surgical instrument referred to herein, among other types of surgical instruments. A sheath (580) is disposed about a proximal portion of harmonic blade (570) in the present example. The inner diameter of sheath (580) is sufficiently greater than the outer diameter of harmonic blade (570) to allow therapeutic agent (584) to be communicated therebetween. Harmonic blade (570) includes a plurality of annular recesses (572) along the portion of harmonic blade (570) that is disposed in sheath (580). A plurality of seals (582) are located within sheath (582) and correspond with the longitudinal positions of annular recesses (572). Seals (582) define an inner diameter that is greater than the outer diameter of annular recesses (572) yet that is less than the outer diameter of the rest of harmonic blade (570). Thus, when harmonic blade (570) is at a proximal position during oscillation or before oscillation as shown in FIG. 23A, therapeutic agent (584) is trapped between seals (582) and behind seals (582).

When harmonic blade (570) is at a distal position during oscillation as shown in FIG. 23B, the gap (586) provided between seals (582) and annular recesses (572) permit distal passage of therapeutic agent (584) out through the open distal end (588) of sheath (580). In some versions, therapeutic agent (584) exits through open distal end (588) in a pulsed fashion (e.g., only exiting when harmonic blade (570) is at the distal position during oscillation, etc.). Distal communication of therapeutic agent (584) through sheath (580) may be provided by oscillation of harmonic blade (570) and/or by pressure from the source of therapeutic agent (584). Examples of various suitable structures that may be coupled with sheath (580) to communicate therapeutic agent (584) through sheath (580) will be described below in section V.D.3., while other examples will be apparent to those of ordinary skill in the art in view of the teachings herein. It should also be understood that therapeutic agent (584) may be leaked out, be pushed out, and/or be aerosolized as it exits open distal end (588) of sheath (580).

FIGS. 24A-B show another exemplary harmonic blade (600) that may be incorporated into an end effector of a harmonic surgical instrument to deliver a therapeutic agent (e.g., gene therapy fluid, etc.) at a surgical site or other wound site. It should be understood that harmonic blade (600) may be provided on any harmonic surgical instrument referred to herein, among other types of surgical instruments. A sheath (620) is disposed about a proximal portion of harmonic blade (600) in the present example. The inner diameter of sheath (620) is sufficiently greater than the outer diameter of harmonic blade (600) to allow therapeutic agent (644) to be communicated therebetween. Harmonic blade (600) includes an outwardly extending annular protrusion (602) that corresponds with an inwardly extending annular flange (622) of sheath (620). In particular, when harmonic blade (600) is at a distal position during oscillation or before oscillation as shown in FIG. 24A, therapeutic agent (644) is trapped behind annular flange (622).

When harmonic blade (600) is at a proximal position during oscillation as shown in FIG. 24B, a gap (624) is opened up between harmonic blade (600) and annular flange (622), permitting exit of therapeutic agent (644) therebetween. In some versions, therapeutic agent (644) exits through gap (624) in a pulsed fashion (e.g., only exiting when harmonic blade (600) is at the distal position during oscillation, etc.). Distal communication of therapeutic agent (644) through sheath (620) may be provided by oscillation of harmonic blade (600) and/or by pressure from the source of therapeutic agent (644). Examples of various suitable structures that may be coupled with sheath (620) to communicate therapeutic agent (644) through sheath (620) will be described below in section V.D.3., while other examples will be apparent to those of ordinary skill in the art in view of the teachings herein. It should also be understood that therapeutic agent (644) may be leaked out, be pushed out, and/or be aerosolized as it exits gap (624).

Figure 25:
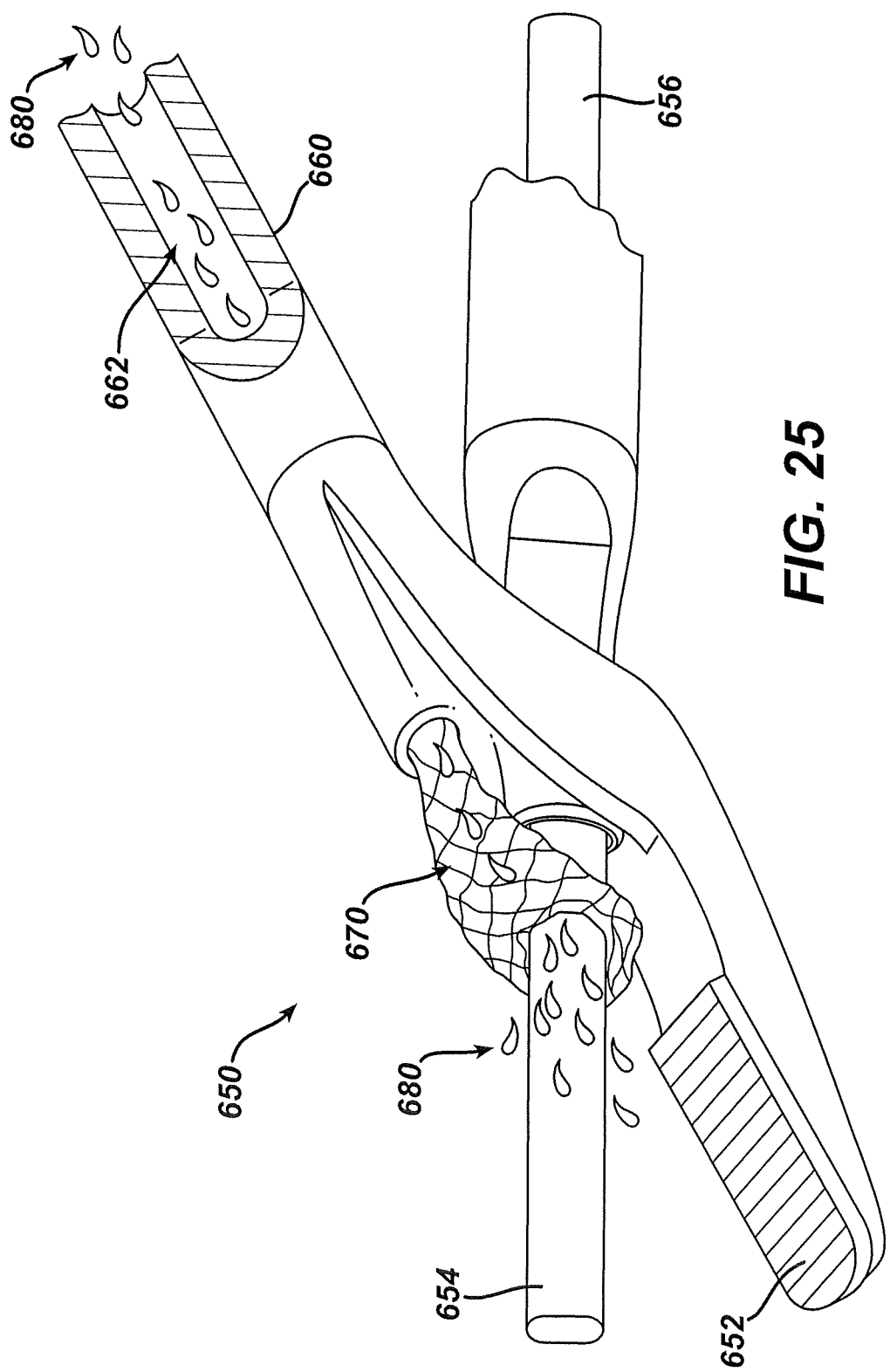
FIG. 25 depicts a partial perspective view of the distal end of another exemplary harmonic surgical instrument having a therapeutic agent delivery feature adjacent to its harmonic blade.

FIG. 25 depicts another exemplary end effector (650) that may be provided on a harmonic surgical instrument to deliver a therapeutic agent (e.g., gene therapy fluid, etc.) at a surgical site or other wound site. It should be understood that end effector (650) may be provided on any harmonic surgical instrument referred to herein, among other types of surgical instruments. As shown, end effector (650) includes a clamp pad (652) and a harmonic blade (654). A waveguide (656) extends proximally from harmonic blade (654) and is configured to transmit ultrasonic energy from an ultrasonic transducer to harmonic blade (654). An arm (660) extends proximally from clamp pad (652) and is operable to pivot clamp pad (652) relative to harmonic blade (654). A wicking mesh (670) is also coupled with arm (660) and is wrapped about a proximal portion of harmonic blade (654). Wicking mesh (670) is flexible such that pivotal movement of arm (660) and clamp pad (652) relative to harmonic blade (654) will not adversely compromise the integrity of wicking mesh (670). Wicking mesh (670) is configured to leak therapeutic agent (680) onto harmonic blade (654) as will be described in greater detail below, allowing therapeutic agent (680) to reach a surgical site or other wound site.

An internal lumen (662) is defined in arm (660) and is in fluid communication with wicking mesh (670), such that wicking mesh (670) is configured to wick therapeutic agent (680) from internal lumen (662). Internal lumen (662) is also in fluid communication with a source of therapeutic agent (680). In some versions, the source comprises a therapeutic agent cartridge that is inserted in arm (660). Additional examples of various suitable structures that may be coupled with lumen (662) to communicate therapeutic agent (680) to wicking mesh (670) will be described below in section V.D.3., while other examples will be apparent to those of ordinary skill in the art in view of the teachings herein. As noted above, sonoporation provided by harmonic blade (654) may facilitate transfection in instances where therapeutic agent (680) comprises DNA/genes. Thus, in some examples, therapeutic agent (680) is administered when harmonic blade (654) is actively oscillating. It should also be understood that an oscillating harmonic blade (654) may aerosolize therapeutic agent (680) as therapeutic agent (680) is leaked from wicking mesh (670) onto harmonic blade (654). Still other suitable ways in which a therapeutic agent may be administered from a harmonic blade will be apparent to those of ordinary skill in the art in view of the teachings herein.

Figure 26:
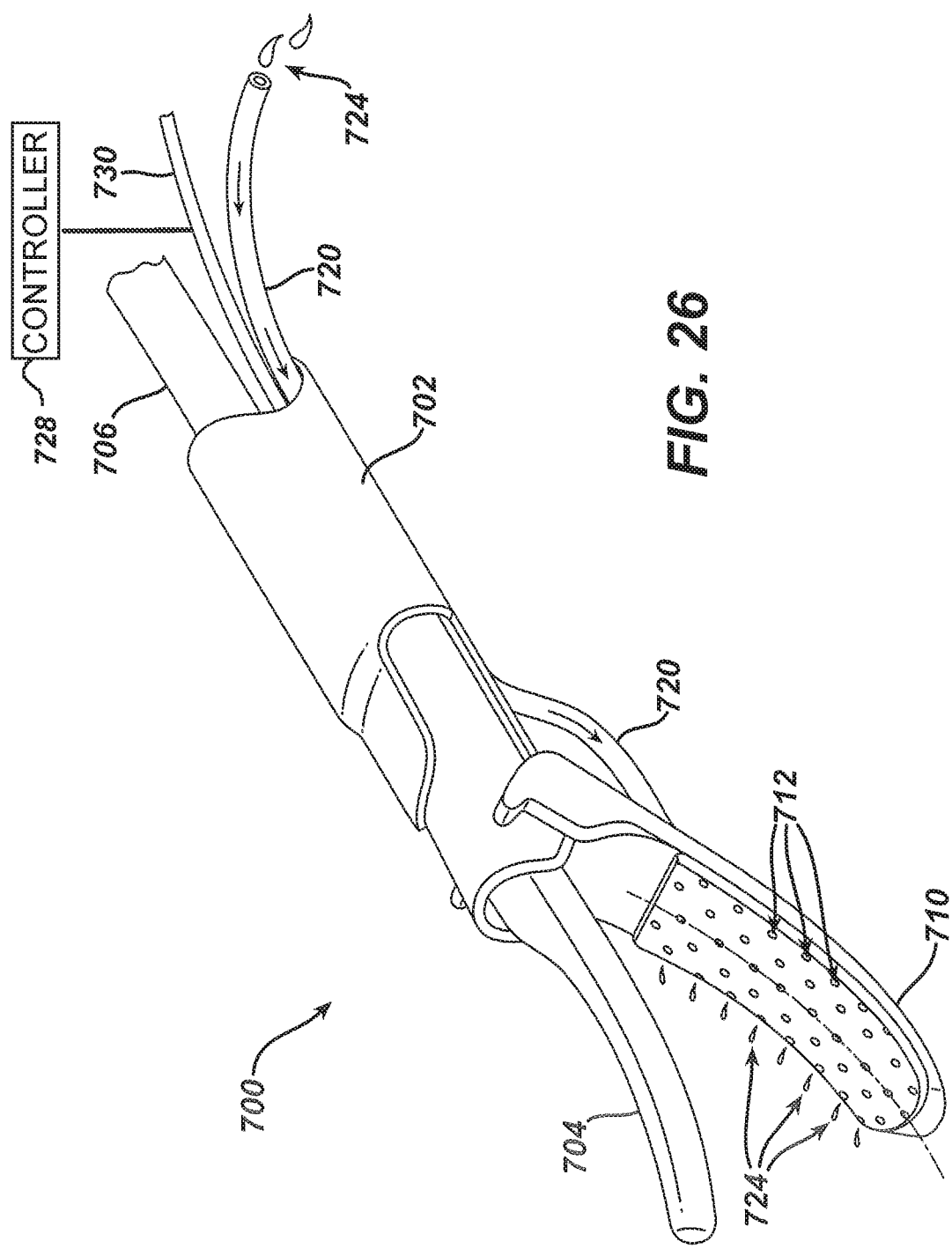
FIG. 26 depicts a partial perspective view of the distal end of another exemplary harmonic surgical instrument with a clamp pad having therapeutic agent delivery features.

2. Exemplary Dispensation of Therapeutic Agent from Clamp Pad of Harmonic Device FIG. 26 depicts an exemplary end effector (700) that may be provided on a harmonic surgical instrument to deliver a therapeutic agent (e.g., gene therapy fluid, etc.) at a surgical site or other wound site. It should be understood that end effector (700) may be provided on any harmonic surgical instrument referred to herein, among other types of surgical instruments. As shown, end effector (700) is provided at the distal end of a shaft (702), and includes a clamp pad (710) and a harmonic blade (704). Clamp pad (710) is operable to pivot relative to harmonic blade (704). A waveguide (706)

extends through shaft (702) and is configured to transmit ultrasonic energy from an ultrasonic transducer to harmonic blade (704).

Figure 27A:
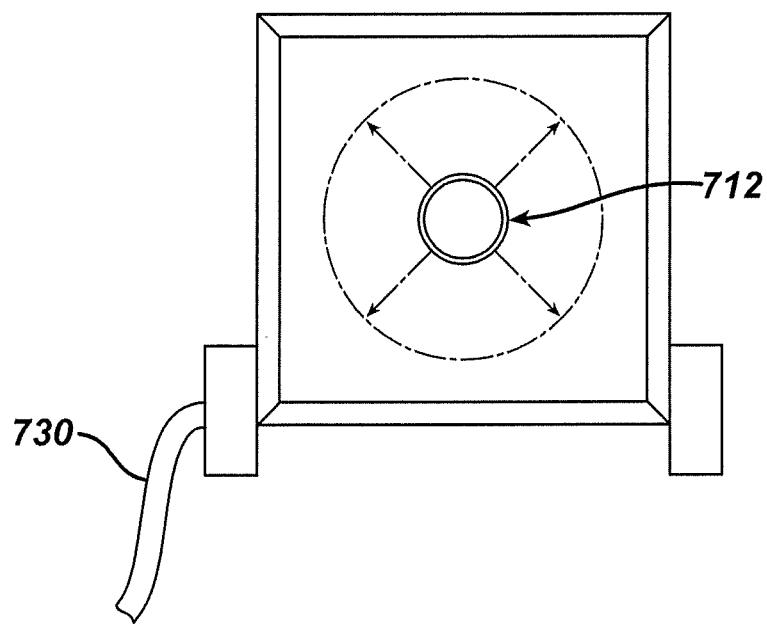
FIG. 27A depicts a top view of a therapeutic agent delivery feature of the clamp pad of FIG. 26, in a non-activated state.
Figure 27B:
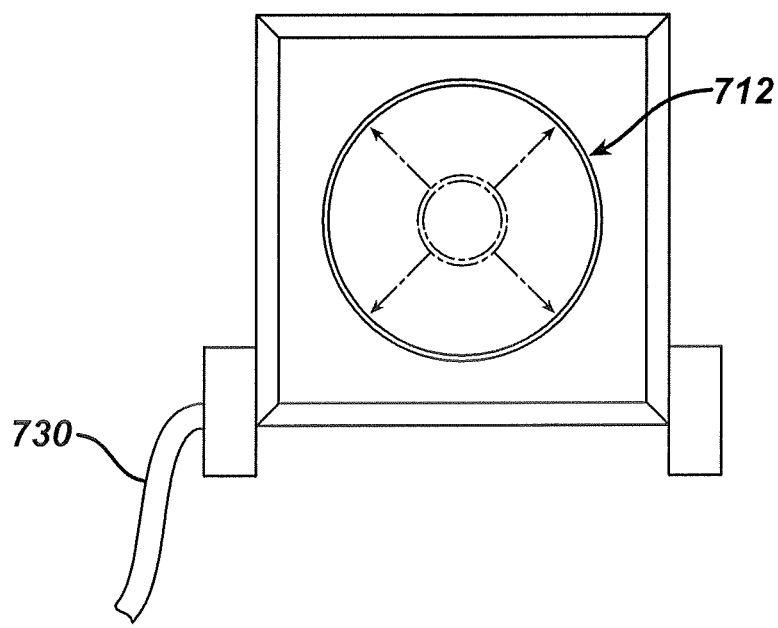
FIG. 27B depicts a top view of the therapeutic agent delivery feature of FIG. 27A, in an activated state.

Clamp pad (710) of the present example includes a plurality of orifices (712). Orifices (712) are in fluid communication with a conduit (720), which extends through shaft (702) and is configured to communicate therapeutic agent (724) to orifices (712). Examples of various suitable structures that may be coupled with conduit (720) to communicate therapeutic agent (724) to orifices (712) will be described below in section V.D.3., while other examples will be apparent to those of ordinary skill in the art in view of the teachings herein. In the present example, orifices (712) are subject to selective activation. In particular, as shown in FIG. 27A, a given orifice (712) is at least substantially closed (712) when orifice (712) is in an inactive state. In some versions, orifice (712) is completely closed when inactive. In some other versions, orifice (712) is not closed all the way when inactive but is closed enough to prevent communication of therapeutic agent (724) through orifice (712). As shown in FIG. 27B, orifice (712) is opened when activated by a signal from a controller (728) applied via wire (730). When so opened, orifice (712) permits communication of therapeutic agent (724) therethrough. Orifices (712) of this example are thus operable in a manner similar to those found in inkjet printer cartridges (e.g., thermal inkjets or piezoelectric inkjets). As shown in FIG. 26, wire (730) also extends through shaft (702) to a switch or control module of the harmonic surgical instrument.

In some versions, a single wire (730) is used to selectively activate all orifices (712) in clamp pad (710) substantially simultaneously. In some other versions, orifices (712) may be selectively activated individually or in groups. Such capabilities may allow the user (or automated control system) to selectively adjust the dosage of therapeutic agent (724). For instance, in situations calling for a high dosage of therapeutic agent (724), a relatively large group of orifices (712) or all orifices (712) may be activated to open; while in situations calling for a relatively low dosage of therapeutic agent (724), a relatively small group of orifices (712) even just a single orifice (712) may be activated to open. In versions where orifices (712) are addressable in groups or independently from each other, a plurality of wires (730) may be used, each being dedicated to a particular respective orifice (712) or respective orifice group (712). Alternatively, using hardware and/or communication techniques/protocols that will be apparent to those of ordinary skill in the art in view of the teachings herein, a single wire (730) may still be used to communicate signals in versions where orifices (712) are addressable in groups or independently from each other. In still other versions of end effector (700), orifices (712) are simple openings that are not subject to activation, such that the size of orifices (712) remains substantially constant, such that therapeutic agent (724) may simply leak out or be forced out through orifices (712), and such that wire (730) may be eliminated.

As noted above, sonoporation provided by harmonic blade (704) may facilitate transfection in instances where therapeutic agent (724) comprises DNA/genes. Thus, in some examples, therapeutic agent (724) is administered when harmonic blade (704) is actively oscillating. To that end, orifices (712) may be selectively activated to only open (as shown in FIG. 27B) when harmonic blade (704) is activated; and to substantially close up (as shown in FIG. 27A) when harmonic blade (704) is inactive. For instance, orifices (712) may be tied to the same control feature(s) (e.g., buttons) that is/are used to selectively activate harmonic blade (704). Alternatively, orifices (712) may be operable for activation independent from activation of harmonic blade (704). It should be understood that sonoporation provided by harmonic blade (704) may still facilitate transfection in instances where therapeutic agent (724) is introduced to the surgical site or other kind of wound site before harmonic blade (704) is activated, such that the introduction of therapeutic agent (724) and the activation of harmonic blade (704) do not necessarily have to be synchronized in every instance.

Figure 28:
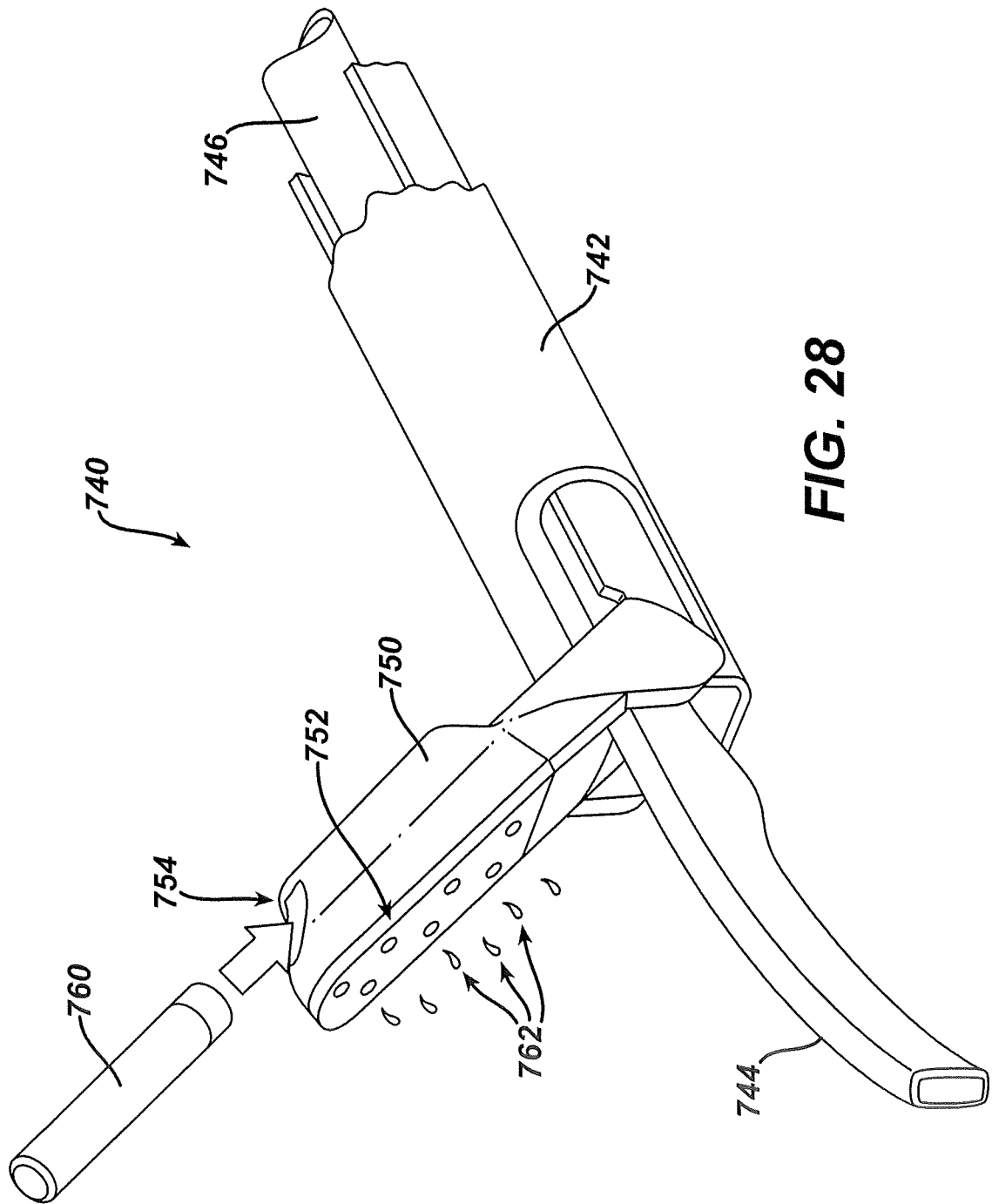
FIG. 28 depicts a partial perspective view of the distal end of another exemplary harmonic surgical instrument with a clamp pad having therapeutic agent delivery features and a therapeutic agent cartridge.

FIG. 28 depicts another exemplary end effector (740) that may be provided on a harmonic surgical instrument to deliver a therapeutic agent (e.g., gene therapy fluid, etc.) at a surgical site or other wound site. It should be understood that end effector (740) may be provided on any harmonic surgical instrument referred to herein, among other types of surgical instruments. As shown, end effector (740) is provided at the distal end of a shaft (742), and includes a clamp pad (750) and a harmonic blade (744). Clamp pad (750) is operable to pivot relative to harmonic blade (744). A waveguide (746) extends through shaft (742) and is configured to transmit ultrasonic energy from an ultrasonic transducer to harmonic blade (744).

Clamp pad (750) of the present example includes a plurality of orifices (752). Clamp pad (750) also includes a chamber (754) to receive a therapeutic agent cartridge (760). Chamber (754) is configured such that, once therapeutic agent cartridge (760) is inserted in chamber (754), therapeutic agent (762) may be communicated through orifices (752). For instance, a sharp hollow nib (not shown) in chamber (754) may pierce a septum of cartridge (760) as soon as cartridge (760) is fully inserted in chamber (754), and this hollow nib may be in fluid communication with orifices (752), such that the nib (and any other suitable fluid communication components) provides a fluid circuit from the interior of cartridge (760) to orifices (752). In some versions, orifices (752) are subject to selective activation like orifices (712) described above. In some other versions, orifices (752) are simple openings that are not subject to activation, such that the size of orifices (752) remains substantially constant, such that therapeutic agent (762) may simply leak out or be forced out through orifices (752). It should therefore be understood that end effector (740) of this example may be configured and operable in a manner substantially similar to those described above with respect to end effector (700), with the exception that orifices (752) in end effector (740) receive therapeutic agent (762) from cartridge (760) instead of conduit (720).

Figure 29:
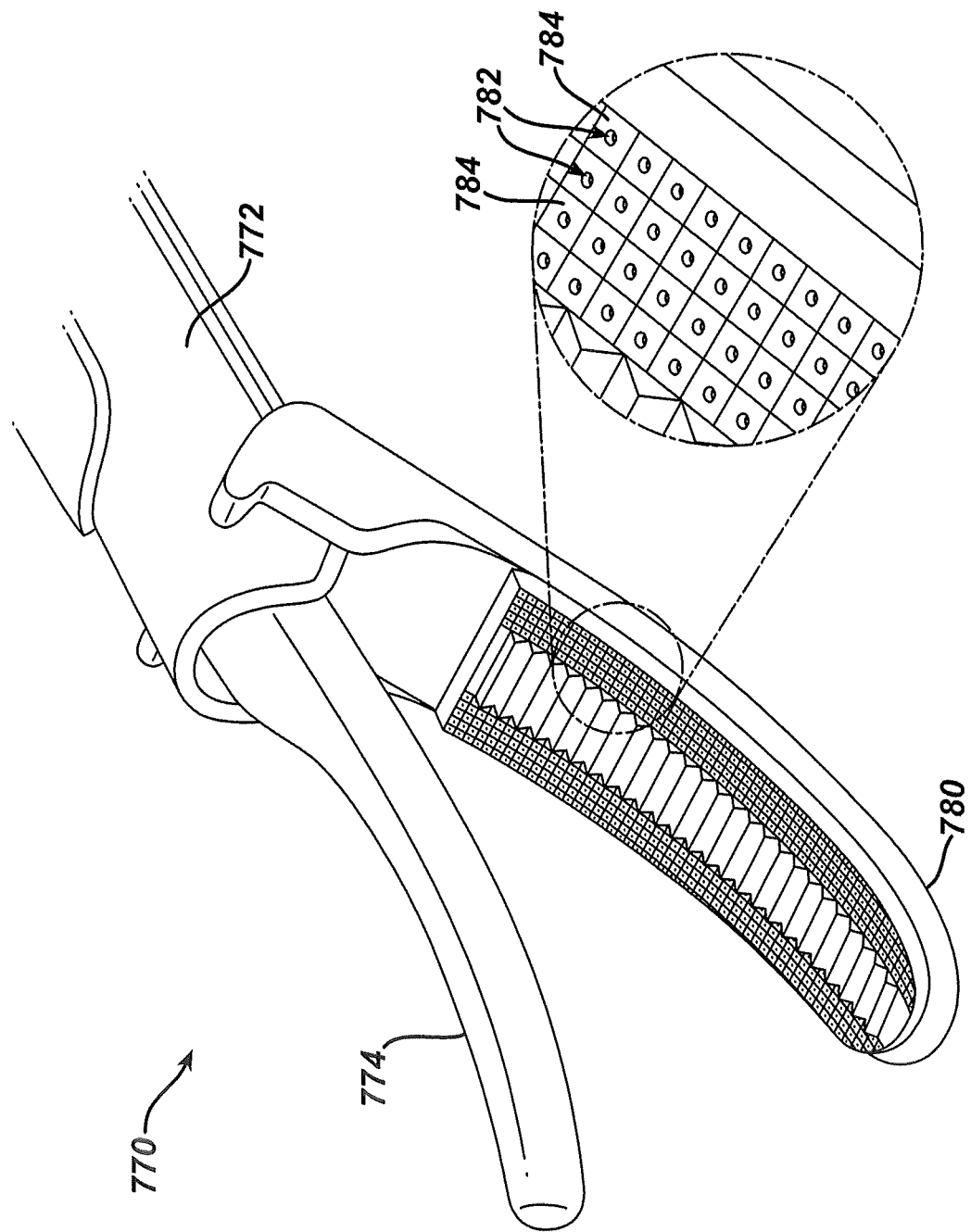
FIG. 29 depicts a partial perspective view of the distal end of another exemplary harmonic surgical instrument with a clamp pad having therapeutic agent delivery features.

FIG. 29 depicts yet another exemplary end effector (770) that may be provided on a harmonic surgical instrument to deliver a therapeutic agent (e.g., gene therapy fluid, etc.) at a surgical site or other wound site. It should be understood that end effector (770) may be provided on any harmonic surgical instrument referred to herein, among other types of surgical instruments. As shown, end effector (770) is provided at the distal end of a shaft (772), and includes a clamp pad (780) and a harmonic blade (774). Clamp pad (780) is operable to pivot relative to harmonic blade (774). A waveguide (not shown) extends through shaft (772) and is configured to transmit ultrasonic energy from an ultrasonic transducer to harmonic blade (774).

Figure 30:
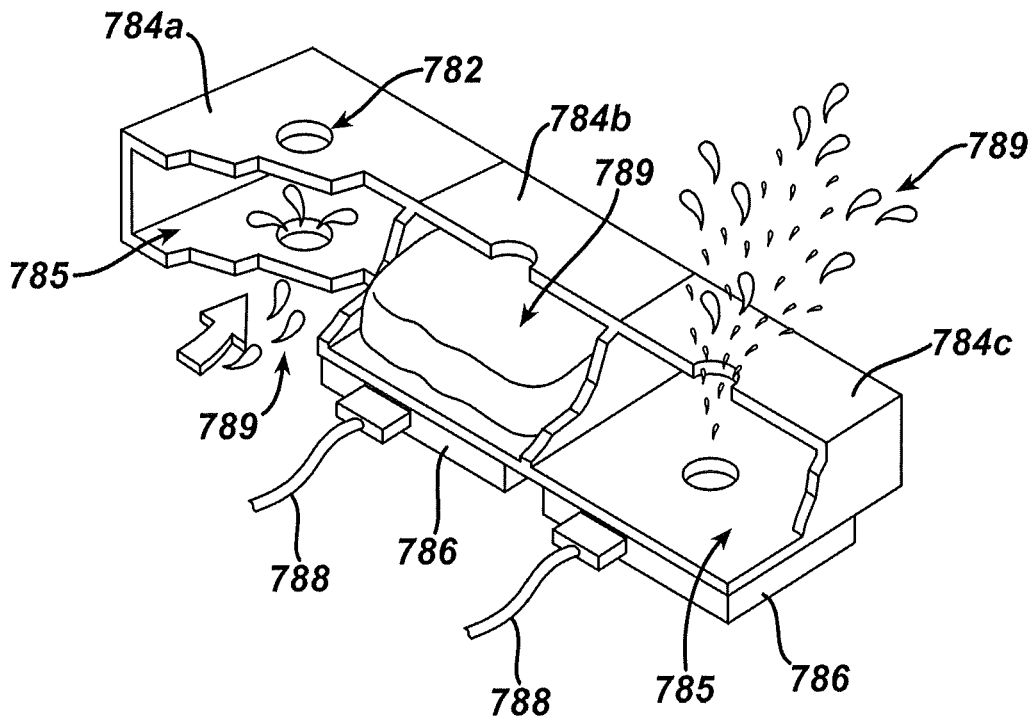
FIG. 30 depicts a partial perspective view of several examples of therapeutic agent delivery features that may be incorporated into the clamp pad of FIG. 29.

Clamp pad (780) of the present example includes a plurality of openings (782). Each opening (782) is associated with a respective therapeutic agent administration cell (784) in this example. As shown in FIG. 30, each cell (784) includes a reservoir (785) and a heat plate (786) that heats up in response to an appropriate signal. To that end, each plate (786) may have a corresponding wire (788) or other structure for receiving a signal. As shown in cell (784*a*), the reservoir (785) of each cell (784) may be filled with therapeutic agent (789). For instance, therapeutic agent (789) may be communicated to each reservoir (785) via a conduit and/or the various structures described below in section V.D.3. and/or in any other suitable fashion. As shown in cell (784*b*), heating of heat plate (786) by a signal applied through wire (788) causes therapeutic agent (789) to expand and ultimately blow out through opening (782) as shown in cell (784*c*).

As noted above, sonoporation provided by harmonic blade (774) may facilitate transfection in instances where therapeutic agent (789) comprises DNA/genes. Thus, in some examples, therapeutic agent (789) is administered when harmonic blade (774) is actively oscillating. To that end, cells (784) may be selectively activated to expel therapeutic agent (789) only when harmonic blade (774) is activated. For instance, cells (784) may be tied to the same control feature(s) (e.g., buttons) that is/are used to selectively activate harmonic blade (774). Alternatively, cells (784) may be operable for activation independent from activation of harmonic blade (774). It should also be understood that clamp pad (780) may be configured such that all cells (784) in clamp pad (780) are activated simultaneously to expel therapeutic agent (789). Alternatively, clamp pad (780) may be configured such that cells (784) in clamp pad (780) may be activated individually or in groups to expel therapeutic agent (789).

Figure 31:
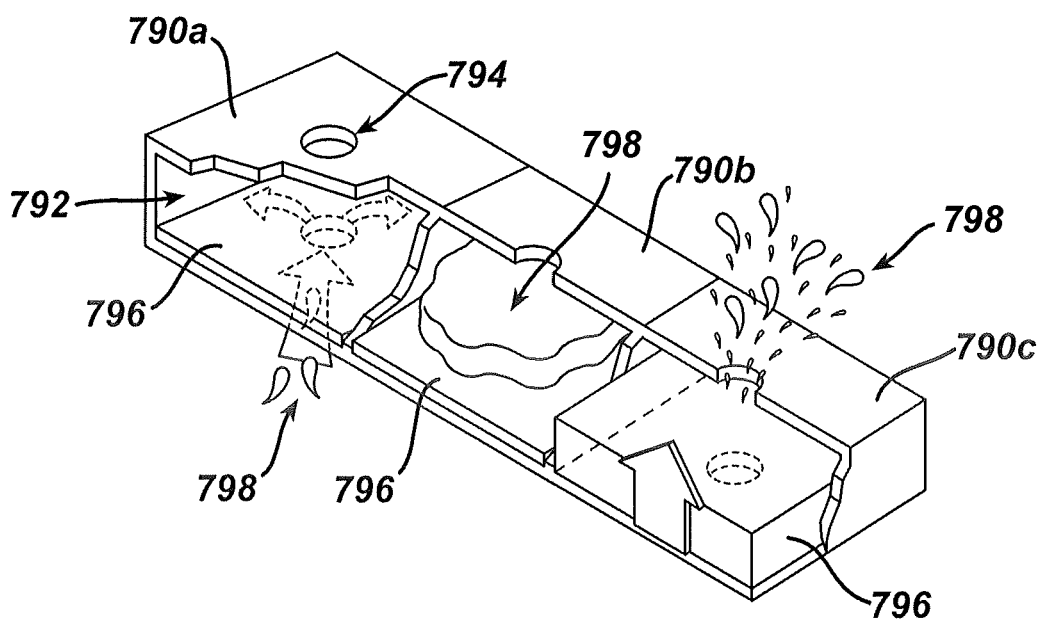
FIG. 31 depicts a partial perspective view of several other examples of therapeutic agent delivery features that may be incorporated into the clamp pad of FIG. 29.

FIG. 31 shows an exemplary alternative type of agent administration cell (790) that may be readily incorporated into clamp pad (780) in addition to or in lieu of using agent administration cells (784) described above. In this example, each cell (790) includes a reservoir (792). Each reservoir (792) is in fluid communication with a respective opening (794). In addition, a piezo stack (796) is provided in each reservoir (792). Each piezo stack (796) is configured to expand in response to an appropriate signal, thereby reducing the effective size of its corresponding reservoir (792). As shown in cell (790*a*), the reservoir (792) of each cell (790) may be filled with therapeutic agent (798). For instance, therapeutic agent (798) may be communicated to each reservoir (792) via a conduit and/or the various structures described below in section V.D.3. and/or in any other suitable fashion until the reservoir (792) is full as shown in cell (790*b*). As shown in cell (790*c*), application of an appropriate signal to piezo stack (796) causes peiozo stack (796) to expand and expel therapeutic agent (798) through opening (794). Still other suitable ways in which a therapeutic agent may be administered from cells will be apparent to those of ordinary skill in the art in view of the teachings herein. Similarly, other suitable ways in which a therapeutic agent may be administered from a clamp pad will be apparent to those of ordinary skill in the art in view of the teachings herein.

3. Exemplary Structures for Communicating Therapeutic Agent to End Effector of Surgical Device The examples described below relate to various structures and methods that may be used to provide communication of a therapeutic agent to the end effector of a surgical device. By way of example only, the below teachings may be readily incorporated with any of the teachings provided in sections V.B.2, V.D.1, and/or V.D.2, above. Still other settings in which the below teachings may be readily applied will be apparent to those of ordinary skill in the art in view of the teachings herein. For instance, while the following examples are provided in the context of harmonic surgical instruments, it should be understood that the following teachings may be readily applied to various other kinds of surgical instruments, other kinds of medical devices, etc. It should also be understood that various components, features, and operabilities of the below examples may be readily combined with each other in various ways, as will be apparent to those of ordinary skill in the art in view of the teachings herein.

Figure 32:
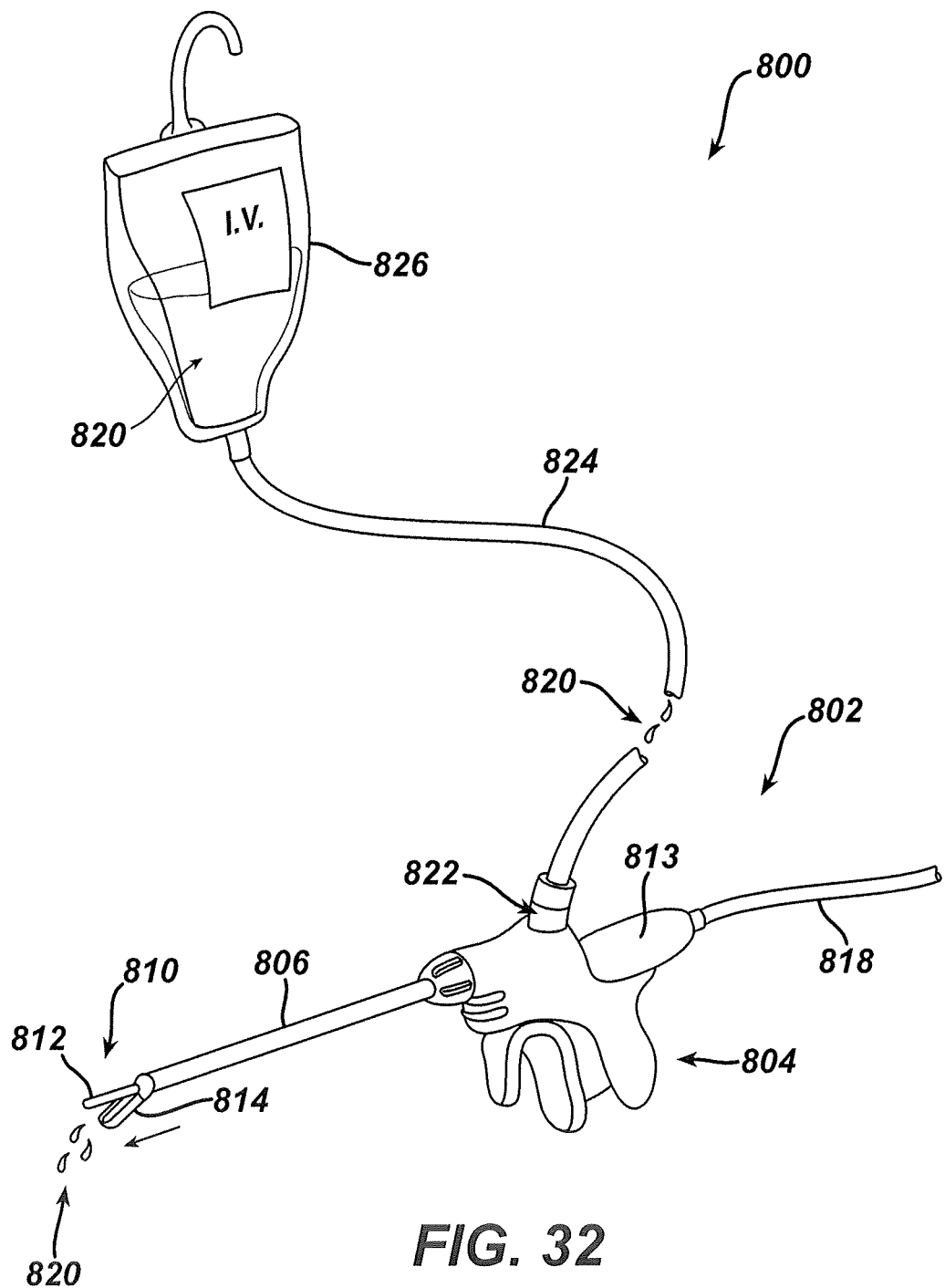
FIG. 32 depicts a perspective view of an exemplary harmonic surgical instrument coupled with a therapeutic agent source for delivery of the therapeutic agent through the harmonic surgical instrument.

FIG. 32 shows an exemplary therapeutic agent delivery system (800) that includes a harmonic surgical instrument (802) having a handpiece (804), a shaft (806), and an end effector (810). End effector (810) includes a harmonic blade (812) and a pivotable clamp pad (814). Harmonic blade (812) is energized by an ultrasonic transducer (813), which receives power from a cable (818) that is coupled with a generator (not shown). End effector (810) is operable to administer a therapeutic agent (820). It should therefore be understood that harmonic surgical instrument (802) may be configured and operable in accordance with any of the above teachings in sections V.B.2, V.D.1, and/or V.D.2. Of course, harmonic surgical instrument (802) may have any other suitable configuration and/or operability; and may even be a different kind of medical device. In the present example, handpiece (804) includes a fluid coupling (822), which is in fluid communication with end effector (810). A conduit (824) is coupled with coupling (822), such that conduit (824) is in fluid communication with end effector (810) via coupling (822). A bag (826) is also coupled with conduit (824). Bag (826) of this example includes a conventional IV bag containing therapeutic agent (820), though it should be understood that bag (826) may have any other suitable construction. Therapeutic agent (820) may comprise any therapeutic agent referred to herein or any other suitable type of therapeutic agent that will be apparent to those of ordinary skill in the art in view of the teachings herein. In some versions, bag (826) is positioned vertically higher than harmonic surgical instrument (802) during use of harmonic surgical instrument (802), such that therapeutic agent (820) is at least partially fed to end effector (810) by gravity. Of course, system (800) may also include one or more pumps that are operable to drive therapeutic agent (820) to end effector (810), including but not limited to any of the various kinds of pumps described below.

Figure 33:
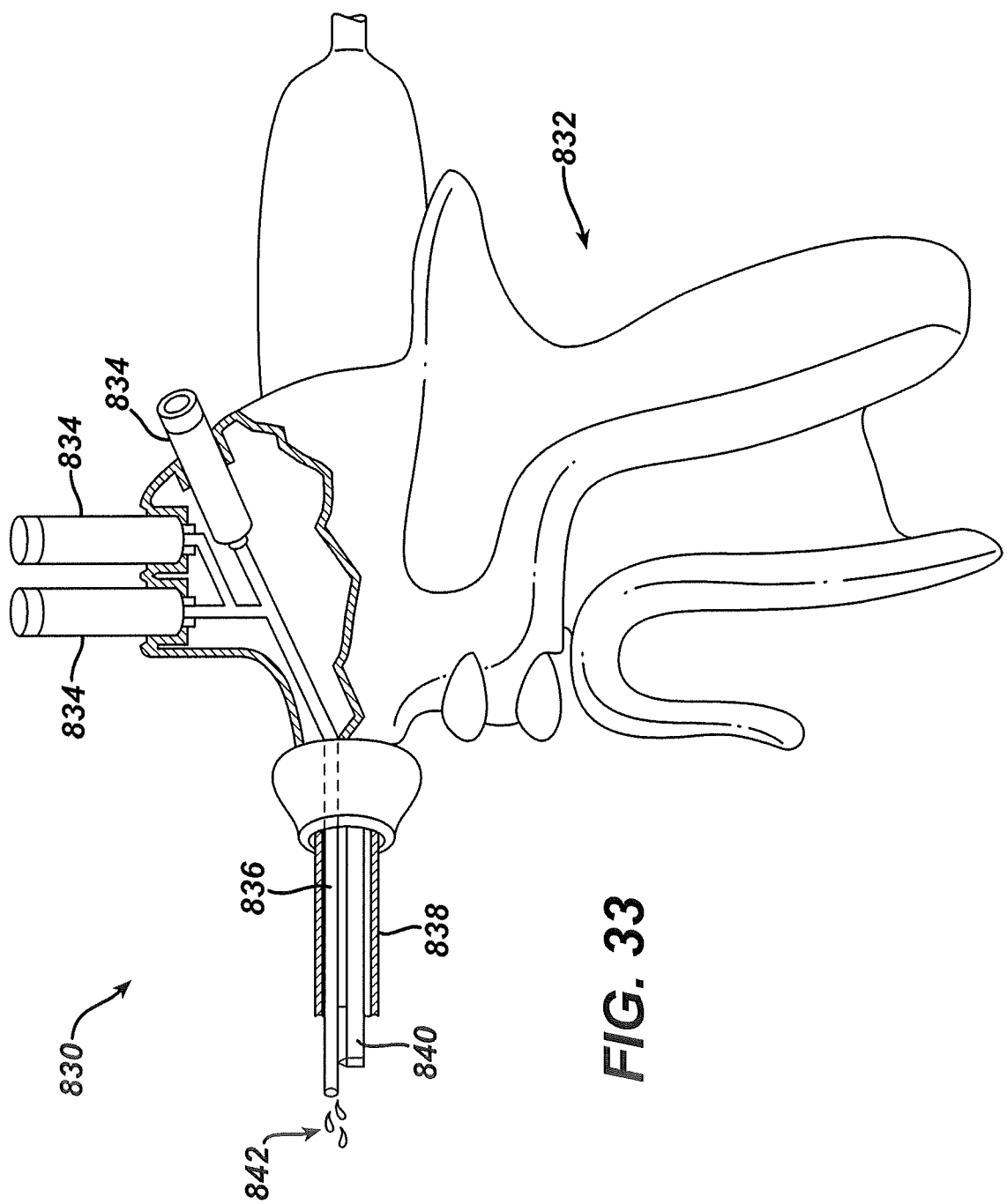
FIG. 33 depicts a partial side view of an exemplary harmonic surgical instrument with therapeutic agent sources provided in a handle portion.

FIG. 33 shows an exemplary harmonic surgical instrument (830) having a handpiece (832) with integral therapeutic agent cartridges (834). Cartridges (834) are in fluid communication with a conduit (836), which extends distally through shaft (838) alongside waveguide (840). Conduit (836) and waveguide (840) extend to an end effector (not shown) that is positioned at the distal end of shaft (838). The end effector is operable to administer a therapeutic agent (842) from cartridges (834). It should therefore be understood that harmonic surgical instrument (830) may be configured and operable in accordance with any of the above teachings in sections V.B.2, V.D.1, and/or V.D.2. Of course, harmonic surgical instrument (830) may have any other suitable configuration and/or operability; and may even be a different kind of medical device. It should be understood that cartridges (834) may be modular, each containing its own kind of therapeutic agent (842), such that a user may select from various cartridges (834) to tailor treatment to a given patient based on any suitable factors such as biomarker data, the kind of procedure in which harmonic surgical instrument (830) is being used, the location in the patient's anatomy in which harmonic surgical instrument (830) is being used, etc. By accommodating several cartridges (834), harmonic surgical instrument (830) further allows two or more therapeutic agents (842) to be combined for administration as a cocktail at the end effector. While handpiece (832) is shown with three cartridges (834), it should be understood that handpiece (832) may be made to accommodate any other suitable number of cartridges (834), such as one, two, or more than three.

In some versions, all cartridges provide therapeutic agent (842) to conduit (836) substantially simultaneously. In some other versions, handpiece (832) includes one or more valves (not shown) that allow therapeutic agent (842) to be selectively communicated from one or more cartridges (834) at any given time. For instance, one kind of therapeutic agent (842) may be communicated from only one of the cartridges (834) before a surgical procedure begins; with a second kind of therapeutic agent (842) being communicated from one of the other cartridges (834) during the surgical procedure; and with a third kind of therapeutic agent (842) being communicated from another one of the other cartridges (834) at the end of the surgical procedures. Various suitable ways in which handpiece (832) may be configured to provide such selective use of catridges (834) will be apparent to those of ordinary skill in the art in view of the teachings herein.

In the present example, the location and orientation of cartridges (834) in handpiece (832) allows therapeutic agent (842) to be at least partially fed to the end effector by gravity. Of course, harmonic surgical instrument (830) may also include one or more pumps that are operable to drive therapeutic agent (842) to the end effector, including but not limited to any of the various kinds of pumps described below. It should also be understood that harmonic surgical instrument (830) may be at least partially configured in accordance with the teachings of U.S. Pat. No. 7,673,783, entitled "Surgical Stapling Instruments Structured for Delivery of Medical Agents," issued Mar. 9, 2010, the disclosure of which is incorporated by reference herein. While U.S. Pat. No. 7,673,783 is provided in the context of a surgical stapling instrument, those of ordinary skill in the art will recognize that several of the teachings of U.S. Pat. No. 7,673,783 may be readily applied to harmonic surgical instrument (830). It should also be understood that a surgical stapler (or other medical device) constructed in accordance with the teachings of U.S. Pat. No. 7,673,783 may be used to administer a therapeutic agent based on biomarker data or otherwise, in accordance with the teachings herein.

Figure 34:
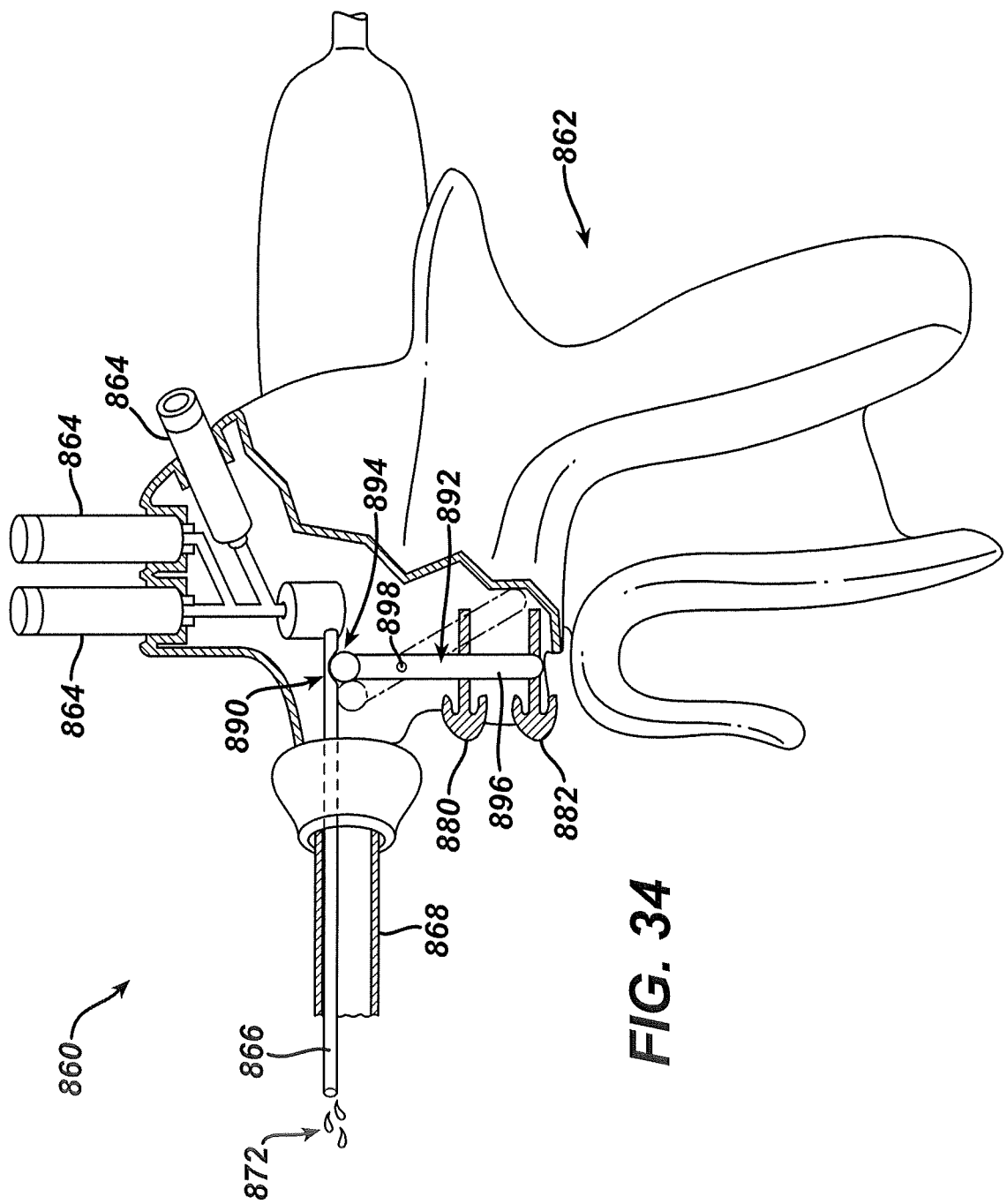
FIG. 34 depicts a partial side view of an exemplary harmonic surgical instrument with therapeutic agent sources provided in a handle portion and with a flow restriction feature also provided in the handle portion.
Figure 35A:
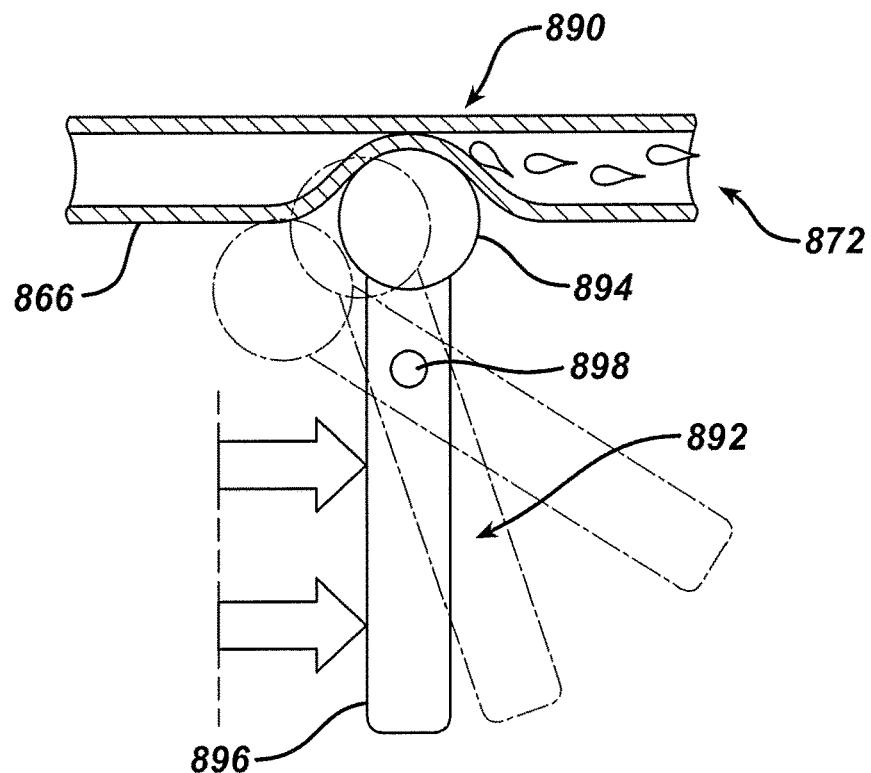
FIG. 35A depicts a side view of the flow restriction feature of FIG. 34 in a first use position.
Figure 35B:
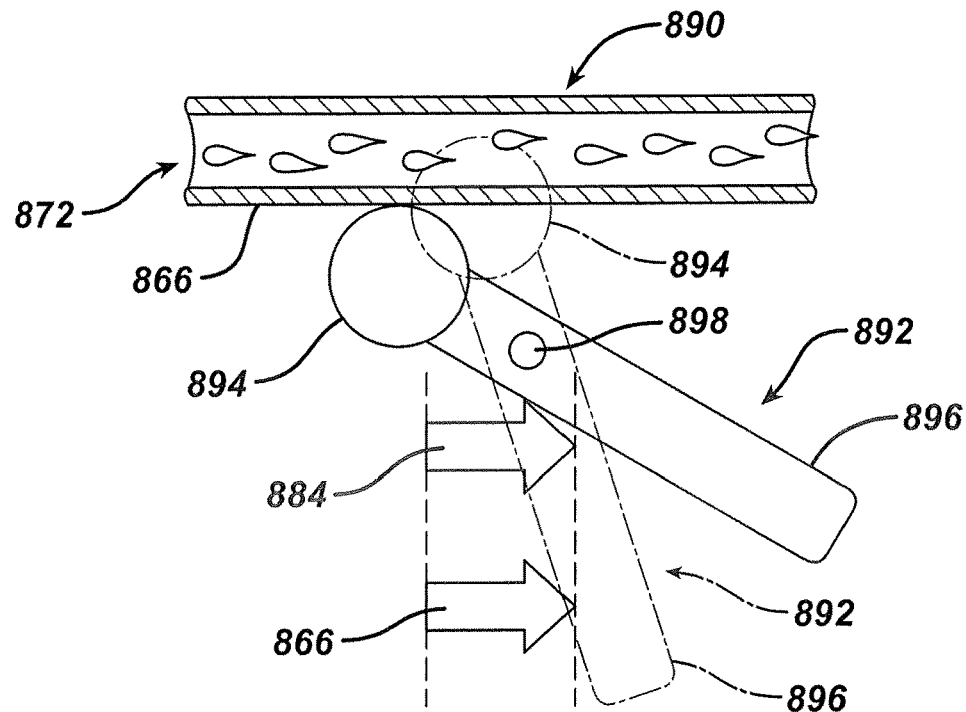
FIG. 35B depicts a side view of the flow restriction feature of FIG. 34 in second and third use positions.

FIGS. 34 and 35A-B show another exemplary harmonic surgical instrument (860), which is a merely illustrative variation of harmonic surgical instrument (830) shown in FIG. 33. In this example, harmonic surgical instrument (860) includes a handpiece (862) with integral therapeutic agent cartridges (864). Cartridges (864) are in fluid communication with a conduit (866), which extends distally through shaft (868) alongside a waveguide (not shown). Conduit (866) and the waveguide extend to an end effector (not shown) that is positioned at the distal end of shaft (868). The end effector is operable to administer a therapeutic agent (872) from cartridges (864). It should therefore be understood that harmonic surgical instrument (860) may be configured and operable in accordance with any of the above teachings in sections V.B.2, V.D.1, and/or V.D.2. Of course, harmonic surgical instrument (860) may have any other suitable configuration and/or operability; and may even be a different kind of medical device. It should be understood that cartridges (864) may be modular, as described above with respect to harmonic surgical instrument (830). While handpiece (862) is shown with three cartridges (864), it should be understood that handpiece (862) may be made to accommodate any other suitable number of cartridges (864), such as one, two, or more than three.

In some versions, all cartridges provide therapeutic agent (872) to conduit (866) substantially simultaneously. In some other versions, handpiece (862) includes one or more valves (not shown) that allow therapeutic agent (872) to be selectively communicated from one or more cartridges (864) at any given time, as described above with respect to harmonic surgical instrument (830). Similarly, the location and orientation of cartridges (864) in handpiece (862) allows therapeutic agent (872) to be at least partially fed to the end effector by gravity. Of course, harmonic surgical instrument (860) may also include one or more pumps that are operable to drive therapeutic agent (872) to the end effector, including but not limited to any of the various kinds of pumps described below. It should also be understood that harmonic surgical instrument (860) may be at least partially configured in accordance with the teachings of U.S. Pat. No. 7,673,783, entitled "Surgical Stapling Instruments Structured for Delivery of Medical Agents," issued Mar. 9, 2010, the disclosure of which is incorporated by reference herein.

Handpiece (862) of the present example also includes a pair of buttons (880, 882). Buttons (880, 882) are operable to selectively activate a harmonic blade at the end effector. For instance, one button (880) may provide maximum intensity while the other button (882) provides minimum intensity. Harmonic surgical instrument (860) of this example is configured such that either button (880, 882) must be held down in order to keep the harmonic blade in an active state, such that the harmonic blade returns to an inactive state as soon as a held button (880, 882) is released. Buttons (880, 882) are thus operable similar to buttons (142, 144) of device (100) described above.

Conduit (866) of the present example includes a variable restriction region (890) within handpiece (862). A variable restriction member (892) is positioned for selective contact with conduit (866) in this region (890), as best seen in FIGS. 35A-B. Variable restriction member (892) includes a conduit contact ball (894) and a lever arm (896); and is pivotable about a pin (898) that is fixedly secured in handpiece (862). Variable restriction member (892) is positioned in handpiece (862) such that buttons (880, 882) contact lever arm (896). Variable restriction member (892) is also resiliently biased (e.g., by a spring, etc.) to maintain a substantially vertical orientation as shown in FIG. 35A when neither button (880, 882) is being depressed. In this position, contact ball (894) pinches conduit (866) at region (890), effectively closing off conduit (866) at region (890). It should be understood that a contact surface (not shown) may be positioned above conduit (866) at region (890) to substantially prevent deformation of the top portion of conduit (866) at region (890), allowing contact ball (894) to effectively pinch conduit (866) closed at region (890) when variable restriction member (892) is in the upright position. Thus, in this example, no therapeutic agent (872) is communicated through conduit (866) past region (890) when neither button (880, 882) is being depressed. In other words, therapeutic agent (872) is only administered at the end effector when the harmonic blade is being activated by a button (880, 882) in this example.

As shown in FIG. 35B, therapeutic agent (872) is able to travel through conduit (866) past region (890) when either button (880, 882) is depressed, though the flow rate permitted through region (890) is based on which button (880, 882) is being depressed. In particular, when button (882) is depressed as indicated by arrow (886) to activate the harmonic blade at the minimum intensity, variable restriction member (892) is pivoted to a first rotational position. In this first position, contact ball (894) partially relieves conduit (866) of pinching yet still pinches conduit (866) enough to provide a reduced flow of therapeutic agent (872) through conduit (866). When button (880) is depressed as indicated by arrow (884) to activate the harmonic blade at maximum intensity, variable restriction member (892) is pivoted to a second rotational position. In this second position, contact ball (894) fully relieves conduit (866) of pinching to provide full flow of therapeutic agent (872) through conduit (866). Thus, in this example, the flow rate of therapeutic agent (872) to the end effector is tied directly to the intensity at which the harmonic blade oscillates. Various other suitable ways in which the flow rate of a therapeutic agent (872) may be tied to the intensity at which a harmonic blade oscillates (and/or be tied to some other operating parameter of a medical device) will be apparent to those of ordinary skill in the art in view of the teachings herein.

Figure 36:
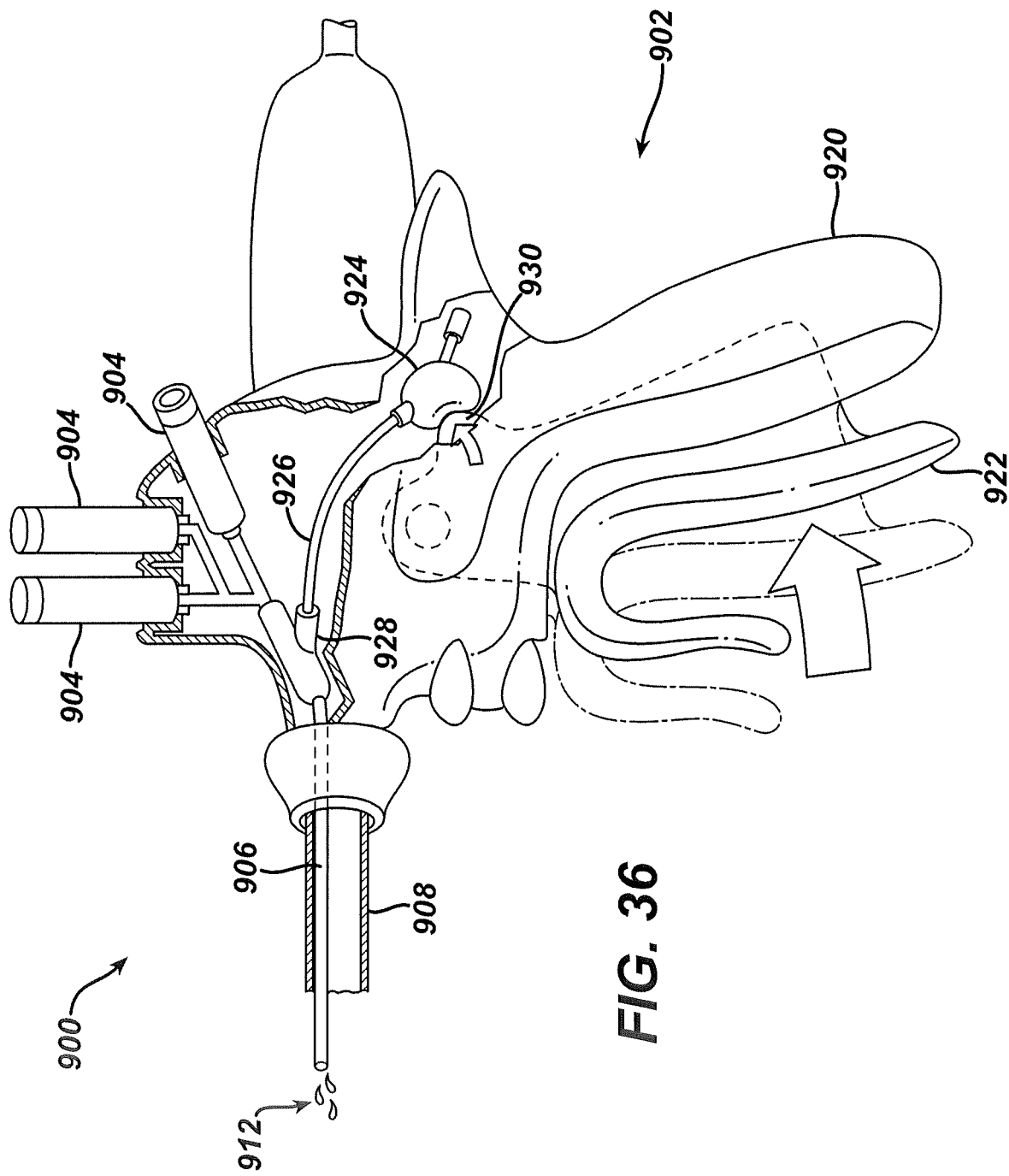
FIG. 36 depicts a partial side view of an exemplary harmonic surgical instrument with therapeutic agent sources provided in a handle portion and with a manual pump feature also provided in the handle portion.

FIG. 36 shows yet another exemplary harmonic surgical instrument (900), which is another merely illustrative variation of harmonic surgical instrument (830) shown in FIG. 33. In this example, harmonic surgical instrument (900) includes a handpiece (902) with integral therapeutic agent cartridges (904). Cartridges (904) are in fluid communication with a conduit (906), which extends distally through shaft (908) alongside a waveguide (not shown). Conduit (906) and the waveguide extend to an end effector (not shown) that is positioned at the distal end of shaft (908). The end effector is operable to administer a therapeutic agent (912) from cartridges (904). It should therefore be understood that harmonic surgical instrument (900) may be configured and operable in accordance with any of the above teachings in sections V.B.2, V.D.1, and/or V.D.2. Of course, harmonic surgical instrument (900) may have any other suitable configuration and/or operability; and may even be a different kind of medical device. It should be understood that cartridges (904) may be modular, as described above with respect to harmonic surgical instrument (830). While handpiece (902) is shown with three cartridges (904), it should be understood that handpiece (902) may be made to accommodate any other suitable number of cartridges (904), such as one, two, or more than three.

In some versions, all cartridges provide therapeutic agent (912) to conduit (906) substantially simultaneously. In some other versions, handpiece (902) includes one or more valves (not shown) that allow therapeutic agent (912) to be selectively communicated from one or more cartridges (904) at any given time, as described above with respect to harmonic surgical instrument (830). Similarly, the location and orientation of cartridges (904) in handpiece (902) allows therapeutic agent (912) to be at least partially fed to the end effector by gravity. Of course, harmonic surgical instrument (900) may also include one or more pumps that are operable to drive therapeutic agent (912) to the end effector, including but not limited to any of the various kinds of pumps described below. It should also be understood that harmonic surgical instrument (900) may be at least partially configured in accordance with the teachings of U.S. Pat. No. 7,673,783, entitled "Surgical Stapling Instruments Structured for Delivery of Medical Agents," issued Mar. 9, 2010, the disclosure of which is incorporated by reference herein.

Handpiece (902) of the present example includes a pistol grip (920), a trigger member (922), and a primer pump (924). Trigger member (922) is pivotable relative to pistol grip (920) to pivot a clamp pad (not shown) at the end effector toward a harmonic blade (not shown) at the end effector. Trigger member (922) is thus operable similar to trigger member (150) of device (100) described above. Primer pump (924) is coupled with a pump conduit (926), which is further coupled with a Y-fitting (928). Y-fitting (928) is in fluid communication with cartridges (904) and conduit (906). Primer pump (924) is operable to drive therapeutic agent (912) distally through conduit (906) when primer pump (924) is squeezed. To that end, trigger member (922) includes a protrusion (930) positioned adjacent to primer pump (924). Protrusion (930) is positioned and configured such that protrusion (930) squeezes primer pump (924) when trigger member (922) is pivotally squeezed toward pistol grip (920). Thus, harmonic surgical instrument (900) dispenses therapeutic agent (912) at the end effector when the clamp pad is pivoted toward the harmonic blade at the end effector by trigger member (922). Various other suitable ways in which the dispensation of a therapeutic agent (912) may be tied to the actuation of a clamp pad in a harmonic surgical instrument (and/or be tied to some other operating parameter of a medical device) will be apparent to those of ordinary skill in the art in view of the teachings herein.

Figure 37:
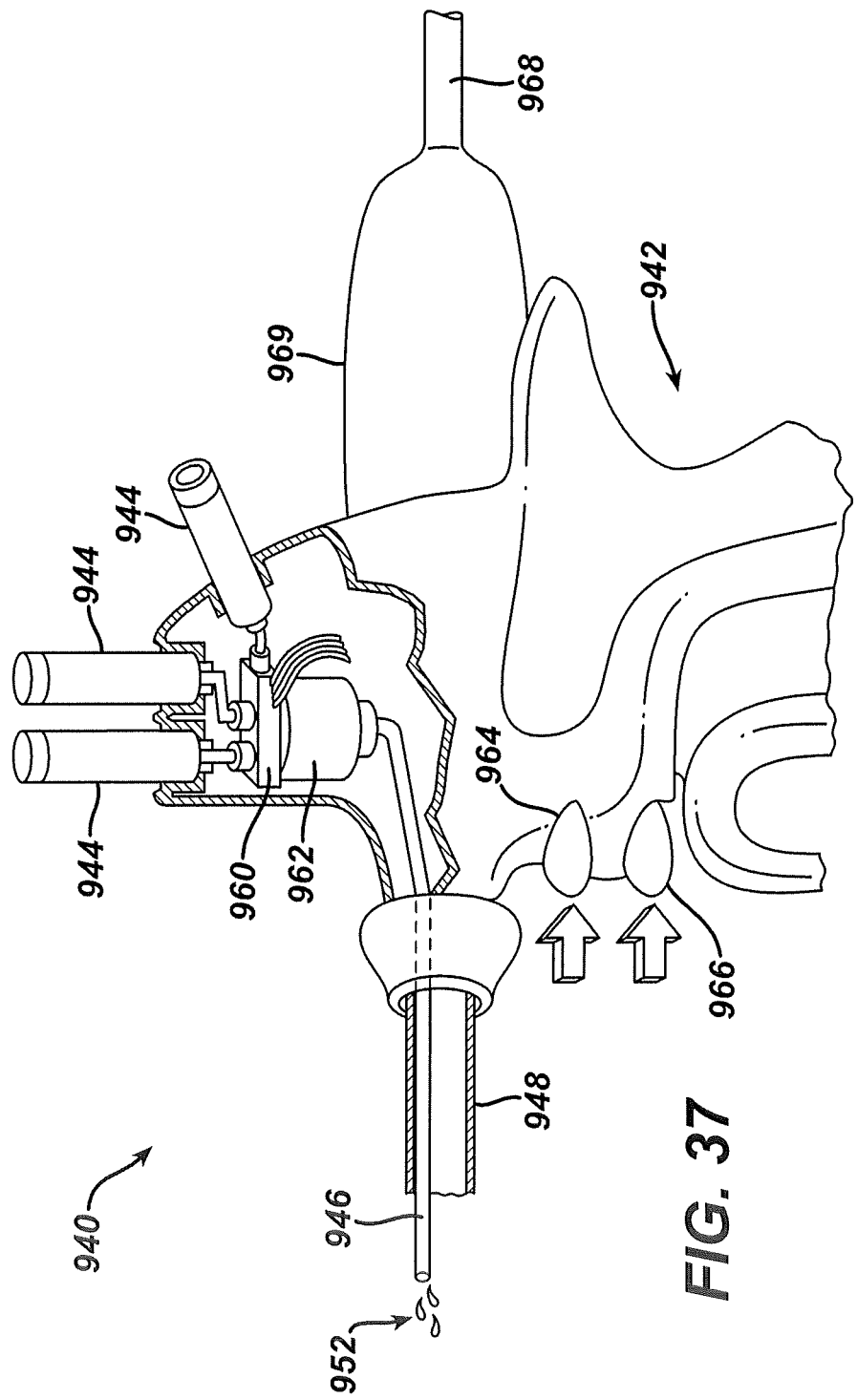
FIG. 37 depicts a partial side view of an exemplary harmonic surgical instrument with therapeutic agent sources provided in a handle portion and with an automated pump feature also provided in the handle portion.

FIG. 37 shows yet another exemplary harmonic surgical instrument (940), which is yet another merely illustrative variation of harmonic surgical instrument (830) shown in FIG. 33. In this example, harmonic surgical instrument (940) includes a handpiece (942) with integral therapeutic agent cartridges (944). Cartridges (944) are in fluid communication with a conduit (946), which extends distally through shaft (948) alongside a waveguide (not shown). Conduit (946) and the waveguide extend to an end effector (not shown) that is positioned at the distal end of shaft (948). The end effector is operable to administer a therapeutic agent (952) from cartridges (404). It should therefore be understood that harmonic surgical instrument (940) may be configured and operable in accordance with any of the above teachings in sections V.B.2, V.D.1, and/or V.D.2. Of course, harmonic surgical instrument (940) may have any other suitable configuration and/or operability; and may even be a different kind of medical device. It should be understood that cartridges (944) may be modular, as described above with respect to harmonic surgical instrument (830). While handpiece (942) is shown with three cartridges (904), it should be understood that handpiece (942) may be made to accommodate any other suitable number of cartridges (944), such as one, two, or more than three.

In some versions, all cartridges provide therapeutic agent (952) to conduit (946) substantially simultaneously. In some other versions, handpiece (942) includes one or more valves (not shown) that allow therapeutic agent (952) to be selectively communicated from one or more cartridges (944) at any given time, as described above with respect to harmonic surgical instrument (830). Similarly, the location and orientation of cartridges (944) in handpiece (942) allows therapeutic agent (952) to be at least partially fed to the end effector by gravity. Of course, harmonic surgical instrument (940) may also include one or more pumps that are operable to drive therapeutic agent (952) to the end effector, including but not limited to any of the various kinds of pumps described below. It should also be understood that harmonic surgical instrument (940) may be at least partially configured in accordance with the teachings of U.S. Pat. No. 7,673,783, entitled "Surgical Stapling Instruments Structured for Delivery of Medical Agents," issued Mar. 9, 2010, the disclosure of which is incorporated by reference herein.

Handpiece (942) of the present example includes a valve box (960) and an electromechanical pump (962), both of which are interposed between cartridges (944) and conduit (946). Handpiece (942) also includes a pair of buttons (964, 966). Buttons (964, 966) are operable to selectively activate a harmonic blade at the end effector. For instance, one button (964) may provide maximum intensity while the other button (966) provides minimum intensity. Harmonic surgical instrument (940) of this example is configured such that either button (964, 966) must be held down in order to keep the harmonic blade in an active state, such that the harmonic blade returns to an inactive state as soon as a held button (964, 966) is released. Buttons (964, 966) are thus operable similar to buttons (142, 144) of device (100) described above. In the present example, control of valve box (960) and pump (962) is tied to activation of buttons (964, 966). In particular, handpiece (942) is configured such that valve box (960) only opens one or more valves between cartridges (944) and pump (962) only when a button (964, 966) is depressed. When neither button (964, 966) is being depressed, valve box (960) closes off fluid communication from cartridges (944) to pump (962) in this example.

In addition, handpiece (942) of the present example is configured such that pump (962) drives therapeutic agent (952) distally through conduit (946) only when a button (964, 966) is depressed. When neither button (964, 966) is being depressed, pump (962) is simply deactivated. Thus, in this example, no therapeutic agent (952) is communicated to the end effector when neither button (964, 966) is depressed. In other words, therapeutic agent (952) is only administered at the end effector when the harmonic blade is being activated by a button (964, 966) in this example. Of course, harmonic surgical instrument (940) may alternatively be configured such that valve box (960) and/or pump (962) are operable independently relative to buttons (964, 966), such that therapeutic agent (952) may be administered at times when the harmonic blade is not being activated. It should also be understood that harmonic surgical instrument (940) may be configured such that the flow rate through conduit (946) is based on which button (964, 966) is being depressed. Furthermore, it should be understood that pump (962) may be configured such that therapeutic agent (952) is not communicable through pump (962) when pump (962) is deactivated, such that valve box (960) may simply be omitted in some versions. In the present example, pump (962) receives power from the same cable (968) that drives ultrasonic transducer (969) (which in turn drives the harmonic blade at the end effector), though it should be understood that pump (962) may be powered in any other suitable fashion (e.g., by a battery positioned in handpiece (942). Various other suitable components, features, configurations, and operabilities that may be provided in harmonic surgical instrument (940) will be apparent to those of ordinary skill in the art in view of the teachings herein.

Figure 39:
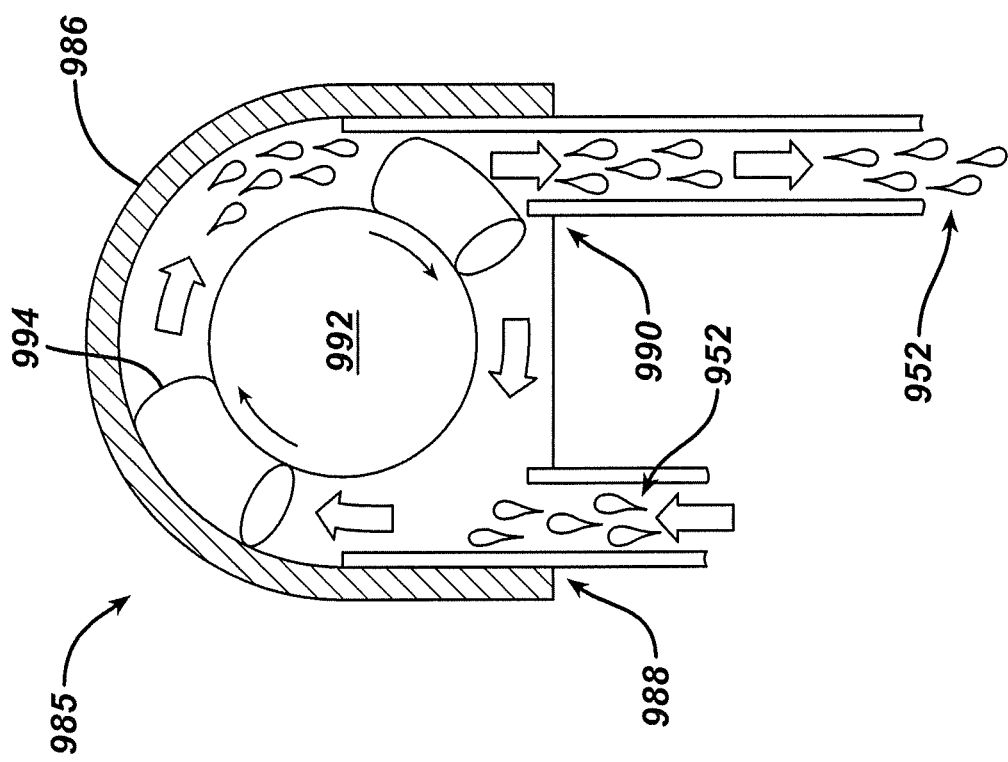
FIG. 39 depicts a side cross-sectional view of another exemplary structure that may be incorporated into the automated pump feature of FIG. 37.
Figure 38:
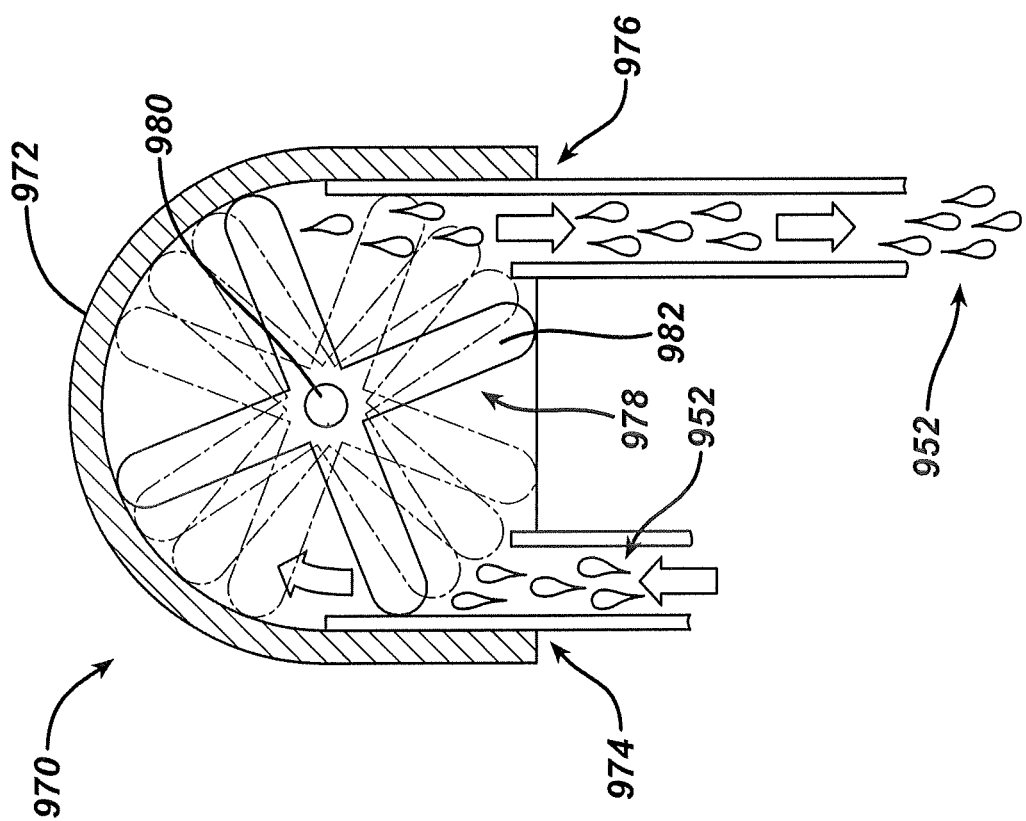
FIG. 38 depicts a side cross-sectional view of an exemplary structure that may be incorporated into the automated pump feature of FIG. 37.

FIGS. 38-39 show merely illustrative examples of pumping components that may be included in pump (962) of harmonic surgical instrument (940). In particular, FIG. 38 shows a pump (970) that includes a pump housing (972) with an inlet (974) and an outlet (976). Referring back to harmonic surgical instrument (940) of FIG. 37, inlet (974) may be coupled with valve box (960) (or directly with cartridges (944) in versions where valve box (960) is omitted); while outlet (976) is coupled with conduit (946). A pump wheel (978) is provided within housing (972) and is rotatable about an axle (980). Pump wheel (978) includes a plurality of outwardly extending fins (982) providing a star shaped cross sectional profile. While four fins (982) are shown it should be understood that any suitable number of fins (982) may be used. Fins (982) are configured to drive therapeutic agent (952) from inlet (974) toward outlet (976) when pump wheel (978) is rotated about axle (980). In some versions, this rotation of pump wheel (978) drives therapeutic agent (952) through outlet (976) and conduit (946) in a pulsed stream. In some other versions, this rotation of pump wheel (978) drives therapeutic agent (952) through outlet (976) and conduit (946) in a continuous stream.

FIG. 39 shows a pump (985) that includes a pump housing (986) with an inlet (988) and an outlet (990). Referring again back to harmonic surgical instrument (940) of FIG. 37, inlet (988) may be coupled with valve box (960) (or directly with cartridges (944) in versions where valve box (960) is omitted); while outlet (990) is coupled with conduit (946). A pump wheel (992) is provided within housing (986) and is rotatable within housing (986). A pair of driving cylinders (994) are secured to the exterior of pump wheel (992) and rotate unitarily with pump wheel (992). While two driving cylinders (994) are shown it should be understood that any suitable number of driving cylinders (994) may be used. Driving cylinders (994) are configured to drive therapeutic agent (952) from inlet (988) toward outlet (990) when pump wheel (992) is rotated within housing (986). In some versions, this rotation of pump wheel (991) drives therapeutic agent (952) through outlet (990) and conduit (946) in a pulsed stream. In some other versions, this rotation of pump wheel (992) drives therapeutic agent (952) through outlet (990) and conduit (946) in a continuous stream. Various other suitable ways in which pump (962) may be configured will be apparent to those of ordinary skill in the art in view of the teachings herein.

4. Exemplary Administration of Therapeutic Agent Separate from Surgical Device

The examples described below relate to various additional structures and methods that may be used to provide communication of a therapeutic agent to a surgical site or other wound site. By way of example only, the below teachings may be readily incorporated with any of the teachings provided in section V.B.2, above. Still other settings in which the below teachings may be readily applied will be apparent to those of ordinary skill in the art in view of the teachings herein. It should also be understood that various components, features, and operabilities of the below examples may be readily combined with each other in various ways, as will be apparent to those of ordinary skill in the art in view of the teachings herein.

Figure 40:
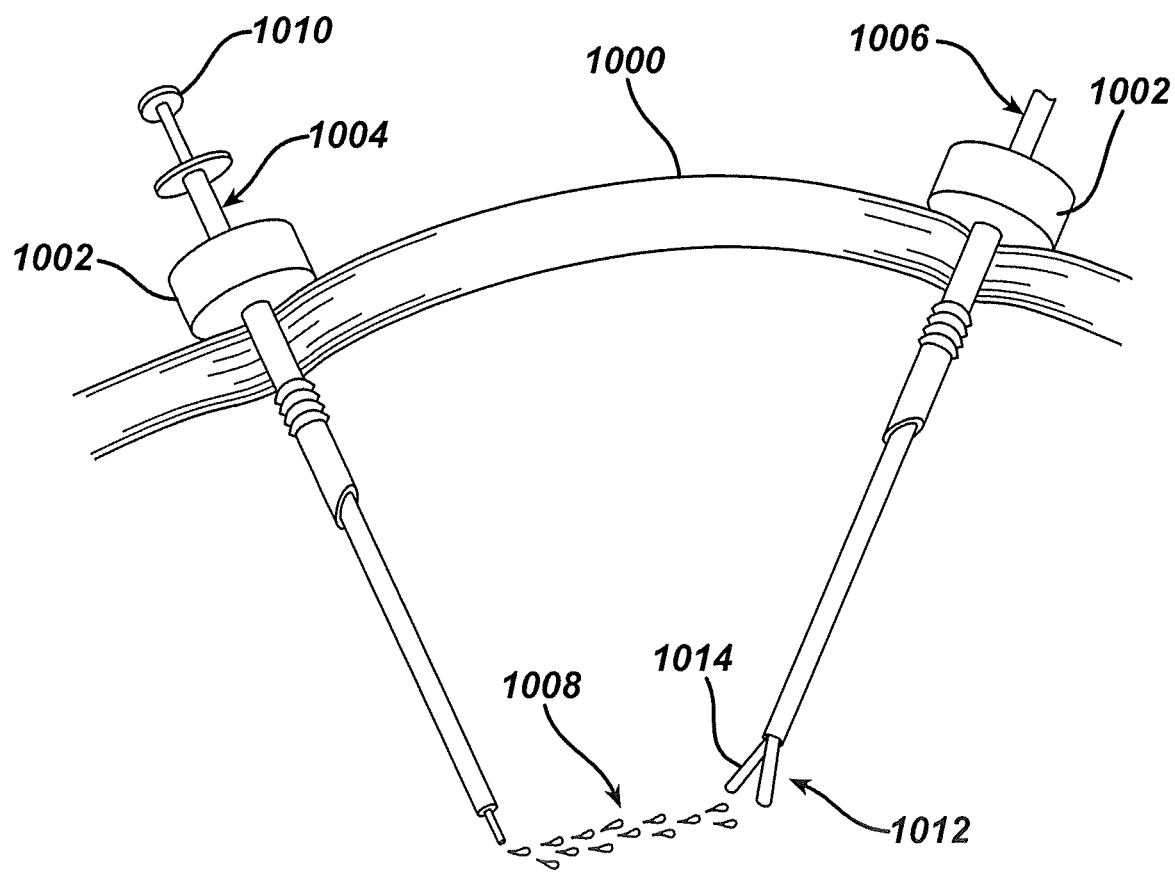
FIG. 40 depicts a partial cross-sectional view of a patient's abdomen with a therapeutic agent delivery device and a harmonic surgical instrument inserted through the abdominal wall.

FIG. 40 shows a pair of trocars (1002) inserted through the abdominal wall (1000) of a patient. A therapeutic agent delivery device (1004) is disposed through one of the trocars (1002) while the shaft (1006) of a harmonic surgical device is disposed through the other trocar (1002). A plunger (1010) of the therapeutic agent delivery device (1004) is depressed to administer a therapeutic agent (1008) at a surgical site, adjacent to the end effector (1012) at the distal end of shaft (1006). In some versions, this is done to pre-soak the patient's tissue with therapeutic agent (1008) at the surgical site before the harmonic blade (1014) of end effector (1012) is activated. In addition or in the alternative, therapeutic agent (1008) may be administered at the surgical site during activation of harmonic blade (1014) and/or after harmonic blade (1014) has been activated then de-activated. In some instances, different therapeutic agent delivery devices (1004) containing different therapeutic agents (1008) may be fed through trocar (1002) at different stages during surgery. Thus, while several above examples relate to surgical instruments that create wounds during surgery also being used to administer a therapeutic agent, it should be understood that a completely separate device may be used to administer a therapeutic agent. It should also be understood that, as with all other examples described herein, therapeutic agent (1008) may be selected and administered based on biomarker data and/or based on various other factors.

Figure 41:
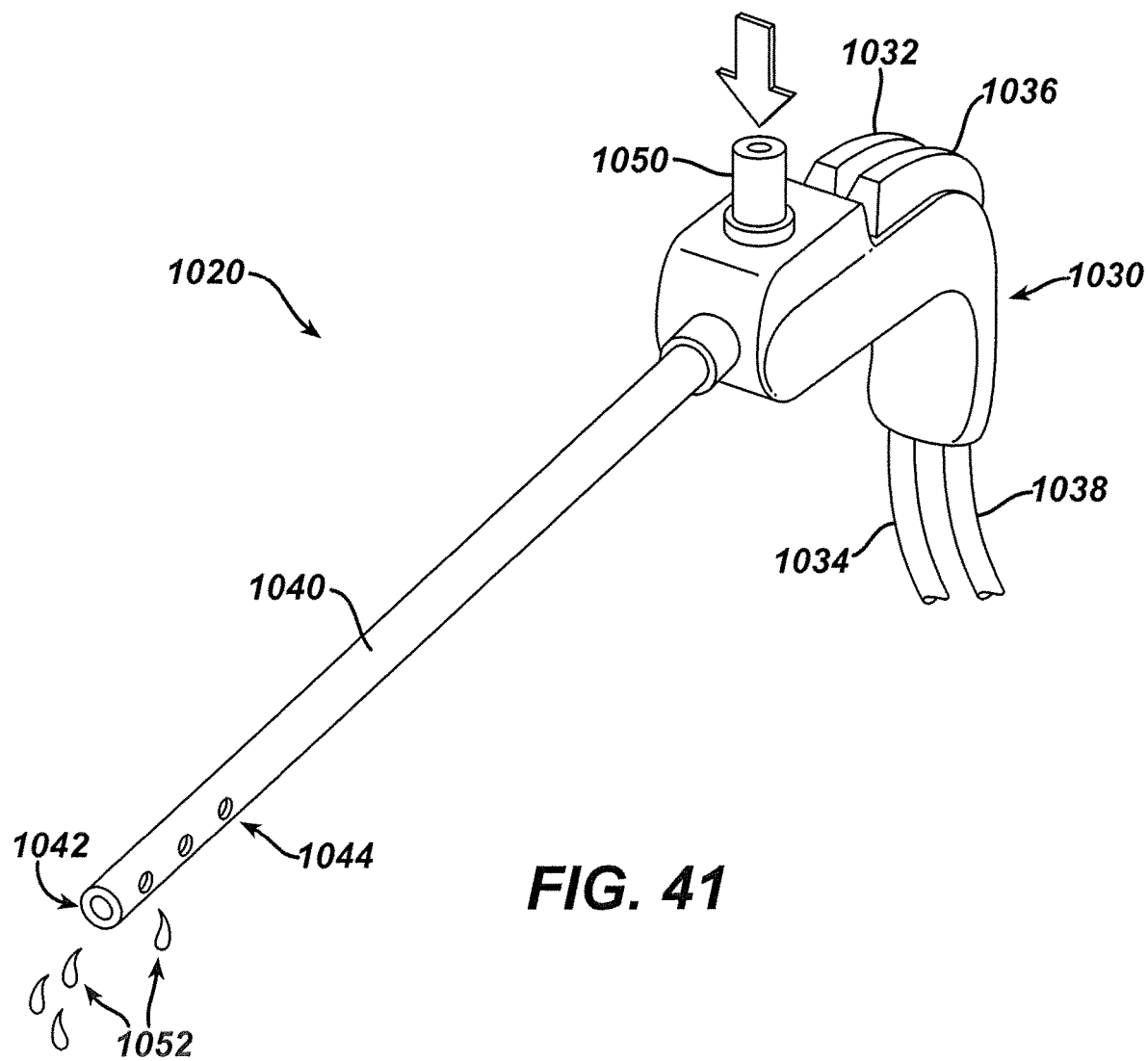
FIG. 41 depicts a perspective view of an exemplary alternative therapeutic agent delivery device.

FIG. 41 shows another exemplary therapeutic agent delivery device (1020). Therapeutic agent delivery device (1020) of this example includes a handpiece (1030) and a shaft (1040) extending distally from handpiece (1030). Handpiece (1030) of this example includes an irrigation button (1032) and a suction button (1036). Shaft (1040) of this example is substantially hollow, and the distal end of shaft (1040) includes a distal opening (1042) and a plurality of side openings (1044), such that shaft (1040) is operable to dispense various fluids from handpiece (1030) as described below. An irrigation tube (1034) and a suction tube (1038) are coupled with handpiece (1030). In some versions, irrigation tube (1034) is further coupled with a source of saline. In some other versions, irrigation tube (1034) coupled with a source of therapeutic agent (1052). In addition, suction tube (1038) is coupled with a conventional suction source in some versions. In some other versions, suction tube (1038) is coupled with a capture vessel (180) or a biomarker processing module (230) as described above. Irrigation button (1032) is operable to selectively couple shaft (1040) with irrigation tube (1034); while suction button (1036) is operable to selectively couple shaft (1040) with suction tube (1038).

Handpiece (1030) also includes a therapeutic agent cartridge (1050) and is operable to selectively couple shaft (1040) with cartridge (1050). For instance, in some versions, shaft (1040) is coupled with cartridge (1050) when irrigation button (1032) is activated, such that saline or some other fluid medium communicated through irrigation tube (1034) drives therapeutic agent (1052) from cartridge (1050) through openings (1042, 1044) at the distal end of shaft (1040) when irrigation button (1032) is activated. Alternatively, a separate button or other feature may be provided to selectively administer therapeutic agent (1052) from cartridge (1050) through openings (1042, 1044).

In some versions, shaft (1040) is sized to fit through a trocar. Thus, referring back to FIG. 40, and by way of example only, shaft (1040) may be fed through a trocar (1002) instead of feeding therapeutic agent delivery device (1004) through trocar (1002). With the distal end of shaft (1040) positioned adjacent to a surgical site or other wound site, suction button (1036) may be activated (e.g., while harmonic blade (1014) is activated) to obtain biomarker data in accordance with block (10) of FIG. 1, in accordance with the teachings of section V.A., above, and/or in accordance with other teachings herein. Irrigation button (1032) (or some other feature) may then be used to administer therapeutic agent (1052) at the surgical site or other wound site based on the acquired biomarker data, in accordance with block (60) of FIG. 1, in accordance with the teachings of section V.B., above, and/or in accordance with other teachings herein. In addition or in the alternative, other actions may be taken in response to the biomarker data (e.g., in accordance with blocks (70, 80, and/or 90) of FIG. 1). Still other suitable ways in which therapeutic agent delivery device (1020) may be configured and used will be apparent to those of ordinary skill in the art in view of the teachings herein.

Figure 42:
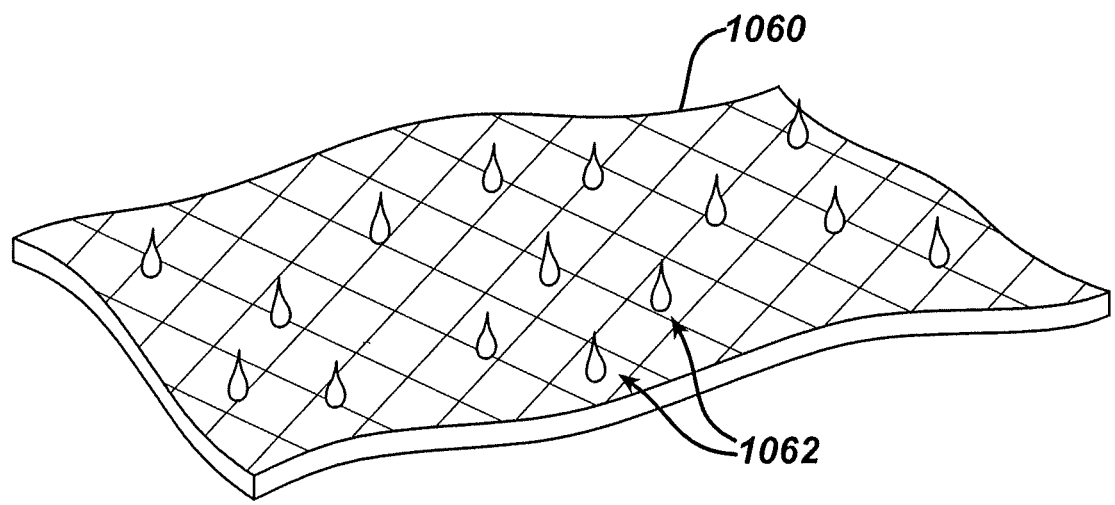
FIG. 42 depicts a perspective view of an exemplary therapeutic agent delivery pad.
Figure 43:
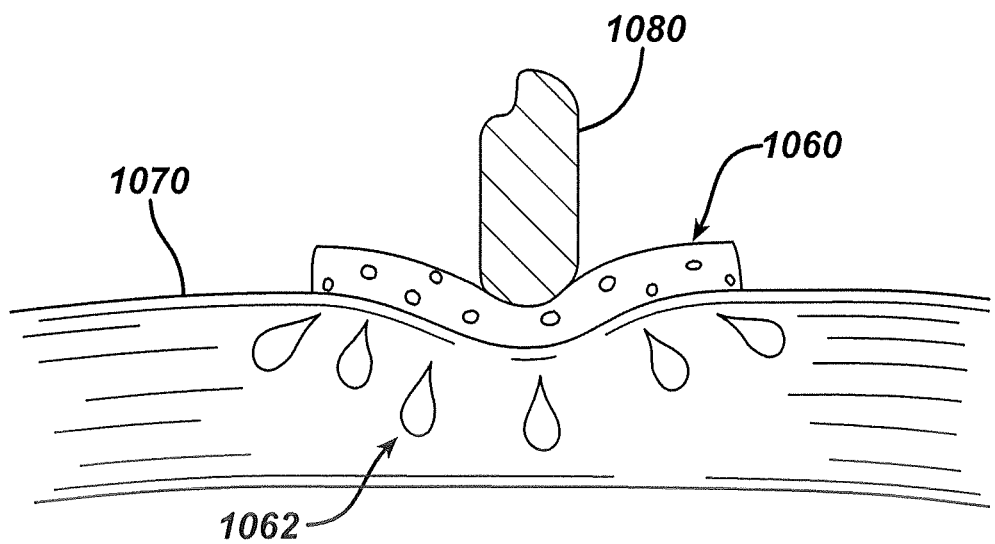
FIG. 43 depicts a cross-sectional view of a harmonic blade being used to activate the therapeutic agent delivery pad of FIG. 42 against a patient's tissue.

FIGS. 42-43 show another exemplary structure and method for delivering a therapeutic agent to a surgical site or other wound site. In particular, FIG. 42 shows a therapeutic agent pad (1060) impregnated with a therapeutic agent (1062). In this example, therapeutic agent (1062) comprises a gene therapy substance, but as with all other examples described herein, therapeutic agent (1062) may alternatively comprise any other suitable therapeutic agent. In an exemplary use, pad (1060) is placed against a patient's tissue (1070). Then, a harmonic blade (1080) of a harmonic surgical instrument is positioned over pad (1060), such that pad (1060) is interposed between harmonic blade (1080) and the patient's tissue (1070). When harmonic blade (1080) is activated, harmonic blade (1080) provides sonoporation in the patient's tissue (1070) as described above, while simultaneously driving therapeutic agent (1062) from pad (1060) into the patient's tissue (1070). Various suitable structures and materials that may be used for pad (1060) will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a shaft that includes a distal end;
(b) a conduit extending at least partially outside of the shaft at the distal end of the shaft;

(c) an end effector positioned at the distal end of the shaft, wherein the end effector comprises:
  (i) an ultrasonic blade, and
  (ii) a clamp arm, wherein the clamp arm is pivotable relative to the ultrasonic blade between an open configuration where the clamp arm is pivotably spaced from the ultrasonic blade and a closed configuration where the clamp arm is configured to clamp tissue against the ultrasonic blade, wherein the clamp arm comprises one or more openings in fluid communication with the conduit that are configured to selectively transmit a fluid outwardly from the clamp arm and toward the ultrasonic blade; and
(d) a reservoir in fluid communication with the conduit to selectively deliver a fluid through the clamp arm via the one or more openings of the clamp arm.

2. The apparatus of claim 1, further comprising a waveguide extending through the shaft, wherein the waveguide is configured to transmit ultrasonic energy from an ultrasonic transducer to the ultrasonic blade.

3. The apparatus of claim 1, wherein the one or more openings are selectively activatable to release the fluid through the end effector.

4. The apparatus of claim 3, further comprising a wire in electrical communication with a controller, wherein the wire is configured to apply a signal to the one or more openings to selectively activate the one or more openings to control release of the fluid through the end effector.

5. The apparatus of claim 3, wherein all of the one or more openings are selectively activatable simultaneously.

6. The apparatus of claim 3, wherein the one or more openings comprise multiple openings, wherein the multiple openings are selectively activatable in groups of one or more.

7. The apparatus of claim 1, wherein the one or more openings comprise an active state and an inactive state, wherein in the active state the fluid is releasable through the one or more openings, wherein when in the inactive state the fluid is prevented from releasing through the one or more openings.

8. The apparatus of claim 7, wherein in the inactive state the one or more openings are at least partially closed to prevent communication of the fluid through the one or more openings.

9. The apparatus of claim 1, wherein delivery of the fluid through the end effector is dependent upon the ultrasonic blade being in an oscillating state.

10. The apparatus of claim 1, wherein the fluid is saline.

11. The apparatus of claim 1, wherein the ultrasonic blade does not pivot relative to the clamp arm when transitioning between the open and closed configurations.

12. An instrument, comprising:
(a) a shaft that includes a distal end;
(b) a conduit extending at least partially outside of the shaft at the distal end of the shaft,
(c) an end effector positioned at the distal end of the shaft, wherein the end effector comprises:
  (i) an ultrasonic blade, and
  (ii) a clamp arm, wherein the clamp arm is pivotable relative to the ultrasonic blade, wherein the clamp arm comprises one or more openings in fluid communication with the conduit that are configured to selectively transmit a fluid outwardly from the clamp arm and toward the ultrasonic blade; and
(d) a reservoir in fluid communication with the conduit and configured to selectively retain the fluid for transmission from the clamp arm.

13. The instrument of claim 12, wherein the shaft includes a waveguide that is configured to transmit ultrasonic energy from an ultrasonic transducer to the ultrasonic blade.

14. The instrument of claim 12, wherein the reservoir contains a finite volume of the fluid.

15. The instrument of claim 12, wherein the one or more openings comprise a plurality of openings, wherein the clamp arm includes a clamp pad, wherein the clamp pad includes the plurality of openings that are uniformly distributed throughout the clamp pad.

16. The instrument of claim 12, wherein the ultrasonic blade does not pivot relative to the clamp arm when transitioning between the open and closed configurations.

17. The instrument of claim 12, wherein the one or more orifices are selectively activated to only open when the ultrasonic blade is activated, wherein the one or more orifices substantially close up when the ultrasonic blade is inactive.

18. An apparatus comprising:
(a) a shaft that extends along a longitudinal axis, wherein the shaft includes a distal end;
(b) a conduit extending at least partially outside of the shaft at the distal end of the shaft;
(c) a waveguide extending through the shaft, wherein the waveguide is configured to transmit ultrasonic energy from an ultrasonic transducer;
(d) an end effector positioned at the distal end of the shaft, wherein the end effector comprises:
  (i) an ultrasonic blade coupled with the waveguide, and
  (ii) a clamp arm, wherein the clamp arm is pivotable relative to the ultrasonic blade, wherein the clamp arm is angled relative to the longitudinal axis in an open configuration and generally parallel to the longitudinal axis in a closed configuration, wherein the clamp arm comprises one or more openings in fluid communication with the conduit; and
(e) a reservoir in fluid communication with the conduit to selectively deliver a fluid through the clamp arm via the one or more openings of the clamp arm.

19. The apparatus of claim 18, wherein the one or more openings comprise an active state and an inactive state, wherein in the active state the fluid is releasable through the one or more openings, wherein when in the inactive state the fluid is prevented from releasing through the one or more openings.

20. The apparatus of claim 18, wherein the one or more openings are configured to selectively transmit the fluid outwardly from the clamp arm and toward the ultrasonic blade.

* * * * *